US011866481B2

(12) United States Patent
Lenferink et al.

(10) Patent No.: US 11,866,481 B2
(45) Date of Patent: Jan. 9, 2024

(54) TGF-β-RECEPTOR ECTODOMAIN FUSION MOLECULES AND USES THEREOF

(71) Applicant: NATIONAL RESEARCH COUNCIL OF CANADA, Ottawa (CA)

(72) Inventors: Anne E. G. Lenferink, Lorraine (CA); John C. Zwaagstra, Laval (CA); Traian Sulea, Kirkland (CA); Maureen D. O'Connor-McCourt, Beaconsfield (CA)

(73) Assignee: National Research Council of Canada, Ottawa (CA)

( * ) Notice: Subject to any disclaimer, the term of this patent is extended or adjusted under 35 U.S.C. 154(b) by 290 days.

(21) Appl. No.: 16/490,335

(22) PCT Filed: Mar. 1, 2018

(86) PCT No.: PCT/IB2018/051320
§ 371 (c)(1),
(2) Date: Aug. 30, 2019

(87) PCT Pub. No.: WO2018/158727
PCT Pub. Date: Sep. 7, 2018

(65) Prior Publication Data
US 2022/0204587 A1    Jun. 30, 2022

Related U.S. Application Data

(60) Provisional application No. 62/468,586, filed on Mar. 8, 2017, provisional application No. 62/465,969, filed on Mar. 2, 2017.

(51) Int. Cl.
| C07K 14/71 | (2006.01) |
| A61P 35/00 | (2006.01) |
| A61K 38/00 | (2006.01) |

(52) U.S. Cl.
CPC .............. *C07K 14/71* (2013.01); *A61P 35/00* (2018.01); *A61K 38/00* (2013.01); *C07K 2319/30* (2013.01)

(58) Field of Classification Search
CPC ............ C07K 2319/00; C07K 2319/30; C07K 2319/32; A61K 38/00
See application file for complete search history.

(56) References Cited

U.S. PATENT DOCUMENTS

| 5,693,607 | A | 12/1997 | Segarini et al. |
| 6,277,375 | B1 | 8/2001 | Ward |
| 8,318,135 | B2 | 11/2012 | O'Connor-McCourt et al. |
| 8,658,135 | B2 | 2/2014 | O'Connor-McCourt et al. |
| 8,815,247 | B2 | 8/2014 | Govindappa et al. |
| 9,782,452 | B2 | 10/2017 | Scandura et al. |
| 9,809,637 | B2 | 11/2017 | Kumar et al. |
| 2002/0004037 | A1 | 1/2002 | Koteliansky et al. |
| 2005/0203022 | A1 | 9/2005 | Gotwals et al. |
| 2007/0244042 | A1 | 10/2007 | Sun et al. |
| 2011/0293512 | A1 | 12/2011 | Violette et al. |
| 2013/0149304 | A1 | 6/2013 | Lin et al. |
| 2015/0056199 | A1 | 2/2015 | Kumar et al. |
| 2015/0225483 | A1 | 8/2015 | Lo |
| 2018/0327477 | A1 | 11/2018 | Kumar et al. |
| 2020/0231652 | A1 | 7/2020 | Zwaagstra et al. |
| 2022/0169702 | A1 | 6/2022 | Zwaagstra et al. |

FOREIGN PATENT DOCUMENTS

| CA | 2330939 A1 | 12/1999 |
| CA | 2791383 A1 | 9/2011 |
| CA | 2902830 A1 | 10/2014 |
| CN | 1257545 A | 6/2000 |
| CN | 105658672 A | 6/2016 |
| EP | 3 174 550 B1 | 6/2017 |
| EP | 3589663 A1 | 1/2020 |
| JP | 2001-515360 A | 9/2001 |
| JP | 2010-529859 A | 9/2010 |
| JP | 2012-530514 A | 12/2012 |
| JP | 2016-037488 A | 3/2016 |
| JP | 2017-501977 A | 1/2017 |
| KR | 10-2001-0006534 A | 1/2001 |
| RU | 2413769 C1 | 3/2011 |
| WO | WO 95/04069 A1 | 2/1995 |
| WO | WO 98/48024 A1 | 10/1998 |
| WO | WO 01/83525 A2 | 11/2001 |
| WO | WO 2004/076670 A1 | 9/2004 |
| WO | WO 2005/028517 A2 | 3/2005 |
| WO | WO 2005/103263 A1 | 11/2005 |
| WO | WO 2008/113185 A1 | 9/2008 |
| WO | WO 2008/157367 A1 | 12/2008 |
| WO | WO 2010/003118 A1 | 1/2010 |
| WO | WO 2010/031168 A1 | 3/2010 |
| WO | WO 2010/099219 A2 | 9/2010 |
| WO | WO 2011/005481 A1 | 1/2011 |
| WO | WO 2011/109789 A2 | 9/2011 |
| WO | WO 2012/071649 A1 | 6/2012 |
| WO | WO 2012/142515 A2 | 10/2012 |
| WO | WO 2013/000234 A1 | 1/2013 |
| WO | WO 2014/164427 A1 | 10/2014 |
| WO | WO 2015/027082 A1 | 2/2015 |
| WO | WO 2015/077540 A3 | 5/2015 |
| WO | WO 2017/037634 A1 | 3/2017 |
| WO | WO 2019/191100 A1 | 10/2019 |
| WO | WO 2019/211489 A1 | 11/2019 |
| WO | WO 2020/093024 A2 | 5/2020 |
| WO | WO 2020/146345 A1 | 7/2020 |
| WO | WO 2021/123902 A1 | 6/2021 |
| WO | WO 2021/248247 A1 | 12/2021 |
| WO | WO 2022/271915 A1 | 12/2022 |

OTHER PUBLICATIONS

Govinden and Bhoola, 2003, Pharmacology and Therapeutics, vol. 98, pp. 257-265 (Year: 2003).*

(Continued)

*Primary Examiner* — Karen A. Canella
(74) *Attorney, Agent, or Firm* — Wolf, Greenfield & Sacks, P.C.

(57) ABSTRACT

The present invention relates, in general, to polypeptides capable of binding and neutralizing transforming growth factor beta (TGF-β) ligands, and uses of these polypeptides for treating disorders related to TGF-beta expression or activation (e.g. cancer and fibrotic diseases), and methods of making such molecules.

43 Claims, 15 Drawing Sheets

Specification includes a Sequence Listing.

(56) References Cited

OTHER PUBLICATIONS

Paul, Fundamental Immunology (textbook), 1993, 3rd Edition, p. 285, Figure 1 (Year: 1993).*
Lahn et al, Expert Opinion in Investigational Drugs, 2005, vol. 14, pp. 629-643 (Year: 2005).*
IMGT Scientific chart, ("human IGHG", downloaded from the web on Aug. 9, 2017) (Year: 2017).*
Schlingensiepen et al (Recent Results in Cancer Research, 2008, vol. 177, pp. 137-150) (Year: 2008).*
The abstract of Guba and Desaiah (Annals of oncology, 2016, vol. 27, suppl. 6, abstract No. 1102TiP) (Year: 2016).*
Zwaagstra supplementa materials and methods, 2012 (Year: 2012).*
Akhurst et al., "Targeting the TGF signalling pathway in disease," Macmillan Publishers Limited, Oct. 2012, vol. 11, 23 pages.
Arteaga, "Inhibition of TGFβ signaling in cancer therapy," Current Opinion in Genetics & Development 2006, 16:30-37.
Bogdahn et al., "Targeted therapy for high-grade glioma with the TGF-b2 inhibitor trabedersen: results of a randomized and controlled phase IIb study," Neuro-Oncology 13(1):132-142, 2011.
Corcoran et al., "BRAF Gene Amplification Can Promote Acquired Resistance to MEK Inhibitors in Cancer Cells Harboring the BRAF V600E Mutation," www.sciencesignaling.org, Nov. 23, 2010, vol. 3, Issue 149, 12 pages.
De Crescenzo et al, "Real-time Monitoring of the Interactions of Transforming Growth Factor-β (TGF-β) Isoforms with Latency-associated Protein and the Ectodomains of the TGF-β Type II and III Receptors Reveals Different Kinetic Models and Stoichiometries of Binding" The Journal of Biological Chemistry, 2001, vol. 276, No. 32, pp. 29632-29643.
Durocher et al., "High-level and high-throughput recombinant protein production by transient transfection of suspension-growing human 293-EBNA1 cells," Nucleic Acids Research, 2002, vol. 30, No. 2 e9.
Economides et al., "Cytokine traps: multi-component, high-affinity blockers of cytokine action," Nature Medicine, vol. 9, No. 1, Jan. 2003.
Engelman et al., "Acquired resistance to tyrosine kinase inhibitors during cancer therapy," Current Opinion in Genetics & Development 2008, 18:73-79.
Eisenberg et al., "Analysis of Membrane and Surface Protein Sequences with the Hydrophobic Moment Plot," J. Mol. Biol. (1984) 179, 125-142.
Flavell et al., "The polarization of immune cells in the tumour environment by TGFβ," www.nature.com/reviews/immunol, Aug. 2010, vol. 10, 14 pages.
Gajewski, "The next hurdle in cancer immunotherapy: Overcoming the non-T cell-inflamed tumor microenvironment," Semin Oncol. Aug. 2015; 42(4): 663-671.
Garberg et al., "In vitro models for the blood-brain barrier," Toxicology in Vitro 19 (2005) 299-334.
Hahn et al., "Targeting transforming growth factor β to enhance cancer immunotherapy," Current Oncology, vol. 13, No. 4, 3 pages.
Haqqani et al., "Multiplexed Evaluation of Serum and CSF Pharmacokinetics of Brain-Targeting Single-Domain Antibodies Using a NanoLC-SRM-ILIS Method," Mol. Pharmaceutics 2013, 10, 1542-1556.
Hawinkels et al., "Exploring anti-TGF-β therapies in cancer and fibrosis," Growth Factors, Aug. 2011; 29(4): 140-152.
Heldin et al., "Mechanism of TGF-β signaling to growth arrest, apoptosis, and epithelial—mesenchymal transition," Current Opinion in Cell Biology 2009, 21:166-176.
Holash et al., "VEGF-Trap: A VEGF blocker with potent antitumor effects," PNAS Aug. 20, 2002, vol. 99, No. 17, 11393-11398.
International Search Report and Written Opinion dated Jun. 4, 2018, for International Application No. PCT/IB2018/051320, 10 pages.
Isaka et al, "Gene therapy by transforming growth factor-β receptor-IgG Fc chimera suppressed extracellular matrix accumulation in experimental glomerulonephritis" Kidney International, 1999, vol. 55, pp. 465-475.
Jin et al., "Rational Optimization of a Bispecific Ligand Trap Targeting EGF Receptor Family Ligands," Mol. Med. 15 (1-2) 11-20, Jan.-Feb. 2009, 10 pages.
Komesli et al, "Chimeric extracellular domain of type II transforming growth factor (TGF)-β receptor fused to the Fc region of human immunoglobulin as a TGF-β antagonist" European Journal of Biochemistry, 1998, vol. 254, pp. 505-513.
Li et al., "Transforming Growth Factor-Regulation of Immune Responses," Annu. Rev. Immunol. 2006, 24:99-146.
Lin et al., "Mechanistic basis and clinical relevance of the role of transforming growth factor-β in cancer,"; accepted May 12, 2015, 12 pages.
Massague et al., "TGFb Signaling in Growth Control, Cancer, and Heritable Disorders,"Cell, vol. 103, 295-309, Oct. 13, 2000.
Mourskaia et al., "Targeting Aberrant TGF-β Signaling in Pre-Clinical Models of Cancer," Anti-Cancer Agents in Medicinal Chemistry, 2007, 7, 504-514.
Padua et al., "Roles of TGFβ in metastasis," Cell Research (2009) 19:89-102.
Rodgarkia-Dara et al., "The activin axis in liver biology and disease," Mutation Research 613 (2006) 123-137.
Rodon Ahnert et al., "First human dose (FHD) study of the oral transforming growth factor-beta receptor I kinase inhibitor LY2157299 in patients with treatment-refractory malignant glioma," Journal of Clinical Oncology 29, No. 15_suppl (May 20, 2011) 3011-3011.
Santarpia et al., "Programmed cell death protein-1/programmed cell death ligand-1 pathway inhibition and predictive biomarkers: understanding transforming growth factor-beta role," Transl Lung Cancer Res 2015; 4(6): 728-742.
Schlingensiepen et al., "Targeted tumor therapy with the TGF-b2 antisense compound AP 12009," Cytokine & Growth Factor Reviews 17 (2006) 129-139.
Schlingensiepen et al., "Transforming growth factor-beta 2 gene silencing with trabedersen (AP 12009) in pancreatic cancer," Cancer Sci, Jun. 2011, vol. 102, No. 6, 1193-1200.
Thiery et al., "Epithelial-Mesenchymal Transitions in Development and Disease," Cell 139, Nov. 25, 2009 Elsevier Inc., 20 pages.
Wojtowicz-Praga, "Reversal of tumor-induced immunosuppression by TGF-β inhibitors," Investigational New Drugs 21: 21-32, 2003.
Yang et al., "TGF-β and immune cells: an important regulatory axis in the tumor microenvironment and progression," Trends in Immunology 31 (2010) 220-227.
Yang et al., "Enlarging the repertoire of therapeutic monoclonal antibodies platforms: domesticating half molecule exchange to produce stable IgG4 and IgG1 bispecific antibodies," Current Opinion in Biotechnology 2014, 30:225-229.
Zheng et al., "Silencing IDO in dendritic cells: A novel approach to enhance cancer immunotherapy in a murine breast cancer model," Int. J. Cancer: 132, 967-977 (2013).
Zwaagstra et al, "Engineering and Therapeutic Application of Single-Chain Bivalent TGF-β Family Traps" Molecular Cancer Therapeutics, 2012, vol. 11, No. 7, pp. 1477-1487.
[No Author Listed] Aflibercept: AVE 0005, AVE 005, AVE0005, VEGF Trap—Regeneron, VEGF Trap (R1R2), VEGF Trap-Eye. Drugs R&D. 2008;9:261-9.
Akhurst, Targeting TGF-β Signaling for Therapeutic Gain. Cold Spring Harb Perspect Biol. Oct. 3, 2017;9(10):a022301. doi: 10.1101/cshperspect.a022301.
Akilesh et al., Neonatal FcR expression in bone marrow-derived cells functions to protect serum IgG from catabolism. J Immunol. Oct. 1, 2007;179(7):4580-8.
Allanore et al., Systemic sclerosis. Nat Rev Dis Primers. Apr. 23, 2015;1:15002. doi: 10.1038/nrdp.2015.2. 21 pages.
Baardsnes et al., TbetaR-II discriminates the high- and low-affinity TGF-beta isoforms via two hydrogen-bonded ion pairs. Biochemistry. Mar. 17, 2009;48(10):2146-55. doi: 10.1021/bi8019004.
Biswas et al. Anti-transforming growth factor-beta antibody treatment rescues bone loss and prevents breast cancer metastasis to bone. PloS one 2011;6:e27090.
Boocock et al., Mutations in SBDS are associated with Shwachman-Diamond syndrome. Nat Genet. Jan. 2003;33(1):97-101. doi: 10.1038/ng1062. Epub Dec. 23, 2002.

(56) References Cited

OTHER PUBLICATIONS

Bragado et al., TGF-β2 dictates disseminated tumour cell fate in target organs through TGF-β-RIII and p38α/β signalling. Nat Cell Biol. Nov. 2013;15(11):1351-61.doi: 10.1038/ncb2861. Epub Oct. 27, 2013.
De Crescenzo et al., Enhancement of the antagonistic potency of transforming growth factor-beta receptor extracellular domains by coiled coil-induced homo- and heterodimerization. J Biol Chem. Jun. 18, 2004;279(25):26013-8. doi: 10.1074/jbc.M400655200. Epub Mar. 24, 2004.
Desmouliere et al., Transforming growth factor-beta 1 induces alpha-smooth muscle actin expression in granulation tissue myofibroblasts and in quiescent and growing cultured fibroblasts. J Cell Biol. Jul. 1993;122(1):103-11. doi: 10.1083/jcb.122.1.103.
Edwards et al. Inhibition of TGF-beta signaling by 1D11 antibody treatment increases bone mass and quality in vivo. J Bone Miner Res 2010;25:2419-26.
Gabrielli et al., Scleroderma. N Engl J Med. May 7, 2009;360(19):1989-2003. doi: 10.1056/NEJMra0806188.
Gourh et al., Transforming Growth Factor Beta 3 (TGFB3)—a Novel Systemic Sclerosis Susceptibility Locus Involved in Fibrosis and Th17 Cell Development Identified by Genome-Wide Association Study in African Americans from the Genome Research in African American Scleroderma Patients Consortium. Arthritis & Rheumatology. 2017. 69(suppl 10).
Grütter et al., A cytokine-neutralizing antibody as a structural mimetic of 2 receptor interactions. Proc Natl Acad Sci U S A. Dec. 23, 2008;105(51):20251-6. Epub Dec. 10, 2008. doi: 10.1073/pnas.0807200106.
Guba et al., A Phase 1b/2 Dose Escalation and Cohort Expansion Study of the Safety, Tolerability and Efficacy of a Transforming Growth Factor-beta (TGF-beta) Receptor I Kinase Inhibitor (galunisertib) in Combination with Anti-PD-1 (nivolumab) in Advanced Refractory Solid Tumors. Annals Oncol. 2016;27(Supplement 6):vi359-vi378. doi: 10.1093/annonc/mdw378.55. 1 page.
Herbertz et al., Clinical development of galunisertib (LY2157299 monohydrate), a small molecule inhibitor of transforming growth factor-beta signaling pathway. Drug Des Devel Ther. Aug. 10, 2015;9:4479-99. doi: 10.2147/DDDT.S86621.
Hsu et al., Complement activation mediates cetuximab inhibition of non-small cell lung cancer tumor growth in vivo. Mol Cancer. Jun. 7, 2010;9:139. doi: 10.1186/1476-4598-9-139.
Huang, Receptor-Fc fusion therapeutics, traps, and MIMETIBODY technology. Curr Opin Biotech 2009;20:692-9.
Hunzelmann et al., Scleroderma: from pathophysiology to novel therapeutic approaches. Exp Dermatol. May 2010;19(5):393-400. doi: 10.1111/j.1600-0625.2010.01082.x.
Kissin et al., Myofibroblasts and hyalinized collagen as markers of skin disease in systemic sclerosis. Arthritis Rheum. Nov. 2006;54(11):3655-60. doi: 10.1002/art.22186.
Komai et al., Reevaluation of Pluripotent Cytokine TGF-β3 in Immunity. Int J Mol Sci. Aug. 1, 2018;19(8):2261. doi: 10.3390/ijms19082261.
Lacouture et al., Cutaneous keratoacanthomas/squamous cell carcinomas associated with neutralization of transforming growth factor β by the monoclonal antibody fresolimumab (GC1008). Cancer Immunol Immunother. Apr. 2015;64(4):437-46. Epub Jan. 13, 2015. doi: 10.1007/s00262-015-1653-0.
Lafyatis, Transforming growth factor β—at the centre of systemic sclerosis. Nat Rev Rheumatol. Dec. 2014; 10(12):706-19. Epub Aug. 19, 2014. doi: 10.1038/nrrheum.2014.137.
Langer et al., Quantitative trait analysis reveals transforming growth factor-beta2 as a positive regulator of early hematopoietic progenitor and stem cell function. J Exp Med. Jan. 5, 2004;199(1):5-14. doi: 10.1084/jem.20030980.
Leask, Targeting the TGFbeta, endothelin-1 and CCN2 axis to combat fibrosis in scleroderma. Cell Signal. Aug. 2008;20(8):1409-14. Epub Jan. 19, 2008. doi: 10.1016/j.cellsig.2008.01.006.
Martin et al., Selective inhibition of TGFβ1 activation overcomes primary resistance to checkpoint blockade therapy by altering tumor immune landscape. Sci Transl Med. Mar. 25, 2020;12(536):eaay8456. doi: 10.1126/scitranslmed.aay8456.
Mayes et al., Prevalence, incidence, survival, and disease characteristics of systemic sclerosis in a large US population. Arthritis Rheum. Aug. 2003;48(8):2246-55. doi: 10.1002/art.11073.
Meng et al., TGF-β: the master regulator of fibrosis. Nat Rev Nephrol. Jun. 2016;12(6):325-38. Epub Apr. 25, 2016. doi: 10.1038/nrneph.2016.48.
Midgley et al., Transforming growth factor-β1 (TGF-β1)-stimulated fibroblast to myofibroblast differentiation is mediated by hyaluronan (HA)-facilitated epidermal growth factor receptor (EGFR) and CD44 co-localization in lipid rafts. J Biol Chem. May 24, 2013;288(21):14824-38. Epub Apr. 15, 2013. doi: 10.1074/jbc.M113.451336.
Montoyo et al., Conditional deletion of the MHC class I-related receptor FcRn reveals the sites of IgG homeostasis in mice. Proc Natl Acad Sci U S A. Feb. 24, 2009;106(8):2788-93. doi:; 10.1073/pnas.0810796106. Epub Feb. 2, 2009.
Morris et al., Phase I study of GC1008 (fresolimumab): a human anti-transforming growth factor-beta (TGFβ) monoclonal antibody in patients with advanced malignant melanoma or renal cell carcinoma. PLOS One. Mar. 11, 2014;9(3):e90353. doi: 10.1371/journal.pone.0090353.
Muraoka et al., Blockade of TGF-beta inhibits mammary tumor cell viability, migration, and metastases. J Clin Invest. Jun. 2002;109(12):1551-9.
Nam et al. An anti-transforming growth factor beta antibody suppresses metastasis via cooperative effects on multiple cell compartments. Cancer Res 2008;68:3835-43.
Nam et al. Transforming growth factor beta subverts the immune system into directly promoting tumor growth through interleukin-17. Cancer Res 2008;68:3915-23.
Nanthakumar et al., Dissecting fibrosis: therapeutic insights from the small-molecule toolbox. Nat Rev Drug Discov. Oct. 2015;14(10):693-720. Epub Sep. 4, 2015. doi: 10.1038/nrd4592.
Pickup et al., The roles of TGF β in the tumour microenvironment. Nat Rev Cancer. Nov. 2013;13(11):788-99. doi: 10.1038/nrc3603. Epub Oct. 17, 2013.
Prud'Homme et al., Pathobiology of transforming growth factor beta in cancer, fibrosis and immunologic disease, and therapeutic considerations. Lab Invest. Nov. 2007;87(11):1077-91. Epub Aug. 27, 2007. doi: 10.1038/labinvest.3700669.
Qin et al., A novel highly potent trivalent TGF-β receptor trap inhibits early-stage tumorigenesis and tumor cell invasion in murine Pten-deficient prostate glands. Oncotarget. Dec. 27, 2016;7(52):86087-86102. doi: 10.18632/oncotarget.13343. Erratum in: Oncotarget. Aug. 21, 2017;8(34):57905.
Rice et al., A longitudinal biomarker for the extent of skin disease in patients with diffuse cutaneous systemic sclerosis. Arthritis Rheumatol. Nov. 2015;67(11):3004-15. doi: 10.1002/art.39287.
Rio et al., TGF-β: a master regulator of the bone marrow failure puzzle in Fanconi anemia. Stem Cell Investig. Nov. 7, 2016;3:75. doi: 10.21037/sci.2016.09.17.
Roberts et al., Role of transforming growth factor-beta in maintenance of function of cultured neonatal cardiac myocytes. Autocrine action and reversal of damaging effects of interleukin-1. J Clin Invest. Nov. 1992;90(5):2056-62. doi: 10.1172/JCI116087.
Rogers et al., Shwachman-Diamond syndrome. UpToDate. 2018. https://www.uptodate.com/contents/shwachman-diamond-syndrome/print .
Suragani et al. Ace-1332 (TGFbeta ligand trap) inhibits elevated TGFB1 signaling and reduces fibrosis in a murine model of myelofibrosis. Poster #P288, EHA 2016. 2 pages.
Suragani, Murine TGFbeta-antagonist (RAP-1332) Inhibits Fibrosis in a Murine Model of Myelofibrosis. Retrieved from Acceleronpharma.com on May 3, 2021. 18 pages.
Suzuki et al., Soluble type II transforming growth factor-beta receptor inhibits established murine malignant mesothelioma tumor growth by augmenting host antitumor immunity. Clin Cancer Res. Sep. 1, 2004;10(17):5907-18.
Tatusova et al., BLAST 2 Sequences, a new tool for comparing protein and nucleotide sequences. FEMS Microbiol Lett. May 15, 1999;174(2):247-50. doi: 10.1111/j.1574-6968.1999.tb13575.x.

(56) References Cited

OTHER PUBLICATIONS

Todd et al., Permanent alveolar collapse is the predominant mechanism in idiopathic pulmonary fibrosis. Expert Rev Respir Med. Aug. 2015;9(4):411-8. doi: 10.1586/17476348.2015.1067609.

Ueda et al. Systemic inhibition of transforming growth factor-beta in glioma-bearing mice improves the therapeutic efficacy of glioma-associated antigen peptide vaccines. Clin Cancer Res 2009;15:6551-9.

Vannucchi et al., A pathobiologic pathway linking thrombopoietin, GATA-1, and TGF-beta 1 in the development of myelofibrosis. Blood. May 1, 2005;105(9):3493-501. Epub Jan. 21, 2005. doi: 10.1182/blood-2004-04-1320.

Varga et al., Systemic sclerosis: a prototypic multisystem fibrotic disorder. J Clin Invest. Mar. 2007;117(3):557-67. doi: 10.1172/JCI31139.

Varga et al., Antitransforming growth factor-beta therapy in fibrosis: recent progress and implications for systemic sclerosis. Curr Opin Rheumatol. Nov. 2008;20(6):720-8. doi: 10.1097/BOR.0b013e32830e48e8.

Varga et al., Transforming growth factor-beta in systemic sclerosis (scleroderma). Front Biosci (Schol Ed). Jun. 1, 2009;1(1):226-35. doi: 10.2741/s22.

Vincenti et al., A Phase 2, Double-Blind, Placebo-Controlled, Randomized Study of Fresolimumab in Patients With Steroid-Resistant Primary Focal Segmental Glomerulosclerosis. Kidney Int Rep. Apr. 7, 2017;2(5):800-810. doi: 10.1016/j.ekir.2017.03.011.

Wang et al., Quantitative analysis of growth factor production in the mechanism of fibrosis in agnogenic myeloid metaplasia. Exp Hematol. Dec. 2006;34(12):1617-23. doi: 10.1016/j.exphem.2006.07.004.

Wang et al., Exosome-Mediated miR-29 Transfer Reduces Muscle Atrophy and Kidney Fibrosis in Mice. Mol Ther. Mar. 6, 2019;27(3):571-583. Epub Jan. 18, 2019. doi: 10.1016/j.ymthe.2019.01.008.

Yang et al., Cetuximab-mediated tumor regression depends on innate and adaptive immune responses. Mol Ther. Jan. 2013;21(1):91-100. doi: 10.1038/mt.2012.184. Epub Sep. 18, 2012.

Zhang et al., TGF-β Inhibition Rescues Hematopoietic Stem Cell Defects and Bone Marrow Failure in Fanconi Anemia. Cell Stem Cell. May 5, 2016;18(5):668-81. Epub Mar. 24, 2016. doi: 10.1016/j.stem.2016.03.002.

JP 2019-547490, Jan. 11, 2022, Office Action with English Translation.

JP 2019-547490, Jul. 26, 2022, Office Action with English Translation.

PCT/CA2021/050795, Sep. 7, 2021, International Search Report and Written Opinion.

PCT/IB2016/055204, Dec. 20, 2016, International Search Report and Written Opinion.

PCT/IB2016/055204, Mar. 15, 2018, International Preliminary Report on Patentability.

PCT/IB2018/051320, Sep. 12, 2019, International Preliminary Report on Patentability.

PCT/US2022/034671, Nov. 22, 2022, International Search Report and Written Opinion.

PCT/US2022/034677, Nov. 1, 2022, International Search Report and Written Opinion.

* cited by examiner

A

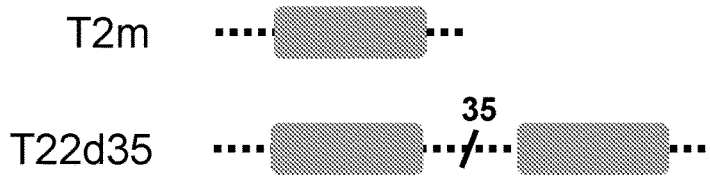

T2m

T22d35    35

▨ TβRII-ECD structured domain
···· Natural linker or sequence
/ Fusion of natural sequence
35 Length natural sequence

B

T2m
SEQ ID NO 1

IPPHVQKSVNNDMIVTDNNGAVKFPQLCKFCDVRFSTCDNQKSCM
SNCSITSICEKPQEVCVAVWRKNDENITLETVCHDPKLPYHDFILED
AASPKCIMKEKKKPGETFFMCSCSSDECNDNIIFSEEYNTSNPD

T22d35
SEQ ID NO 5

IPPHVQKSVNNDMIVTDNNGAVKFPQLCKFCDVRFSTCDNQKSCM
SNCSITSICEKPQEVCVAVWRKNDENITLETVCHDPKLPYHDFILED
AASPKCIMKEKKKPGETFFMCSCSSDECNDNIIFSEEYNTSNPDIP
PHVQKSVNNDMIVTDNNGAVKFPQLCKFCDVRFSTCDNQKSCMS
NCSITSICEKPQEVCVAVWRKNDENITLETVCHDPKLPYHDFILED
AASPKCIMKEKKKPGETFFMCSCSSDECNDNIIFSEEYNTSNPD

FIG. 1A/B

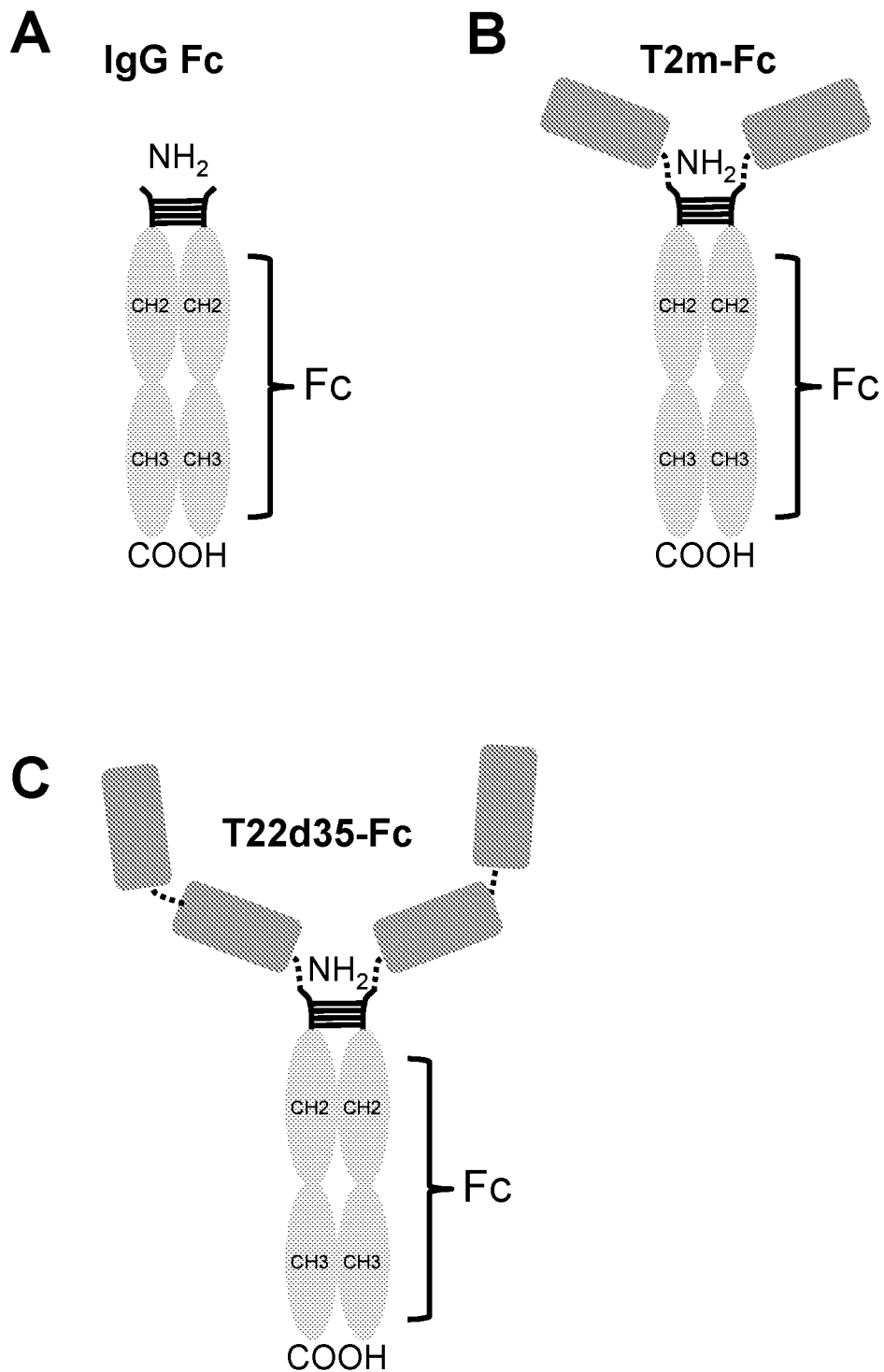
FIG. 2A/B/C

D

| | |
|---|---|
| T2m-Fc<br>SEQ ID NO 9 | <u>IPPHVQKSVNNDMIVTDNNGAVKFP</u>QLCKFCDVRFSTCDNQKSCMSNCS ITSICEKPQEVCVAVWRKNDENITLETVCHDPKLPYHDFILEDAASPKCIM KEKKKPGETFFMCSCSSDECNDNIIF<u>SEEYNTSNPD</u>*ERKCCVECPPCPA PPVAGPSVFLFPPKPKDTLMISRTPEVTCVVVDVSHEDPEVQFNWYVDG VEVHNAKTKPREEQFNSTFRVVSVLTVVHQDWLNGKEYKCKVSNKGLP APIEKTISKTKGQPREPQVYTLPPSREEMTKNQVSLTCLVKGFYPSDISV EWESNGQPENNYKTTPPMLDSDGSFFLYSKLTVDKSRWQQGNVFSCS VMHEALHNHYTQKSLSLSPG* |
| T22d35-Fc<br>SEQ ID NO 10 | <u>IPPHVQKSVNNDMIVTDNNGAVKFP</u>QLCKFCDVRFSTCDNQKSCMSNCS ITSICEKPQEVCVAVWRKNDENITLETVCHDPKLPYHDFILEDAASPKCIM KEKKKPGETFFMCSCSSDECNDNIIF<u>SEEYNTSNPD</u>IPPHVQKSVNNDMI VTDNNGAVKFPQLCKFCDVRFSTCDNQKSCMSNCSITSICEKPQEVCVA VWRKNDENITLETVCHDPKLPYHDFILEDAASPKCIMKEKKKPGETFFM CSCSSDECNDNIIF<u>SEEYNTSNPD</u>*ERKCCVECPPCPAPPVAGPSVFLFPP KPKDTLMISRTPEVTCVVVDVSHEDPEVQFNWYVDGVEVHNAKTKPRE EQFNSTFRVVSVLTVVHQDWLNGKEYKCKVSNKGLPAPIEKTISKTKGQ PREPQVYTLPPSREEMTKNQVSLTCLVKGFYPSDISVEWESNGQPENN YKTTPPMLDSDGSFFLYSKLTVDKSRWQQGNVFSCSVMHEALHNHYTQ KSLSLSPG* |

FIG. 2D

```
T22d35-Fc  linker        (SEQ ID NO 13)    SEEYNTSNPD.......ERKCCVECPPCPAPP
T22d35-Fc-IgG2-v2(CC)    (SEQ ID NO 25)    SEEYNTSNPD............VECPPCPAPP
T22d35-Fc-IgG1-v1(CC)    (SEQ ID NO 16)    SEEYNTSNPD...........THTCPPCPAPE
T22d35-Fc-IgG1-v2(SCC)   (SEQ ID NO 19)    SEEYNTSNPD...VEPKSSDKTHTCPPCPAPE
T22d35-Fc-IgG1-v3(GSL-CC) (SEQ ID NO 22)   SEEYNTSNPDGGGSGGGSGGGTHTCPPCPAPE
```

FIG. 2E

| | |
|---|---|
| T22d35-Fc-IgG1-v1 (CC) SEQ ID NO 14 | <u>IPPHVQKSVNNDMIVTDNNGAVKFP</u>QLCKFCDVRFSTCDNQKSCMSNC SITSICEKPQEVCVAVWRKNDENITLETVCHDPKLPYHDFILEDAASPKC IMKEKKKPGETFFMCSCSSDECNDNIIF<u>SEEYNTSNPDIPPHVQKSVNN DMIVTDNNGAVKFP</u>QLCKFCDVRFSTCDNQKSCMSNCSITSICEKPQEV CVAVWRKNDENITLETVCHDPKLPYHDFILEDAASPKCIMKEKKKPGET FFMCSCSSDECNDNIIF<u>SEEYNTSNPD</u>*THTCPPCPAPELLGGPSVFLFP PKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK GQPREPQVYTLPPSRDELTKNQVSLTCLVKGFYPSDIAVEWESNGQPE NNYKTTPPVLDSDGSFFLYSKLTVDKSRWQQGNVFSCSVMHEALHNH YTQKSLSLSPG* |
| T22d35-Fc-IgG1-v2 (SCC) SEQ ID NO 17 | <u>IPPHVQKSVNNDMIVTDNNGAVKFP</u>QLCKFCDVRFSTCDNQKSCMSNC SITSICEKPQEVCVAVWRKNDENITLETVCHDPKLPYHDFILEDAASPKC IMKEKKKPGETFFMCSCSSDECNDNIIF<u>SEEYNTSNPDIPPHVQKSVNN DMIVTDNNGAVKFP</u>QLCKFCDVRFSTCDNQKSCMSNCSITSICEKPQEV CVAVWRKNDENITLETVCHDPKLPYHDFILEDAASPKCIMKEKKKPGET FFMCSCSSDECNDNIIF<u>SEEYNTSNPD</u>*VEPKSSDKTHTCPPCPAPELLG GPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVM HEALHNHYTQKSLSLSPG* |
| T22d35-Fc-IgG1-v3 (GSL-CC) SEQ ID NO 20 | <u>IPPHVQKSVNNDMIVTDNNGAVKFP</u>QLCKFCDVRFSTCDNQKSCMSNC SITSICEKPQEVCVAVWRKNDENITLETVCHDPKLPYHDFILEDAASPKC IMKEKKKPGETFFMCSCSSDECNDNIIF<u>SEEYNTSNPDIPPHVQKSVNN DMIVTDNNGAVKFP</u>QLCKFCDVRFSTCDNQKSCMSNCSITSICEKPQEV CVAVWRKNDENITLETVCHDPKLPYHDFILEDAASPKCIMKEKKKPGET FFMCSCSSDECNDNIIF<u>SEEYNTSNPDGGGSGGGSGGG</u>*THTCPPCPAP ELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDI AVEWESNGQPENNYKTTPPVLDSDGSFFLYSKLTVDKSRWQQGNVFS CSVMHEALHNHYTQKSLSLSPG* |

FIG. 2F

T22d35-Fc-IgG2-v2 (CC)
SEQ ID NO 23

<u>IPPHVQKSVNNDMIVTDNNGAVKFP</u>QLCKFCDVRFSTCDNQKSCMSNC
SITSICEKPQEVCVAVWRKNDENITLETVCHDPKLPYHDFILEDAASPKC
IMKEKKKPGETFFMCSCSSDECNDNIIF<u>SEEYNTSNPDIPPHVQKSVNN
DMIVTDNNGAVKFP</u>QLCKFCDVRFSTCDNQKSCMSNCSITSICEKPQEV
CVAVWRKNDENITLETVCHDPKLPYHDFILEDAASPKCIMKEKKKPGET
FFMCSCSSDECNDNIIF<u>SEEYNTSNPD</u>*VECPPCPAPPVAGPSVFLFPPK
PKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQ
PREPQVYTLPPSREEMTKNQVSLTCLVKGFYPSDISVEWESNGQPENN
YKTTPPMLDSDGSFFLYSKLTVDKSRWQQGNVFSCSVMHEALHNHYT
QKSLSLSPG*

FIG. 2G

A
SEC elution profile T2m-Fc
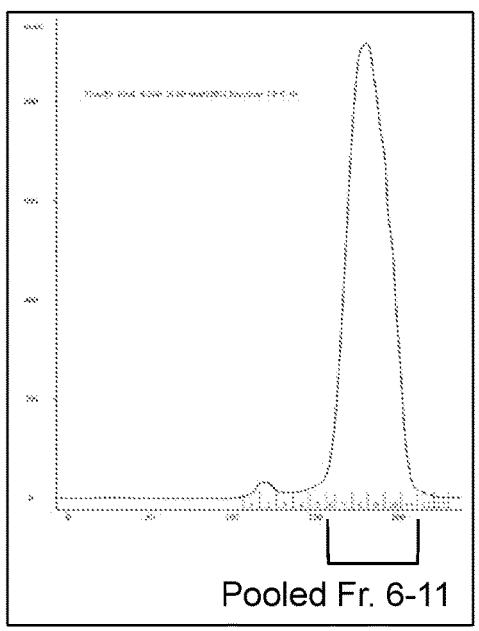
Pooled Fr. 6-11
B
UPLC-SEC profile after SEC purification
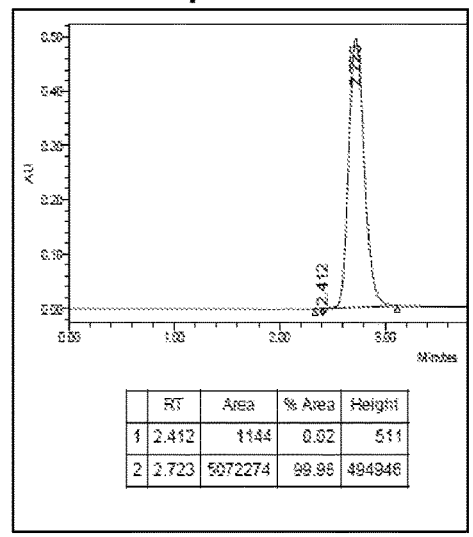
C
SDS-PAGE
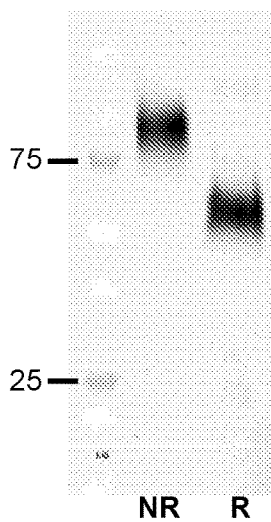
FIG. 3A/B/C

A
SEC elution profile T22d35-Fc
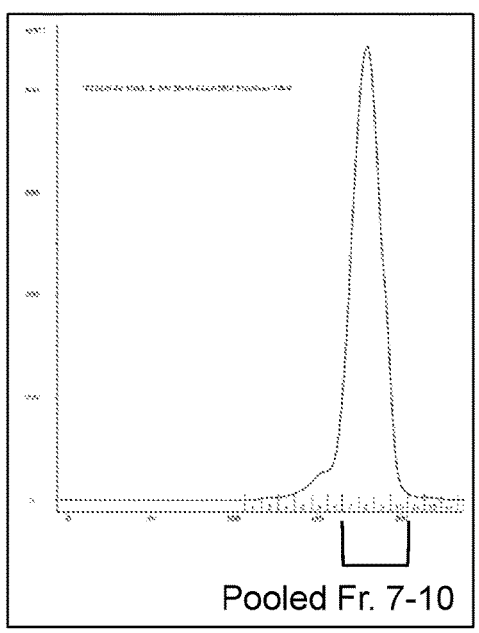
Pooled Fr. 7-10
B
UPLC-SEC profile after SEC purification
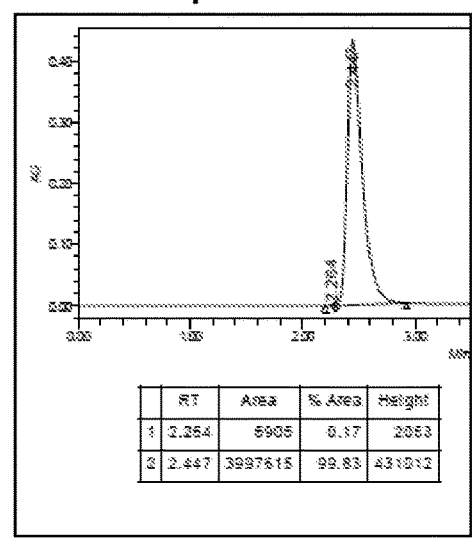
C SDS-PAGE
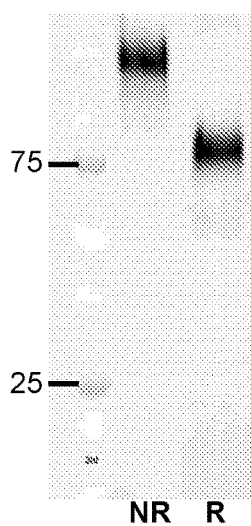
FIG. 4A/B/C

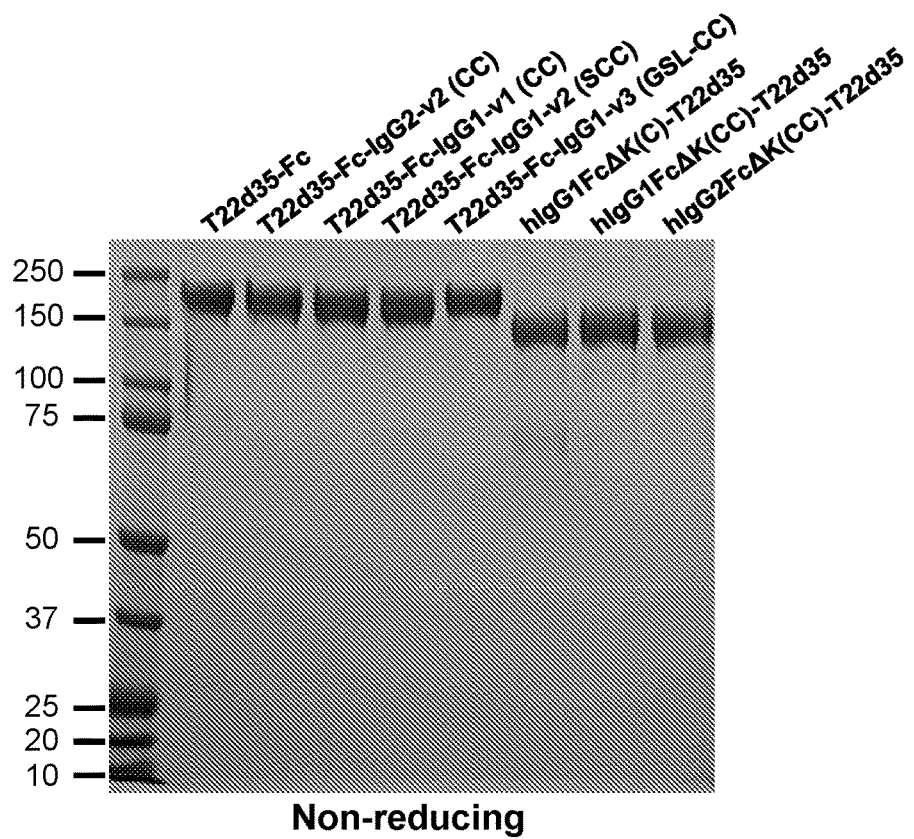
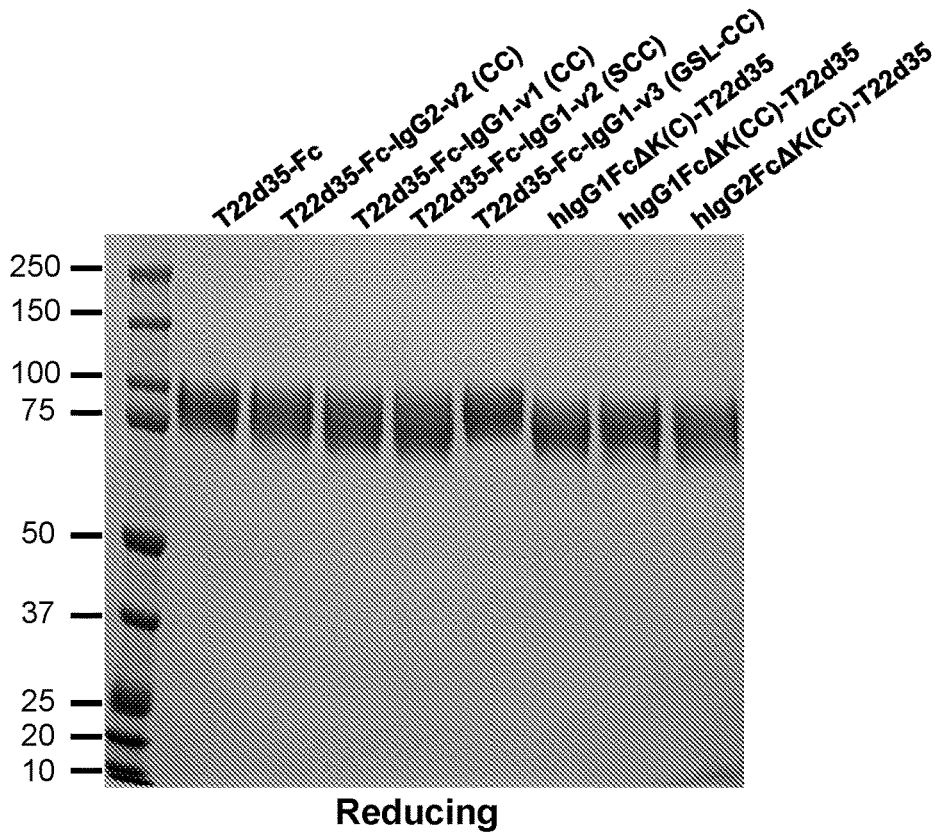
FIG. 5A/B

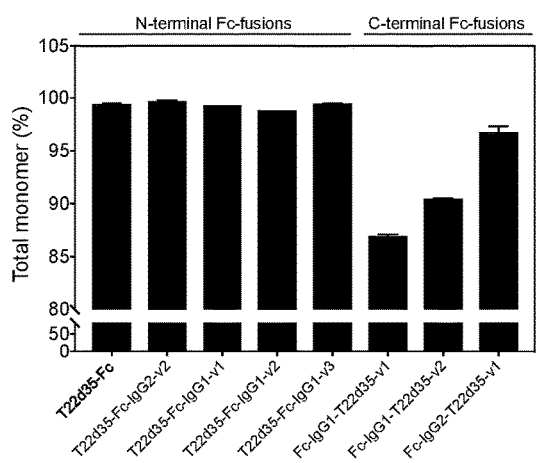
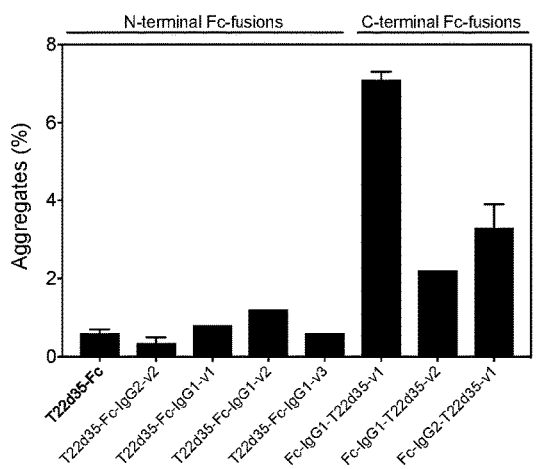
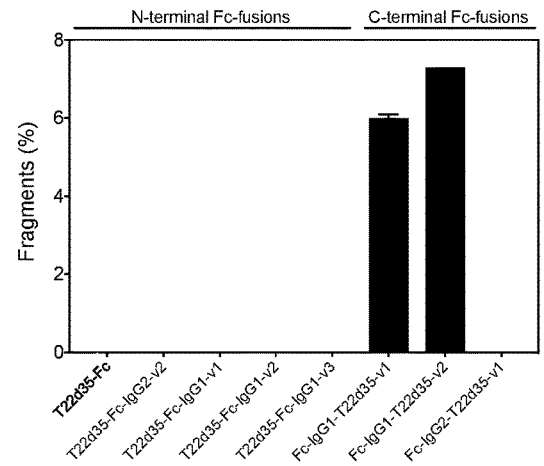
FIG. 6A/B/C

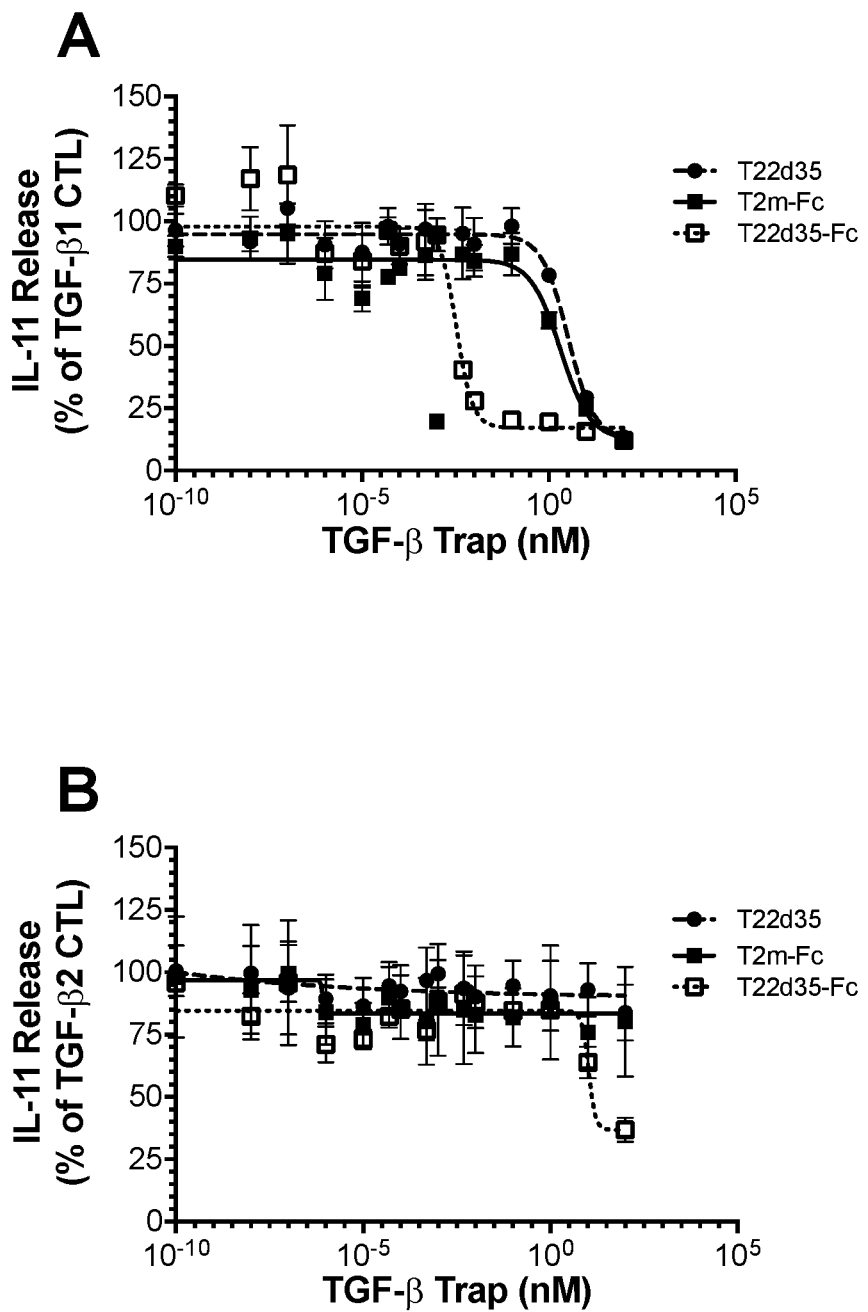
FIG. 7A/B

|  |  | T22d35 | T2m-Fc | T22d35-Fc |
|---|---|---|---|---|
| TGF-β1 | IC50 (nM) | 3.253 | 2.059 | 0.003348 |
|  | Fold Change T2m-Fc | 0.63x | 1x | 615x |
|  | Fold Change T22d35 | 1x | 1.58x | 972x |

|  |  | T22d35 | T2m-Fc | T22d35-Fc |
|---|---|---|---|---|
| TGF-β2 | IC50 (nM) | No neutralization | No neutralization | ~ 10 |
|  | Fold Change T2m-Fc | NA | NA | NA |
|  | Fold Change T22d35 | NA | NA | NA |

|  |  | T22d35 | T2m-Fc | T22d35-Fc |
|---|---|---|---|---|
| TGF-β3 | IC50 (nM) | 0.9491 | 0.0943 | 0.003908 |
|  | Fold Change T2m-Fc | 0.099x | 1x | 24x |
|  | Fold Change T22d35 | 1x | 10x | 243x |

| N-terminal Fc-fused T22d35 | IC50 (nM) | TGF-β1 | | | | |
|---|---|---|---|---|---|---|
| | | T22d35-Fc | T22d35-Fc-IgG2-v2 (CC) | T22d35-Fc-IgG1-v1 (CC) | T22d35-Fc-IgG1-v2 (SCC) | T22d35-Fc-IgG1-v3 (GSL-CC) |
| | | 0.002863 | 0.002783 | 0.002345 | 0.002128 | 0.002476 |

| C-terminal Fc-fused T22d35 | IC50 (nM) | TGF-β1 | | |
|---|---|---|---|---|
| | | hIgG1FcΔK(C)-T22d35 | hIgG1FcΔK(CC)-T22d35 | hIgG2FcΔK(CC)-T22d35 |
| | | 0.002926 | 0.003027 | 0.002487 |

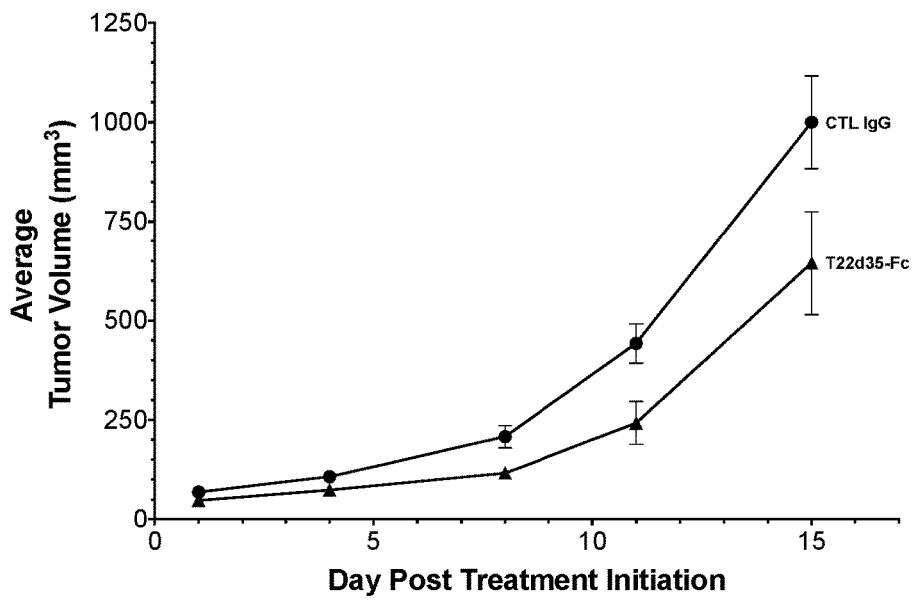
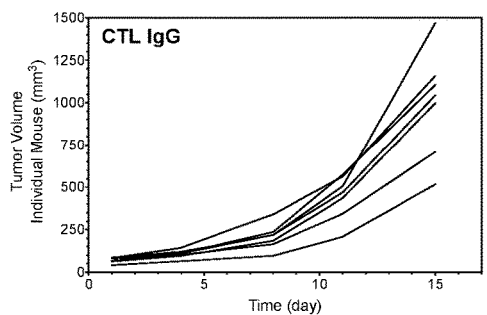
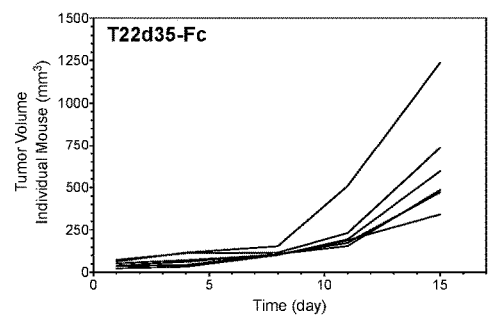
| | Comparison | Mean Diff. | 95.00% CI of diff. | Significant? | Adjusted P Value |
|---|---|---|---|---|---|
| Day 15 | CTL IgG vs. T22d35-Fc | 355.5 | 91.42 to 619.5 | *** | 0.0006 |
FIG. 10

TGF-β-RECEPTOR ECTODOMAIN FUSION MOLECULES AND USES THEREOF

CROSS-REFERENCE TO RELATED APPLICATIONS

This application is a U.S. National Stage Application under 35 U.S.C. § 371 of International Application No. PCT/IB2018/051320, filed Mar. 1, 2018, which claims priority to U.S. Provisional Application No. 62/465,969, filed Mar. 2, 2017 and U.S. Provisional Application No. 62/468,586, filed Mar. 8, 2017, the entire contents of each of which are hereby incorporated by reference in their entireties.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 20, 2022, is named A089970017US00-SUBSEQ-LJG and is 70,760 bytes in size.

FIELD OF THE INVENTION

The present invention relates to TGF-β receptor ectodomain fusion molecules and uses thereof. More specifically, the present invention relates to TGF-β superfamily receptor ectodomain fusion molecules and their use in TGF-β ligand neutralization.

BACKGROUND OF THE INVENTION

TGF-β is part of a superfamily of over 30 ligands that regulate several physiological processes, including cell proliferation, migration and differentiation. Perturbation of their levels and/or signaling gives rise to significant pathological effects. For instance, TGF-β and activin ligands play critical pathogenic roles in many diseases including cancer (Hawinkels & Ten Dijke, 2011; Massague et al, 2000; Rodgarkia-Dara et al, 2006). TGF-β, in particular, is considered as a critical regulator of tumor progression and is overexpressed by most tumor types. It favors tumorigenesis in part by inducing an epithelial-mesenchymal transition (EMT) in the epithelial tumor cells, leading to aggressive metastasis (Thiery et al, 2009). TGF-β also promotes tumorigenesis by acting as a powerful suppressor of the immune response in the tumor microenvironment (Li et al, 2006). In fact, TGF-β is recognized as one of the most potent immunosuppressive factors present in the tumor microenvironment. TGF-β interferes with the differentiation, proliferation and survival of many immune cell types, including dendritic cells, macrophages, NK cells, neutrophils, B-cells and T-cells; thus, it modulates both innate and adaptive immunity (Santarpia et al, 2015; Yang et al, 2010). The importance of TGF-β in the tumor microenvironment is highlighted by evidence showing that, in several tumor types (including melanoma, lung, pancreatic, colorectal, hepatic and breast), elevated levels of TGF-β ligand are correlated with disease progression and recurrence, metastasis, and mortality. Hence, significant effort has been invested in devising anti-tumor therapeutic approaches that involve TGF-β inhibition (Arteaga, 2006; Mourskaia et al, 2007; Wojtowicz-Praga, 2003). These approaches include the use of polypeptide fusions based on the TGF-β receptor ectodomain that binds or "traps" the TGF-β ligand (see WO01/83525; WO2005/028517; WO2008/113185; WO2008/157367; WO2010/003118; WO2010/099219; WO2012/071649; WO2012/142515; WO2013/000234; U.S. Pat. No. 5,693,607; US2005/0203022; US2007/0244042; U.S. Pat. Nos. 8,318,135; 8,658,135; 8,815,247; US2015/0225483; and US2015/0056199).

One approach to developing therapeutic agents that inhibit TGF-β function has been to use antibodies or soluble decoy receptors (also termed receptor ectodomain (ECD)-based ligand traps) to bind and sequester ligand, thereby blocking access of ligand to its cell surface receptors (Zwaagstra et al, 2012). In general, receptor ECD-based traps are a class of therapeutic agents that are able to sequester a wide range of ligands and that can be optimized using protein-engineering approaches (Economides et al, 2003; Holash et al, 2002; Jin et al, 2009).

Previously, a novel protein engineering design strategy was used to generate single-chain, bivalent TGF-3 Type II receptor ectodomain (TβRII-ECD) traps that are able to potently neutralize members of the TGF-β superfamily of ligands due to avidity effects (Zwaagstra et al, 2012) [WO 2008/113185; WO 2010/031168]. In this case, bivalency was achieved via covalent linkage of two TβRII ectodomains using regions of the intrinsically disordered regions (IDR) that flank the structured, ligand-binding domain of TβRII-ECD. An example of these single-chain bivalent traps, T22d35, exhibited TGF-β neutralization potencies ~100-fold higher than the monovalent non-engineered TβRII ectodomain, though the bivalent trap did not neutralize the TGF-β2 isotype and had a relatively short circulating half-life.

It would be useful to provide TβRII-ECD-based traps having improved properties, such as enhanced potency.

SUMMARY OF THE INVENTION

The present invention provides a polypeptide construct with enhanced potencies in inhibiting TGFβ.

A polypeptide construct of the present invention comprises a first region and a second region, wherein the first region comprises a first and/or second TGFβ receptor ectodomain (ECD); and wherein the second region comprises the second constant domain ($C_H2$) and/or third constant domain ($C_H3$) of an antibody heavy chain. In a preferred non-limiting embodiment, the C-terminus of the first region is linked to the N-terminus of the second region. In a preferred non-limiting embodiment, the first region of the polypeptide construct comprises a first TβRII-ECD (ECD1) and/or a second TβRII-ECD (ECD2), wherein ECD1 and ECD2 are linked in tandem.

The polypeptide construct provided, wherein the first region comprises a (TβRII-ECD)-(TβRII-ECD) doublet linked at its C-terminus with an antibody constant domain inhibits TGFβ activity with at least 600-fold more potency than a counterpart construct having a single TβRII-ECD linked at its C-terminus with an antibody constant domain (i.e when a second ECD is absent, also referred to herein as a singlet).

The polypeptide construct provided comprises a second, TGFβ receptor ectodomain ECD that is linked in tandem to the first ECD, wherein the polypeptide construct (i.e. an ECD doublet construct) linked to an antibody constant domain exhibits TGFβ neutralization (inhibits) that is at least 100, 200, 300, 400, 500, 600, 700, 800 or 900-fold greater than a counterpart construct in which the antibody constant domain is absent, (i.e. an ECD doublet construct, also referred to herein as a non-Fc fused doublet).

In connection with the TβRII-ECDs and the potency with which they inhibit TGF-β activity, it has been found that surprisingly enhanced potencies can result from careful selection of their constituents. This occurs when certain TβRII-ECDs are linked in tandem, and the C-terminus thereof is linked to the N-terminus of an antibody constant domain (Fc). When in their fused and dimeric form, comprising two such polypeptides cross-linked via cysteine bridging between the constant domain/s of each polypeptide, the resulting so-called "Fc fusions" having two TβRII-ECDs (an ECD "doublet") on each of the two "arms" can exhibit an inhibiting activity that is over 600-fold greater for TGF-β1, and over 20-fold greater for TGF-β3, as compared to "Fc fusions" having one ectodomain on each of the two "arms", as demonstrated by the inhibition of TGF-β1 and -β3-induced IL-11 secretion by human non-small cell lung cancer (NSCLC) A549 cells, among others. The potency enhancement is evident, relative to counterparts that either lack the Fc region or that lack a second ECD (i.e. are an ECD "singlet"). The potency enhancement is at least 100, 200, 300, 400, 500, or 600-fold greater for the Fc-fused doublet over the Fc-fused singlet. The potency enhancement is at least 100, 200, 300, 400, 500, 600, 700, 800, 900-fold and approximately 1000-fold greater for the Fc-fused doublet over the non-Fc doublet. The potency enhancement is evident, relative to counterparts that either lack the Fc region (the Fc-fused doublet T22d35-Fc is 972- and 243-fold better for TGF-β1 and TGF-β3, respectively than the non-Fc doublet), or that lack a second ECD (an ECD "singlet"; the Fc-fused doublet T22d35-Fc is 615- and 24-fold better for TGF-β1 and TGF-β3, respectively than the non-Fc doublet). More specifically, the Fc-doublet (T22d35-Fc) exhibits a potency enhancement that is at least 970-fold greater for TGF-β1 and at least 240-fold greater for TGF-β3 when compared to a non-Fc fused ECD doublet. Moreover, the Fc-doublet (T22d35-Fc) exhibits a potency enhancement that is at least 600-fold greater for TGF-β1 and over 20-fold greater for TGF-β3 when compared to an Fc-singlet (T2m-Fc).

In a general aspect, there is provided a polypeptide construct comprising at least two TβRII-ECDs linked in tandem (i.e. ECD doublet), and an antibody constant domain comprising at least, the second constant domain ($C_H2$) and/or third constant domain ($C_H3$) of an antibody heavy chain, wherein the C-terminus of the ectodomains is linked to the N-terminus of the antibody constant domain. In this form, the construct is a single chain polypeptide. Thus, the antibody constant domain may comprise only the $C_H2$ domain, or it may comprise the $C_H2$ domain and the $C_H3$ domain.

In embodiments the polypeptides are provided as dimeric fusion polypeptides comprising two single chain polypeptides and cross-linking means coupling the chains covalently.

In other embodiments, the two ectodomains are the same, in terms of their binding targets generally and/or their target species.

In a preferred embodiment, the first region comprises two TGF-β receptor ectodomains (TGFβR-ECD or 'TβR-ECD'). In a preferred embodiment, the TβR-ECD is a TGF-β receptor type II ectodomain (TβRII-ECD). In a preferred embodiment, the TβR-ECD comprises SEQ ID NO:1, and a sequence substantially identical thereto.

The second region may comprise a sequence selected from the group consisting of SEQ ID NO:12, SEQ ID NO:15, SEQ ID NO:18, SEQ ID NO:24, and a sequence substantially identical thereto.

In a preferred embodiment, the second region of a polypeptide construct of the present invention can further comprise a $C_H1$. In embodiments, the constructs are monofunctional.

The polypeptide constructs of the present invention exploit an antibody heavy chain of human origin. In a preferred embodiment, the antibody heavy chain is selected from the group consisting of a human IgG1 (SEQ ID NO:15) and IgG2 (SEQ ID NO:24).

Thus, in another aspect, there is provided a polypeptide construct according to the present invention wherein the construct is a dimeric polypeptide; wherein the dimeric polypeptide comprises:

(i) a first single chain polypeptide comprising a second region comprising the second constant domain ($C_H2$) and third constant domain ($C_H3$) of an antibody heavy chain, and a first region comprising two TGF-β receptor ectodomains (TβRII-ECD), wherein the C-terminus of the first region is linked to the N-terminus of the second region, and (ii) a second single chain polypeptide comprising a second region comprising the second constant domain ($C_H2$) and third constant domain ($C_H3$) of an antibody heavy chain, and a first region comprising two TGF-β receptor ectodomains (TβRII-ECD) linked in tandem, wherein the C-terminus of the first region is linked to the N-terminus of the second region, and the first single chain polypeptide is cross-linked with the second single chain polypeptide.

There is also provided a nucleic acid molecule encoding any polypeptide construct of the present invention. There is also provided a vector comprising the nucleic acid molecule of the present invention.

There is also provided a composition comprising one or more than one independently selected polypeptide constructs of the present invention and a pharmaceutically-acceptable carrier, diluent, or excipient.

There is also provided a transgenic cellular host comprising a nucleic acid molecule or a vector of the present invention. The transgenic cellular host can further comprise a second nucleic acid molecule or a second vector encoding a second polypeptide construct when that second polypeptide construct is the same or different from the first polypeptide construct. The second nucleic acid molecule or second vector is present necessarily when the two polypeptide constructs are different (heterodimeric), but are not necessary when the constructs are the same (homodimeric).

There is also provided the use of a polypeptide construct according to the present invention for treatment of a medical condition, disease or disorder; wherein the medical condition, disease or disorder comprises, but is not limited to, cancer, ocular diseases, fibrotic diseases, or genetic disorders of connective tissue and immune disorders.

The polypeptide construct of the present invention may comprise a $C_H2$ and $C_H3$ or only a $C_H2$ from an antibody heavy chain that is of human origin. For example, and without wishing to be limiting, the antibody heavy chain may be selected from the group consisting of a human IgG1 and IgG2. In embodiments, the constant domain in the constructs is $C_H2$ per se, or $C_H3$ per se or $C_H2$-$C_H3$. Suitably, the antibody heavy chain component provides for disulfide crosslinking between single chain polypeptide constructs that are the same or different. Also suitably, the antibody heavy chain provides for protein A-based isolation of the dimeric polypeptide that is produced by the host cells.

In embodiments the receptor ectodomain region comprises two independently selected ectodomains that are linked in tandem, i.e., in a linear manner. In some embodiments, the ectodomains are the same in sequence, or least the same with respect to their target ligand.

The present invention also provides a nucleic acid molecule encoding the polypeptide constructs as described herein. A vector comprising the nucleic acid molecule just described is also encompassed by the invention. The invention also includes a transgenic cellular host comprising the nucleic acid molecule or a vector as described herein; the cellular host may further include a second nucleic acid molecule or a second vector encoding a second polypeptide construct different from the first polypeptide construct. Systems used to produce the present polypeptides can be secretion systems, particularly in the case where dimerization through disulfide bridges is required, and the expression polynucleotides thus encode secretion signals that are cleaved by the host upon secretion into the culturing medium.

Compositions comprising one or more than one independently selected polypeptide construct described herein and a pharmaceutically-acceptable carrier, diluent, or excipient are also encompassed by the present invention.

These and other features of the invention will now be described by way of example, with reference to the appended drawings, wherein:

BRIEF DESCRIPTION OF THE DRAWINGS

FIG. 1 A/B is a schematic drawing of the of the TGF-β Type II receptor ectodomain (TβRII-ECD; also abbreviated as T2m) and the single chain fusion of two T2m domains (also abbreviated T22d35) (FIG. 1A); FIG. 1B provides the corresponding amino acid sequences, wherein the natural linker sequences (SEQ ID NO:6, SEQ ID NO:7, SEQ ID NO:8) are underlined and the sequence of the TβRII structured domain (SEQ ID NO:4) is shown in bold.

FIG. 2 A-G, where FIG. 2A/B/C is a schematic representation of the fusion of the T2m and T22d35 modules to the N-termini of the heavy chains of an IgG2 Fc region (2A) in order to generate fusion proteins T2m-Fc (2B) and T22d35-Fc (2C); FIG. 2D provides the amino acid sequence of the T2m-Fc and T22d35-Fc fusion proteins (SEQ ID NO:9, SEQ ID NO:10). FIG. 2E provides aligned sequenced of additional variants of the linker region between the Fc and ECD region in the T22d35-Fc fusions. FIGS. 2F and 2G provide the amino acid sequence of the T22d35-Fc linker variants using a human IgG1 Fc (FIG. 2F; SEQ ID NO: 14, SEQ ID NO:17, SEQ ID NO:20) and a human IgG2 Fc region (FIG. 2G; SEQ ID NO:23). The natural linker sequences (SEQ ID NO:6, SEQ ID NO:7, SEQ ID NO:8) are underlined, the sequence of the TβRII structured domain (SEQ ID NO:4) is shown in bold and the human IgG Fc sequence variants (SEQ ID NO:12, SEQ ID NO:15, SEQ ID NO:18, SEQ ID NO:24) are shown in bold-italics.

FIG. 3 A/B/C shows the preparative SEC elution profile for the T2m-Fc fusion protein (3A); Fractions (Fr.) 6-11 were pooled and concentrated. Protein integrity of the SEC purified material was then assessed by UPLC-SEC profile (3B) and SDS-PAGE assessment under non-reducing (NR) and reducing (R) conditions (3C).

FIG. 4 A/B/C shows the preparative SEC elution profile for the T22d35-Fc fusion protein (4A); Fr. 7-10 were pooled and concentrated. Protein integrity of the SEC purified material was then assessed by UPLC-SEC profile (4B) and SDS-PAGE assessment under non-reducing (NR) and reducing (R) conditions (4C).

FIG. 5 A/B provides SDS-PAGE analysis of the protein A purified T22d35-Fc, T22d35-Fc-IgG2-v2(CC), T22d35-Fc-IgG1-v1 (CC), T22d35-Fc-IgG1-v2(SCC), T22d35-Fc-IgG1-v3(GSL-CC), hIgG1 FcΔK(C)-T22d35, hIgG1 FcΔK (CC)-T22d35 and hIgG2FcΔK(CC)-T22d35 variants under non-reducing (A) and reducing (B) conditions.

FIG. 6 A/B/C provides the percentage of intact monomer (A), aggregates (B), and fragments (C) of the various fusion proteins, indicating that there are advantages to expressing the T22d35 doublet at the N-terminus of an IgG Fc portion. The table lists the numerical differences in the parameters that were analyzed.

FIG. 10 Functional in vivo evaluation of the T22d35-Fc fusion protein in a syngeneic MC-38 mouse colon carcinoma model. (A) Tumor volumes were calculated as described and plotted as average tumor values+/−SD per cohort. A two-way ANOVA was used to analyse whether statistically significant differences between the calculated average tumor volumes in the T22d35-Fc and CTL IgG treatment cohorts over the course of time. In addition, MC-38 tumor growth (calculated volume) was plotted per individual mouse for the CTL IgG (B) and T22d35-Fc treated cohorts (C).

Figure 7C:
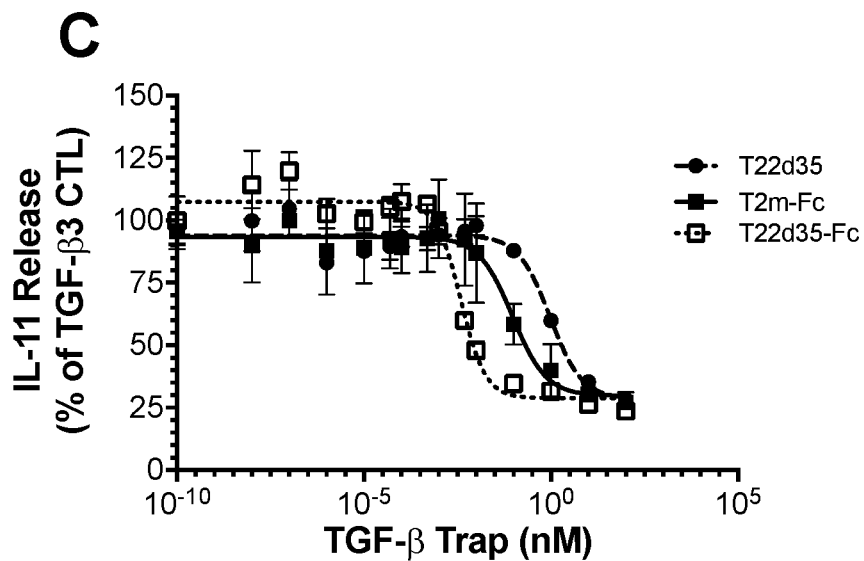
FIG. 7 A/B/C provides a functional evaluation of the T2m-Fc and T22d35-Fc fusion proteins compared to the non-Fc-fused single chain T22d35 trap in a A549 IL-11 release assay. Neutralization of TGF-β1 (5A), -β2 (5B), -β3 (5C) was assessed and calculated as a % of the TGF-β control (Average of a triplicate experiment+/−SD). The table lists the calculated $IC_{50}$ values calculated in Graphpad Prism (4-PL algorithm ((log (inhibitor) vs. response—variable slope (four parameters)).

Additional aspects and advantages of the present invention will be apparent in view of the following description. The detailed descriptions and examples, while indicating preferred embodiments of the invention, are given by way of illustration only, as various changes and modifications within the scope of the invention will become apparent to those skilled in the art

DETAILED DESCRIPTION OF THE INVENTION

There are now provided polypeptide constructs that bind to and neutralize all transforming growth factor beta (TGF-β1, 32 and β3) isoforms. These polypeptides exploit the TGF-β receptor ectodomains to trap or sequester various TGFβ species including TGF-β1 and TGF-β3, and to some extend TGF-β2. The potency with which the present polypeptide constructs neutralize TGF-β1 and -β3 is surprisingly far greater than related constructs, as demonstrated herein. For this reason, the present constructs are expected to be especially useful as pharmaceuticals for the treatment of medical indications such as cancer, fibrotic diseases and certain immune disorders.

The present polypeptide constructs comprise two TβR-ECDs, such as TβRII-ECDs, that are linked in tandem (C-terminus to N-terminus) and further comprise an antibody constant domain that comprises at least the second constant domain ($C_H2$) and/or third constant domain ($C_H3$) of an antibody heavy chain. The antibody constant domain (Fc) is coupled at its N-terminus to the C-terminus of the ectodomain. Having the ectodomain as a doublet, and having that doublet coupled to the N-terminus of the antibody constant domain, provides a "trap" with an enhanced the neutralization potency by a factor of 615 for TGFβ1 and a factor 24 for TGFβ3 compared to the construct having a single ECD coupled to the N-terminus of the antibody constant domain.

As used herein, the term TβRII-ECD refers to the extracellular region of the TGF-β Type II receptor that binds to the TGF-β ligand. In a preferred embodiment of the present constructs, the TGFβRII ectodomain is the ectodomain of the TGFβR species (i.e. TβRII-ECD) comprising the sequence that forms a stable three-dimensional folded structure:

(SEQ ID NO: 4)
QLCKFCDVRFSTCDNQKSCMSNCSITSICEKPQEVCVAVWRKNDENITLE

TVCHDPKLPYHDFILEDAASPKCIMKEKKKPGETFFMCSCSSDECNDNII

F.

In a related form that comprises flexible natural flanking sequence, the ECD can include the underlined structures, as shown below:

(SEQ ID NO: 1)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD

This sequence binds to the TGF-β ligand isotypes designated TGF-β1 and TGF-β3. Binding affinity for TGF-β2 is less.

In the present polypeptide constructs, the two TβRII-ECDs may comprise the same sequence. The two ectodomains are linked in tandem, wherein the result is a linear polypeptide in which the C-terminus of one ectodomain is linked to the N-terminus of another ectodomain.

The two ectodomains can be linked by direct fusion such that additional amino acid residues are not introduced. Alternatively, additional amino acid residues can form a linker that couples the two receptor ectodomains in tandem. In the protein construct of the present invention, the first and second regions of the polypeptide construct of the present invention are also linked.

By the term "linked", it is meant that the two regions are covalently bonded. The chemical bond may be achieved by chemical reaction, or may be the product of recombinant expression of the two regions in a single polypeptide chain. In a specific, non-limiting example, the C-terminus of the first region is linked directly to the N-terminus of the second region, that is, no additional "linker" amino acids are present between the two regions. In the case where no linker is present, that is to say direct fusion of the two regions, there will be a direct link between the C-terminus of the full ectodomain and the N-terminus of the antibody constant regions $C_H2$-$C_H3$. For example, in fusing an Fc variant (SEQ ID NO:12, SEQ ID NO:15, SEQ ID NO:18, SEQ ID NO:24) to the SEQ ID NO:1 via the intrinsically disordered linker with SEQ ID NO:8, which is part of the TβRII-ECD having SEQ ID NO:1 (i.e., no additional "linker" amino acids added), one connects the aspartic acid at the last position of SEQ ID NO:1 to a glutamic acid, a threonine, a valine or a valine found at the first position of SEQ ID NO:12, SEQ ID NO:15, SEQ ID NO:18, or SEQ ID NO:24, respectively.

A common practice when producing fusion constructs is to introduce glycine or glycine-serine linkers (GSL) such as GGGGS (SEQ ID NO: 34) or [G4S]$_n$ (where n is 1, 2, 3, 4 or 5 or more, such as 10, 25 or 50)(SEQ ID NO: 34) between the fused components. As taught in the above paragraph, the polypeptide fusions of the present invention can be produced by direct linkage without use of any additional amino-acid sequence except those present in the Fc region and in the receptor ectodomain region. One thus can refrain from utilizing foreign sequences as linkers, providing an advantage due to their potential for undesired immunogenicity and their added molecular weight. Entropic factors are also a potential liability for glycine and glycine-serine linkers, which are highly flexible and may become partially restricted upon target binding, hence causing a loss of entropy unfavourable to binding affinity. Therefore, only the flexible, intrinsically disordered N-terminal regions of the TGFβRII-ECD were employed as natural linkers in embodiments of the present invention. However, the particular amino acid compositions and lengths of these intrinsically disordered linkers (e.g., SEQ ID NO:6, SEQ ID NO:7, SEQ ID NO:8) precluded accurate prediction of whether the resulting direct-fusion constructs will have the required geometry and favourable molecular interactions for correct binding to their intended dimeric ligands. In other embodiments, the fusion polypeptide may include a flexible artificial GSL, as exemplified in the construct in SEQ ID NO:20, where the GS linker with the SEQ ID NO:21 is introduced between the aspartic acid (D) at the last position of TβRII-ECD having SEQ ID NO:1 and the threonine (T) at the first position of the Fc region variant having SEQ ID NO:15.

The first and second regions of the polypeptide construct are, in embodiments, connected by natural intrinsically disordered polypeptide linkers selected from the group consisting of SEQ ID NO:8, 13, 16, 19, 25, and a sequence substantially identical thereto. In other embodiments, the regions of the polypeptide constructs are connected by flexible linkers selected from the group consisting of SEQ ID NO:21 and SEQ ID NO:22, and a sequence substantially identical thereto.

In this embodiment, one region of the present polypeptide constructs comprises a TβRII-ECD doublet comprising first and second receptor ectodomains linked in tandem by the natural intrinsically disordered polypeptide linker with SEQ ID NO: 6, and having amino acid sequence comprising:

(SEQ ID NO: 5)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDIPPHVQKSVNNDMI

VTDNNGAVKFPQLCKFCDVRFSTCDNQKSCMSNCSITSICEKPQEVCVAV

WRKNDENITLETVCHDPKLPYHDFILEDAASPKCIMKEKKKPGETFFMCS

CSSDECNDNIIFSEEYNTSNPD.

The present constructs also comprise a region that comprises an antibody constant domain that comprises at least the second constant domain ($C_H2$) and/or third constant domain ($C_H3$) of an antibody heavy chain. The antibody constant domain is coupled at its N-terminus to the C-terminus of the ectodomain doublet, so that the orientation of the construct is a single chain of TβRII-ECD(link)TβRII-ECD(link)$C_H2$-$C_H3$.

The antibody constant domain provides for cross-linking between two of the present polypeptide constructs. This is achieved when the expressed polypeptide constructs are secreted from their expression host. Thus, production of the single chain polypeptide provides the construct in a dimeric form in which the two constructs are cross-linked via disulfide bridges that involve one or more cysteine residues within each of the antibody constant domains present in each of the constructs.

The antibody constant domain present in the construct is desirably sourced from an IgG constant region, and especially from the constant domain of either IgG1 or IgG2.

The constructs provided are monofunctional in the sense that the constant region itself may have no particular activity, other than to act as a structure through which dimers of the polypeptide constructs can form. These minimal constant regions can also be altered to provide some benefit, by incorporating the corresponding hinge regions and optionally changing the cysteine residue composition. Thus, some or all of the cysteine residues involved in bridging the two Fc fragments or naturally used to bridge between the heavy and light chains of a full-length antibody can be replaced or deleted. One advantage of minimizing the number of cysteine residues is to reduce the propensity for disulphide bond scrambling, which could promote aggregation. For example, these cysteine residues and alteration thereof are seen in the natural or non-natural linker sequences located around the junction of the first and second regions of the polypeptide constructs and which are listed below:

SEEYNTSNPDTHTCPPCPAPE (SEQ ID NO:16), SEEYNTSNPDVEPKSSDKTHTCPPCPAPE (SEQ ID NO:19), SEEYNTSNPDGGGSGGGSGGGTH-TCPPCPAPE (SEQ ID NO:22) incorporating variations of human IgG1 hinge sequence; and SEEYNTSNPDERKCCVECPPCPAPP (SEQ ID NO:13) and SEEYNTSNPDVECPPCPAPP (SEQ ID NO:25) incorporating variations of human IgG2 hinge sequence; and a sequence substantially identical thereto.

Not all of the naturally-occurring inter-hinge disulfide bonds need to be formed for the Fc homodimerization to occur, while noting that the stability of the Fc homodimer may depend on the number of intermolecular disulphide bridges.

In the present disclosure, an "antibody", also referred to in the art as "immunoglobulin" (Ig), refers to a protein constructed from paired heavy and light polypeptide chains. The structure of an antibody and of each of the domains is well established and familiar to those of skill in the art, though is summarized herein. When an antibody is correctly folded, each chain folds into a number of distinct globular domains joined by more linear polypeptide sequences; the immunoglobulin light chain folds into a variable ($V_L$) and a constant ($C_L$) domain, while the heavy chain folds into a variable ($V_H$) and three constant ($C_H1$, $C_H2$, $C_H3$) domains. Once paired, interaction of the heavy and light chain variable domains ($V_H$ and $V_L$) and first constant domain ($C_L$ and $C_H1$) results in the formation of a Fab (Fragment, antigen-binding) containing the binding region (Fv); interaction of two heavy chains results in pairing of $C_H2$ and $C_H3$ domains, leading to the formation of a Fc (Fragment, crystallisable). Characteristics described herein for the $C_H2$ and $C_H3$ domains also apply to the Fc.

In the present invention and its specific embodiments, the polypeptide constructs that exhibit significantly enhanced potency comprise the following:

```
T22d35-Fc:
                                                      (SEQ ID NO: 10)
IPPHVQKSVNNDMIVTDNNGAVKFPQLCKFCDVRFSTCDNQKSCMSNCSITSICEKPQEVCVA

VWRKNDENITLETVCHDPKLPYHDFILEDAASPKCIMKEKKKPGETFFMCSCSSDECNDNIIFS

EEYNTSNPDIPPHVQKSVNNDMIVTDNNGAVKFPQLCKFCDVRFSTCDNQKSCMSNCSITSIC

EKPQEVCVAVWRKNDENITLETVCHDPKLPYHDFILEDAASPKCIMKEKKKPGETFFMCSCSS

DECNDNIIFSEEYNTSNPDERKCCVECPPCPAPPVAGPSVFLFPPKPKDTLMISRTPEVTCVV

VDVSHEDPEVQFNWYVDGVEVHNAKTKPREEQFNSTFRVVSVLTVVHQDWLNGKEYKCKVS

NKGLPAPIEKTISKTKGQPREPQVYTLPPSREEMTKNQVSLTCLVKGFYPSDISVEWESNGQP

ENNYKTTPPMLDSDGSFFLYSKLTVDKSRWQQGNVFSCSVMHEALHNHYTQKSLSLSPG

T22d35-Fc-IgG2-v2 (CC):
                                                      (SEQ ID NO: 23)
IPPHVQKSVNNDMIVTDNNGAVKFPQLCKFCDVRFSTCDNQKSCMSNCSITSICEKPQEVCVA

VWRKNDENITLETVCHDPKLPYHDFILEDAASPKCIMKEKKKPGETFFMCSCSSDECNDNIIFS

EEYNTSNPDIPPHVQKSVNNDMIVTDNNGAVKFPQLCKFCDVRFSTCDNQKSCMSNCSITSIC

EKPQEVCVAVWRKNDENITLETVCHDPKLPYHDFILEDAASPKCIMKEKKKPGETFFMCSCSS

DECNDNIIFSEEYNTSNPDVECPPCPAPPVAGPSVFLFPPKPKDTLMISRTPEVTCVVVDVSH

EDPEVQFNWYVDGVEVHNAKTKPREEQFNSTFRVVSVLTVVHQDWLNGKEYKCKVSNKGLP

APIEKTISKTKGQPREPQVYTLPPSREEMTKNQVSLTCLVKGFYPSDISVEWESNGQPENNYK

TTPPMLDSDGSFFLYSKLTVDKSRWQQGNVFSCSVMHEALHNHYTQKSLSLSPG
```

-continued

T22d35-Fc-IgG1-v1 (CC):
(SEQ ID NO: 14)
IPPHVQKSVNNDMIVTDNNGAVKFPQLCKFCDVRFSTCDNQKSCMSNCSITSICEKPQEVCVA

VWRKNDENITLETVCHDPKLPYHDFILEDAASPKCIMKEKKKPGETFFMCSCSSDECNDNIIFS

EEYNTSNPDIPPHVQKSVNNDMIVTDNNGAVKFPQLCKFCDVRFSTCDNQKSCMSNCSITSIC

EKPQEVCVAVWRKNDENITLETVCHDPKLPYHDFILEDAASPKCIMKEKKKPGETFFMCSCSS

DECNDNIIFSEEYNTSNPDTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLSLSPG

T22d35-Fc-IgG1-v2 (SCC):
(SEQ ID NO: 17)
IPPHVQKSVNNDMIVTDNNGAVKFPQLCKFCDVRFSTCDNQKSCMSNCSITSICEKPQEVCVA

VWRKNDENITLETVCHDPKLPYHDFILEDAASPKCIMKEKKKPGETFFMCSCSSDECNDNIIFS

EEYNTSNPDIPPHVQKSVNNDMIVTDNNGAVKFPQLCKFCDVRFSTCDNQKSCMSNCSITSIC

EKPQEVCVAVWRKNDENITLETVCHDPKLPYHDFILEDAASPKCIMKEKKKPGETFFMCSCSS

DECNDNIIFSEEYNTSNPDVEPKSSDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLS

PG;
and

T22d35-Fc-IgG1-v3 (GSL-CC):
(SEQ ID NO: 20)
IPPHVQKSVNNDMIVTDNNGAVKFPQLCKFCDVRFSTCDNQKSCMSNCSITSICEKPQEVCVA

VWRKNDENITLETVCHDPKLPYHDFILEDAASPKCIMKEKKKPGETFFMCSCSSDECNDNIIFS

EEYNTSNPDIPPHVQKSVNNDMIVTDNNGAVKFPQLCKFCDVRFSTCDNQKSCMSNCSITSIC

EKPQEVCVAVWRKNDENITLETVCHDPKLPYHDFILEDAASPKCIMKEKKKPGETFFMCSCSS

DECNDNIIFSEEYNTSNPDGGGSGGGSGGGTHTCPPCPAPELLGGPSVFLFPPKPKDTLMIS

RIPEVTCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSLTCLVKGFYPSDIAV

EWESNGQPENNYKTIPPVLDSDGSFFLYSKLTVDKSRWQQGNVFSCSVMHEALHNHYTQK

SLSLSPG

In a specific embodiment, the polypeptide construct comprises a polypeptide of the present invention that exhibits significantly enhanced potency, for example a polypeptide the exhibits significant enhanced potency may comprise SEQ ID NO: 10, SEQ ID NO.14, SEQ ID NO:17, SEQ ID NO: 20 or SEQ ID NO:23. In another specific embodiment, the polypeptide construct may be a homodimer comprising two polypeptides that exhibit significant enhanced potency; for example if the polypeptide construct that exhibits significant enhanced potency is SEQ ID NO: 14, the polypeptide construct is a homodimer comprising two polypeptide constructs wherein each polypeptide construct comprising SEQ ID NO.14. Likewise, if the polypeptide that exhibits enhanced potency is SEQ ID NO: 10, 14, 17, 20, or 23, a homodimer of the present invention likewise comprises two polypeptide constructs wherein each polypeptide of the homodimer is SEQ ID NO: 10, 14, 17, 20 or 23 respectively.

As noted, these single chain polypeptide constructs will dimerize when secreted from a production host, yielding a dimeric polypeptide construct comprising two single chain polypeptides linked by way of disulfide bridges that form between the constant domains of the two single chain polypeptides.

By "significantly enhanced potency" we mean that the effect or activity of a present polypeptide construct in this dimeric form is greater than a counterpart construct when measured in an assay relevant for assessing the biological activity of TGF-β. Appropriate means for making this determination are exemplified herein. For example, the N-terminal Fc-fused T22d35 doublets neutralizes TGF-β to a much better extend than the N-terminally Fc-fused T2m singlet as was illustrated by the TGF-β-induced IL-11 release by A549 cells (FIG. 7).

It is observed that fusion constructs of this type have advantages relative to several other versions of TβRII receptor-ectodomain based molecules, including non-Fc fused bivalent TGF-β receptor ectodomain constructs (such as the T22d35 doublet) and constructs in which a single receptor ectodomain is fused to the N-terminus of an Fc region. In particular, the presently provided Fc fusion constructs have improved manufacturability due to the presence of the Fc region (for example, purification can be accomplished using protein A chromatography). The Fc region also allows for improved circulating half-lives. Importantly, the present constructs have substantially higher TGF-β neutralization potencies compared to the singlet fusion (T2m-Fc) and non-Fc-fused doublet ectodomain (T22d35). The N-terminally fused TGF-β ECD doublet Fc constructs (T22d35-Fc) provided exhibit advantages with respect to significant improvement in TGF-β ligand neutralizing potency (as shown, for example, in the over 970-fold improvement in TGF-β1 neutralization relative to non-Fc fused doublet, as shown in FIG. 7). Additionally, they exhibit improved manufacturability, as demonstrated by biophysical analysis showing a >99% monomeric content (i.e. the minimal presence of aggregates and the absence of fragments of the purified N-terminally fused T22d35-Fc constructs) (as illustrated in FIG. 6). Thus, an advantage of the present invention is an unexpected high potency of TGF-β ligand neutralization, including some degree of neutralization of TGF-β2, which is not observed with the T2m-Fc (Fc-singlet) or T22d35 (non Fc-fused) constructs.

In specific embodiments, the second region of the polypeptide construct of the present invention is selected from a group of sequences displaying variation in the N-terminal sequence as exemplified by SEQ ID NO:12, 15, 18, 24. These may differ in length and the number of cysteine residues retained from the hinge region as a means to modulating the degree of Fc-region dimerization and hence impacting on both efficacy and manufacturability. Thus, in embodiments, the polypeptide construct comprises a variation in the constant domain, wherein at least one cysteine residue involved in cross-linking is deleted or substituted. Suitable substitutions include serine or alanine, and preferably by serine.

A substantially identical sequence may comprise one or more conservative amino acid mutations that still provide for proper folding upon secretion into the culturing medium. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions while maintaining the overall structure of the constant domains; thus the function of the Fc is maintained.

In a specific, non-limiting example, the first region of the polypeptide construct of the present invention may comprise a TGF-β receptor type II, such as:

(SEQ ID NO: 1, also referred to herein as T2m)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In preferred embodiments, the polypeptide constructs comprise a TβRII-ECD "doublet", in which a TβRII-ECD is linked in tandem with another TβRII-ECD, which ectodomains can be the same or different TGF-β superfamily receptor ectodomains, such as:

(SEQ ID NO: 5, also referred to herein as T22d35)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIF

-linker-

QLCKFCDVRFSTCDNQKSCMSNCSITSICEKPQEVCVAVWRKNDENITLE

TVCHDPKLPYHDFILEDAASPKCIMKEKKKPGETFFMCSCSSDECNDNII

FSEEYNTSNPD where in one non-limiting embodiment the linker corresponds to SEQ ID NO:6; and a sequence substantially identical thereto. "Substantially identical" is as defined above.

The ectodomain doublet can incorporate the same or different ectodomains, both belonging to the TGFβ superfamily receptor family. In embodiments, the ectodomains bind the same target. In other embodiments, the ectodomains are of the same receptor species. In other embodiments, the ectodomains are identical and thus are homomeric.

For example, the polypeptide constructs of the present invention may have a TGF-β neutralization potency selected from the group consisting of at least 900-fold and 200-fold, more potent than the T22d35 doublet alone for TGFβ1 and TGF-β3, respectively. For example, in the IL-11 release assay the T22d35-Fc doublet construct is approximately 972-fold more potent in neutralizing TGF-β1 and approximately 243-fold more potent in neutralizing TGF-β3, when compared with the non-Fc-fused T22d35 doublet alone.

In another example, the potency of the construct is at least 600-fold and at least 20-fold greater for neutralizing TGF-β1 and TGF-β3, respectively, than a construct in which the antibody constant domain is coupled to a single ectodomain rather than to a doublet. The polypeptide constructs of the present invention may have an at least 615-fold and 24-fold better neutralization potency for TGF-β1 and TGF-β3, respectively, when compared to the potency of a construct in which the antibody constant domain is coupled to a single ectodomain rather than to a doublet.

The neutralizing potency can be summarized as follows: the neutralizing potency of the Fc-fused doublet (ECD-ECD-Fc) is greater than the Fc-fused ECD monomer (ECD-Fc); i.e. ECD-ECD-Fc >ECD-Fc, whereas the ECD-Fc is more potent than the non-Fc-fused doublet (ECD-ECD) and the non-Fc fused doublet ECD is more potent than the non-Fc fused singlet ECD; i.e. ECD-ECD-Fc >>ECD-Fc >ECD-ECD >>ECD). In terms of manufacturability, the presence of an Fc protein allows for Protein A purification and prevents having to use cleavable tags. In addition, positioning the singlet or doublet ECD at the N-terminus of the Fc portion prevents aggregation issues due to the inappropriate pairing of the cysteine residues in the hinge region of the Fc portion. Therefore, fusion of the ECD singlet or doublet to the N-terminus of the Fc portion provides an improved manufacturability over C-terminal fusions (N-terminal fusions have a higher percentage of monomeric species, less aggregates, less fragments). In addition an unexpected significant increase is observed in TGF-β neutralization potency for all TGF-β isotypes for the N-terminal Fc fused doublet ECD compared to the N-terminal Fc fused T2m singlet ECD.

Additionally, when the polypeptide constructs of the present invention include a TβRII-ECD that binds TGF-β, the polypeptide construct may neutralize, to varying extents, all three isotypes of TGF-β (that is, TGF-β1, TGF-β2, and TGF-β3).

The polypeptide constructs of the present invention have, as assessed in cell-based assays, TGF-β neutralizing potencies that are significantly higher (20-fold or more) than those of bivalent comparator polypeptides, i.e. non-Fc-fused T22d35 (doublet alone) and T2m-Fc (Fc fused singlet). Within the series of polypeptide constructs of the present invention, those that contain two or more copies of the TβRII-ECD fused to the N-terminus of the Fc constant region have potencies that are higher than those constructs that contain only one copy, as assessed in cell based assays.

The polypeptide construct of the present invention is expressed as a single polypeptide chain.

Once expressed, the polypeptide construct of the present invention forms a dimer wherein the $C_H2$ and $C_H3$ domains of the respective polypeptide constructs interact to form a properly assembled Fc region such as occurs when the expressed products are secreted into the culturing medium.

The polypeptide construct of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc, $His_5$, $His_6$, or $His_8G$), or a combination thereof. In another example, the signal peptide may be MDWTWRILFLVAAATGTHA (SEQ ID NO:11). In a further example, the additional sequence may be a biotin recognition site such as that described in [WO/1995/04069] or in [WO/2004/076670]. As is also known to those of skill in the art, linker sequences may be used in conjunction with the additional sequences or tags, or may serve as a detection/purification tag. Suitably, the constant region comprises a protein A binding site (residing typically between about $C_H2$ and $C_H3$) that permits the single chain polypeptide to be extracted/isolated using a protein A affinity approach.

The present invention also encompasses nucleic acid sequences encoding the molecules as just described above. Given the degeneracy of the genetic code, a number of nucleotide sequences would have the effect of encoding the desired polypeptide, as would be readily understood by a skilled artisan. The nucleic acid sequence may be codon-optimized for expression in various micro-organisms. The present invention also encompasses vectors comprising the nucleic acids as just described, wherein the vectors typically comprise a promoter and signal sequence that are operably linked to the construct-encoding polynucleotide for driving expression thereof in the selected cellular production host. The vectors can be the same or different provided both result in secretion of the dimeric polypeptide construct.

Furthermore, the invention encompasses cells, also referred to herein as transgenic cellular host, comprising the nucleic acid and/or vector as described, encoding a first polypeptide construct. The host cells may comprise a second nucleic acid and/or vector encoding a second polypeptide construct different from the first polypeptide construct. The co-expression of the first and second polypeptide constructs may lead to the formation of heterodimers.

The present invention also encompasses a composition comprising one or more than one polypeptide construct as described herein. The composition may comprise a single polypeptide construct as described above, or may be a mixture of polypeptide constructs. The composition may also comprise one or more than one polypeptide construct of the present invention linked to one or more than one cargo molecule. For example, and without wishing to be limiting in any manner, the composition may comprise one or more than one polypeptide construct of the present invention linked to a cytotoxic drug in order to generate an antibody-drug conjugate (ADC) in accordance with the present invention.

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or fragment thereof to the gastrointestinal tract of the subject. Thus, the composition may comprise encapsulation, time-release, or other suitable technologies for delivery of the antibody or fragment thereof. It would be within the competency of a person of skill in the art to prepare suitable compositions comprising the present compounds.

The constructs of the present invention may be used to treat diseases or disorders associated with over-expression or over-activation of ligands of the TGF-β superfamily. The disease or disorder can be selected from, but not limited to, cancer, ocular diseases, fibrotic diseases, or genetic disorders of connective tissue.

In the field of cancer therapy, it has recently been demonstrated that TGF-β is a key factor inhibiting the antitumor response elicited by immunotherapies, such as immune checkpoint inhibitors (ICI's) (Hahn & Akporiaye, 2006). Specifically, therapeutic response to ICI antibodies results primarily from the re-activation of tumor-localized T-cells. Resistance to ICI antibodies is attributed to the presence of immunosuppressive mechanisms that result in a dearth of T-cells in the tumor microenvironment. Thus, it is now recognized that in order to elicit responses in resistant patients, ICI antibodies need to be combined with agents that can activate T-cells and induce their recruitment into the tumor, i.e. reversing of the "non-T-cell-inflamed" tumor phenotype. One publication noted that overcoming the non-T-cell-inflamed tumor microenvironment is the most significant next hurdle in immuno-oncology (Gajewski, 2015).

We have shown using a proof-of-principle TGF-β trap, T22d35, that blocking of TGF-β effectively reverses the "non-T cell inflamed" tumor phenotype (Zwaagstra et al, 2012). This positions anti-TGF-β molecules as potential synergistic combinations with ICI's and other immunotherapeutics. In support of this, a 2014 study (Holtzhausen et al., ASCO poster presentation) examined effects of a TGF-β blocker when combined an anti-CTLA-4 antibody in a physiologically-relevant transgenic melanoma model. The study demonstrated that while anti-CTLA-4 antibody monotherapy failed to suppress melanoma progression, the combination of the TGF-β antagonist and anti-CTLA-4 antibody significantly and synergistically suppressed both primary melanoma tumor growth as well as melanoma metastasis. These observations correlated with significant increases in effector T-cells in melanoma tissues.

We show herein that the present polypeptides having the basic structure that is T22d35-Fc significantly reduce tumor growth in a syngeneic mouse MC-38 colon cancer model. This thus positions anti-TGF-β molecules to be used in a potential synergistic combination with other immunotherapeutics.

The present constructs can be useful to treat fibrotic diseases including those that affect any organ of the body, including, but not limited to kidney, lung, liver, heart, skin and eye. These diseases include, but are not limited to, chronic obstructive pulmonary disease (COPD), glomerulonephritis, liver fibrosis, post-infarction cardiac fibrosis, restenosis, systemic sclerosis, ocular surgery-induced fibrosis, and scarring.

Genetic disorders of connective tissue can also be treated, and include, but are not limited to, Marfan syndrome (MFS) and Osteogenesis imperfecta (O).

The present invention will be further illustrated in the following examples. However, it is to be understood that these examples are for illustrative purposes only and should not be used to limit the scope of the present invention in any manner.

Materials & Methods
Production & Purification
Transient CHO Expression

The various TβRII-ECD fusion variants (such as T2m-Fc and T22d35-Fc) are each comprised of a heavy chain Fc region, and include the signal sequence MDWTWRIL-FLVAAATGTHA (SEQ ID NO:11) at their N-termini. The DNA coding regions for the constructs were prepared synthetically (Biobasic Inc. or Genescript USA Inc.) and were cloned into the HindIII (5' end) and BamH1 (3' end) sites of the pTT5 mammalian expression plasmid vector (Durocher et al, 2002). Fusion proteins were produced by transient transfection of Chinese Hamster Ovary (CHO) cells with the heavy chain T2m or T22d35 fused to the IgG heavy chain (T2m-Hc and T22d35-HC, respectively) construct. Briefly, T2m-HC or T22d35-HC plasmid DNAs were transfected into a 2.5 L and 4.6 L culture, respectively, of CHO-3E7 cells in FreeStyle F17 medium (Invitrogen) containing 4 mM glutamine and 0.1% Kolliphor p-188 (Sigma) and maintained at 37° C. Transfection conditions were: DNA (80% plasmid construct, 15% AKT plasmid, 5% GFP plasmid): PEIpro (ratio 1:2.5): PEI(polyethylenimine)pro (Polyplus) (ratio=1:2.5). At 24 hours post-transfection, 10% Tryptone N1 feed (TekniScience Inc.) and 0.5 mM Vaporic acid (VPA, Sigma) were added and the temperature was shifted to 32° C. to promote the production and secretion of the fusion proteins and then maintained for 15 days post transfection after which the cells were harvested. At final harvest the cell viability was 89.6%.

Stable Pool CHO Expression $CHO^{BRI/rcTA}$ cell pools were generated by transfecting cells with the vector expressing the target gene encoding the various Fc-fused TβRII-ECD proteins. The day after transfection, the cells were centrifuged for 5 min at 250 rpm and seeded at density of $0.5 \times 10^6$ cells/mL in selection medium (PowerCHO2 medium supplemented with 50 μM of methionine sulfoximine). Selection medium was replaced every 2-3 days during 14 to 18 days with inoculation at $0.5 \times 10^6$ cells/mL. Cell number and viability were measured with the Cedex Innovatis' automated cell counter Cedex Analyzer as described above. When cell viability reached greater than 95%, pools were inoculated at $0.2 \times 10^6$ cells/mL in 125 or 250 mL Erlenmeyer flasks. For the fed-batch culture, $CHO^{BRI/rcTA}$ cell pools were inoculated as described above. At day three post-inoculation, when cells density reached 3.5 to $4.5 \times 10^6$ cells/mL, expression of the recombinant protein was induced by adding 2 μg/mL of cumate. MSX concentration was adjusted to 125 μM, and F12.7 feed (Irvine Scientific) was added followed by a temperature shift to 32° C. Every 2-3 days, cultures were fed with 5% (v:v) F12.7 and samples were collected for recombinant protein (pA-HPLC) and glucose (VITROS 350, Orthoclinical Diagnostics, USA) concentration determination. Glucose was added in order to maintain a minimal concentration of 17 mM.

Purification

The harvest supernatant from the CHO cells was filtered (0.2 μm) and loaded onto a Protein A MabSelect Sure column (GE Healthcare). The column was washed with 2 column volumes of PBS and protein was eluted with 3 column volumes of 0.1 M sodium citrate pH 3.6. To maximize the yield, the flow through was reloaded onto the Protein A column and eluted as described above. Eluted fractions were neutralized with 1 M Tris, and those containing the fusion proteins were pooled and subsequently loaded onto a Hi-load Superdex S200 26/60 size exclusion chromatography (SEC) column (GE Healthcare) equilibrated in formulation buffer (DPBS without $Ca^{2+}$, without $Mg^{2+}$). Protein was eluted using 1 column volume formulation buffer, collected into successive fractions and detected by UV absorbance at 280 nm. The main peak SEC fractions containing the fusion proteins were then pooled and concentrated. The integrity of the Prot-A and SEC purified fusion proteins in the pooled fractions was further analyzed by UPLC-SEC and SDS-PAGE (4-15% polyacrylamide) under reducing and non-reducing conditions (SYPRO Ruby staining). For UPLC-SEC, 2-10 μg of protein in DPBS (Hyclone, minus $Ca^{2+}$, minus $Mg^{2+}$) was injected onto a Waters BEH200 SEC column (1.7 μm, 4.6×150 mm) and resolved under a flow rate of 0.4 mL/min for 8.5 min at room temperature, using the Waters Acquity UPLC H-Class Bio-System. Protein peaks were detected at 280 nm (Acquity PDA detector).

Cell Lines

Human A549 non-small cell lung cancer cells were purchased from ATCC (Cat #CCL-185, Cedarlane, Burlington, ON). Cells were cultured in Dulbecco's Modified Eagles Medium (DMEM) supplemented with 5% Fetal Bovine Serum (FBS). MC-38 mouse colon adenocarcinoma cells were purchased from Kerafast (Cat #ENH204, Boston, MA), and cultured in Dulbecco's modified MEM supplemented with 2 mM L-glutamine and 10% fetal bovine serum. Both cell lines were maintained at 37° C., in a humidified atmosphere supplemented with 5% $CO_2$.

TGF-β Induced A549 Cell IL-11 Release Assay

Human A549 lung cancer cells were seeded in 96-well plates ($5 \times 10^3$ cells/well). The following day 10 pM TGF-β in complete media, in the absence or presence of a serial dilution of TGF-β Trap fusion protein, was incubated for 30 min at RT prior to adding to the cells. After 21h of incubation (37° C., 5% $CO_2$, humidified atmosphere) conditioned medium was harvested and added to MSD Streptavidin Gold plates (Meso Scale Diagnostics, Gaithersburg, MD) that were coated with 2 μg/mL biotinylated mouse anti-human IL-11 antibody (MAB618, R&D Systems, Minneapolis, MN). After 18h (4° C.) plates were washed with PBS containing 0.02% Tween 20 and then 2 μg/mL SULFO-tagged goat anti-human IL-11 antibody (AF-218-NA, R&D Systems Minneapolis, MN) was added and plates were incubated for 1 h at RT. After a final wash, plates were read in a MESO QuickPlex SQ120 machine (Meso Scale Diagnostics, Gaithersburg, MD). IL-11 readouts were expressed as percent IL-11 release compared to control cells treated with TGF-β alone. Graphpad Prism (4-PL algorithm ((log (inhibitor) vs. response—variable slope (four parameters)) was used to calculate the $IC_{50}$ (the automatic outlier option was used when needed).

In Vivo Evaluation in a Syngeneic Mouse Colon Cancer MC-38 Subcutaneous Mouse Model Female C57BL/6-Elite mice (5-7 weeks old) were purchased from Charles River Laboratories (Wilmington, MA). Thirteen C57BL/6 mice were injected on day 0 with $3 \times 10^5$ MC-38 cells subcutaneously into the right flank. When tumors reached a volume of 50-100 mm³ (day 5) animals were divided in 2 cohorts and treatment was initiated:

Cohort 1 (7 animals): Isotype control (CTL IgG; BioxCell InVivo MAb Rat IgG2b, anti-KLH; Clone LTF-2, Cat #BE0090); 200 μg in 100 μL phosphate-buffered saline (PBS), intra-peritoneal (i.p.) on day 5, 7, 9, and 11.

Cohort 2 (6 animals): T22d35-Fc, 5 mg/kg in 100 μL PBS, i.p. on day 5, 9, 12, and 16.

Tumors were measured twice a week using digital calipers up to 15 days after commencing treatment. Tumor volumes were calculated from these measurements using a modified ellipsoidal formula ($T_\pi = \pi/6 \times (Length \times Width \times Width)$) described previously (Tomayko et al., 1986).

Results & Discussion

Fusion Construct Design

In order to generate TGF-β traps of interest, we fused the TβRII-ECD singlet (designated T2m) to another such singlet thereby forming the ectodomain doublet (designated T22d35) that was coupled to the N-termini of the heavy chains of a human (h)IgG2 Fc region and a human IgG1 Fc region. FIG. 1 shows schematics (FIG. 1A) and amino acid sequences (FIG. 1B) of the T2m and T22d35. These modules were fused to the N-termini of the heavy chains of an IgG Fc region (FIG. 2A) using several linker variations (FIG. 2E) in order to generate the T2m-Fc (FIG. 2B) and T22d35-Fc variants (FIG. 2C) fusions. The sequences of these fusions are shown in FIG. 2D. We also designed variants of T22d35-Fc that explore the number of cysteine residues in the hinge region of the Fc domain, different IgG isotypes (human IgG1 versus IgG2), and sequences of varying length and nature as linkers between T22d35 and the N-terminus of the Fc domain (FIGS. 2E, 2F & 2G). These variations aim at exploring and eventually optimizing the functional and manufacturability attributes of the T22d35-Fc design.

Expression and Purification

Purification of Transient CHO Material

The respective fusion protein constructs were expressed transiently in CHO-3E7 cells (see Table 1) after which the conditioned medium was harvested and purified using a protein A affinity column, followed by preparative Size Exclusion Chromatography (SEC). SEC elution profiles of the T2m-Fc (FIG. 3A) and T22d35-Fc (FIG. 4A) showed that these fusion proteins are relatively pure and devoid of aggregates. Fractions 6-11 (T2m-Fc) and 7-10 (T22d35-Fc) were pooled and concentrated to 5.6 mg/mL (T2m-Fc) and 6.03 mg/mL (T22d35-Fc). The final yields were 267 mg and 168 mg for T2m-Fc and T22d35-Fc, respectively. The final products (indicated SEC pooled fractions) were shown to be >99% pure by UPLC-SEC (FIGS. 3B & 4B). SDS-PAGE assessment (FIGS. 3C & 4C, Sypro RUBY staining) shows the T2m-Fc and T22d35-Fc bands of ~60 kDa and ~90 kDa under reducing conditions, whereas bands of approximately 90 kDa and 150 kDa can be detected, representing the fully assembled and highly pure T2m-Fc and T22d35-Fc fusion proteins, respectively, under non-reducing conditions. An overview of the production and purification details can be found in Table 1. Together, these results demonstrate the good manufacturability of the T2m-Fc and T22d35-Fc fusion proteins.

TABLE 1

Production (transient pools) and purification details of the T2m-Fc and T22d35-Fc fusion proteins.

|  | T2m-Fc | T22d35-Fc |
| --- | --- | --- |
| Cell line | CHO-3E7 | CHO-3E7 |
| production method | Transient | Transient |
| Production volume (L) | 2.5 | 4.6 |
| % GFP @ 24 hpt (Cellometer K2) | 38.5 | 41 |
| Production length (days post transfection) | 15 | 15 |
| Average cell viability @ harvest (%) | 88.43 | 89.4 |
| Final volume (L; after 0.2 μm filtration) | 2.458 | 4.368 |
| Titre (mg/mL: pA-HPLC) | 139 | 54 |
| Maximum expected yield (mg) | 341 | 235 |
| Final yield (mg) | 267 | 168 |
| Recovery (%) | 78.30 | 71.49 |

Purification of Stable CHO Pool Material

N- and C-terminally Fc-fused T22d35 variants were stably expressed in $CHO^{BRI/rcTA}$ cells in order to compare their level of expression and some of their biophysical properties. The coding region of each variant was ligated into mammalian cell expression plasmids and, after transfection, an enriched pool of cells was selected that stably expressed each of the variants. The main difference between the variants can be found in the amino acid sequence composing the linker region that separates the T22d35 doublet from the Fc domain (in the case of the N-terminal fusions), while for the C-terminal Fc-fusions, the difference between each of the variants is at the extreme amino-terminus of the protein (Table 2).

TABLE 2

Description of amino acid variations in the linker region of the N- and C-terrninal Fc-fused T22d35 fusions (Bold: natural linker sequence; italics: artificial linker sequence). The paired cysteine residues in each of the variants are underlined.

| Variant ID | Fc Orientation/Isotype | Relevant sequence differences (SEQ ID NOs: 35-42) |
|---|---|---|
| T22d35-Fc | N-terminal/IgG2 | T22d35........ERK<u>CC</u>VE<u>C</u>PP<u>C</u>PAPP... |
| T22d35-Fc-IgG2-v2 | N-terminal/IgG2 | T22d35............VE<u>C</u>PP<u>C</u>PAPP... |
| T22d35-Fc-IgG1-v1 | N-terminal/IgG1 | T22d35............THT<u>C</u>PP<u>C</u>PAPE... |
| T22d35-Fc-IgG1-v2 | N-terminal/IgG1 | T22d35....VEPKSSDKTHT<u>C</u>PP<u>C</u>PAPE... |
| T22d35-Fc-IgG1-v3 | N-terminal/IgG1 | T22d35.*GGGSGGGSGGG*THT<u>C</u>PP<u>C</u>PAPE... |
| Fc-IgG1-T22d35-v1 | C-terminal/IgG1 | PP<u>C</u>PAPE...T22d35 |
| Fc-IgG1-T22d35-v2 | C-terminal/IgG1 | DKTHT<u>C</u>PP<u>C</u>PAPE...T22d35 |
| Fc-IgG2-T22d35-v1 | C-terminal/IgG2 | VE<u>C</u>PP<u>C</u>PAPP...T22d35 |

Fusion proteins were purified by protein A affinity and using 100 mM citrate (pH3.6) as the elution buffer. Eluted fusion protein samples were neutralized with 1 M HEPES then subjected to a buffer exchange to DPBS using Zeba spin columns (Table 3), while the integrity of several of the purified fusion proteins was assessed by SDS-PAGE (FIG. 5). Purification of each variant was similar. Although many of the properties were very similar between the variants, the potential for aggregation, which is indicative of improper folding, revealed some distinctions. Protein aggregation can be indicative of reduced conformational stability, and can result in decreased activity, efficacy or potency. Size-Exclusion Chromatography-High Performance Liquid Chromatography (SEC-HPLC) was used to determine the purity of each of the N- and C-terminal Fc-fused variants. This method allows for the accurate measurement of the percentage of intact monomeric species as well as the presence of impurities such as aggregates and/or degradation products. As shown in FIG. 6, a striking difference can be observed between T22d35 variants expressed as N-terminal Fc fusions and those expressed as C-terminal fusions. In particular, the percentage of intact monomer (FIG. 6A) was approximately 99% for all five N-terminal fusion variants (SEQ ID NO:10, SEQ ID NO:14, SEQ ID NO:17, SEQ ID NO:20, SEQ ID NO:23) whereas this was markedly lower for the three C-terminal fusions (SEQ ID NO:26, SEQ ID NO:27, SEQ ID NO:28). This significant decrease in the percentage of intact monomer results from the accumulation of increased higher molecular weight aggregates observed in all of the C-terminal Fc-fusions (FIG. 6B) as well as increased lower molecular weight fragments in two out of the three C-terminal Fc fusions (FIG. 6C). In addition, evaluation of the titers of the individual 500 mL productions and the average titers of the N-terminal Fc-fused and C-terminally Fc-fused T22d35 productions shows that the N-terminal Fc-fused T22d35 variants can be produced at higher yield compared to the C-terminal fusions (Table 4). Taken together, these results indicate that there are significant and unexpected advantages to expressing the T22d35 doublet at the N-terminus of moieties, such as the Fc portion of an immunoglobulin. Taken together these data demonstrate the enhanced manufacturability of the N-terminal Fc-fused T22d35 proteins.

TABLE 3

Overview of protein yields of the T22d35 variants after purification of 500 mL of stable pool material.

| | T22d35-Fc-IgG2 (CCCC) | T22d35-Fc-IgG2-v2 (CC) | T22d35-Fc-IgG1-v1 (CC) | T22d35-Fc-IgG1-v2 (SCC) | T22d35-Fc-IgG1-v3 (GSL-CC) | hIgG1Fc ΔK(C)-T22d35 | hIgG1Fc ΔK(CC)-T22d35 | hIgG2Fc ΔK(CC)-T22d35 |
|---|---|---|---|---|---|---|---|---|
| Cell line | CHO-55E1 | CHO-55E1 | CHO-55E1 | CHO-55E1 | CHO-55E1 | CHO-55E1 | CHO-55E1 | CHO-55E1 |
| Production method | Stable pool | Stable pool | Stable pool | Stable pool | Stable pool | Stable pool | Stable pool | Stable pool |
| Production volume at start (L) | 0.5 | 0.5 | 0.5 | 0.5 | 0.5 | 0.5 | 0.5 | 0.5 |
| Production length (days post induction) | 10 | 10 | 10 | 10 | 10 | 10 | 10 | 10 |
| Average cell viability @ harvest (%) | 69.4 | 97 | 97.6 | 95.1 | 98 | 94.3 | 95.7 | 90.3 |
| Final volume (L; after 0.2 μm filtration) | 0.65 | 0.65 | 0.65 | 0.65 | 0.65 | 0.65 | 0.65 | 0.65 |
| Titer (mg/L: pA-HPLC) | 212 | 214 | 556 | 353 | 526 | 260 | 339 | 119 |
| Maximum expected yield (mg) | 150 | 150 | 150 | 150 | 150 | 150 | 150 | 150 |
| Final yield (mg) | 67.34 | 62.17 | 81.64 | 81.74 | 74.84 | 70.95 | 81.49 | 48.73 |
| Recovery (%) | 44.89 | 41.45 | 54.43 | 54.49 | 49.89 | 47.30 | 54.33 | 32.49 |

TABLE 4

Comparison of the titers of the individual N- and C-terminal Fc-fused T22d35 fusions

| | N-terminal Fc Fusions | | | C-terminal Fc Fusions | | | Improvement |
|---|---|---|---|---|---|---|---|
| | Variant | Titer (mg/mL) | Average Titer (mg/mL) | Variant | Titer (mg/mL) | Average Titer (mg/mL) | Titer (N/C-terminal Fc-fusion) |
| hIgG1 | T22d35-Fc-IgG1-v1 (CC) | 556 | 478 | hIgG1FcΔK(C)-T22d35 | 260 | 300 | 63% |
| | T22d35-Fc-IgG1-v2 (SCC) | 353 | | hIgG1FcΔK(CC)-T22d35 | 339 | | |
| | T22d35-Fc-IgG1-v3 (GSL-CC) | 526 | | | | | |
| hIgG2 | T22d35-Fc (CCCC) | 212 | 213 | hIgG2FcΔK(CC)-T22d35 | 119 | 119 | 56% |
| | T22d35-Fc-IgG2-v2 (CC) | 214 | | | | | |

Functional In Vitro Assessment

Figure 8:
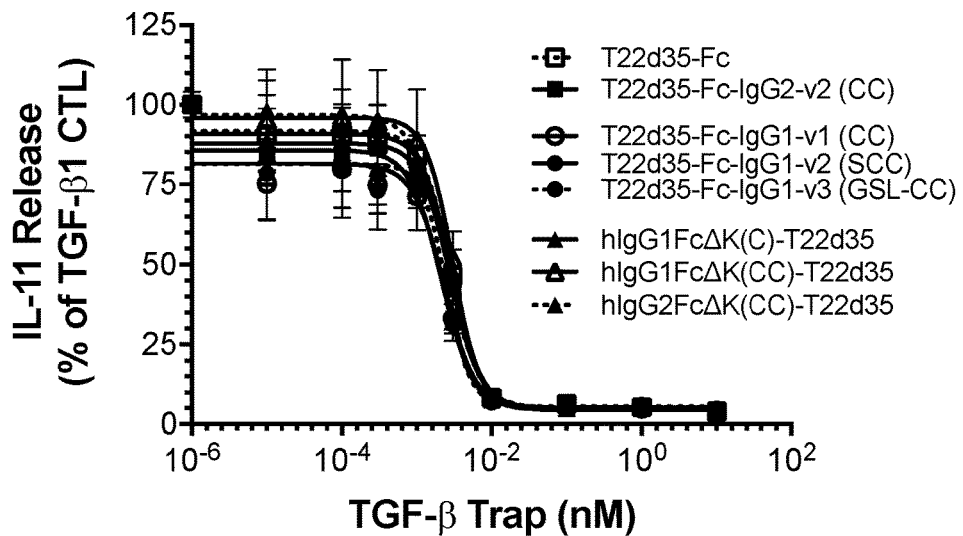
FIG. 8 provides a functional evaluation of the T22d35-Fc, T22d35-Fc-IgG2-v2(CC), T22d35-Fc-IgG1-v1(CC), T22d35-Fc-IgG1-v2(SCC), and T22d35-Fc-IgG1-v3(GSL-CC) compared to the C-terminal Fc-fused T22d35 trap variants in an A549 IL-11 release assay. Neutralization of TGF-β1, was assessed and calculated as a % of the TGF-β1 control (Average of a triplicate experiment +/−SD). The table lists the calculated $IC_{50}$ values calculated in Graphpad Prism (4-PL algorithm ((log (inhibitor) vs. response—variable slope (four parameters)).

The A549 cell IL-11 release assay was used to compare TGF-β neutralization potencies of the T2m-Fc and T22d35-Fc fusion proteins to the non-Fc-fused T22d35 single chain doublet trap, as shown in FIG. 7A/B/C. This data shows that for all TGF-β3 isotypes the potency of T22d35-Fc is superior to that of T2m-Fc and the non-Fc-fused T22d35 single chain trap, with a calculated $IC_{50}$ (Table 5) of 0.003348 and 0.003908 nM for TGF-β1 and TGF-β3, respectively. These values demonstrate potencies that are at least 970-fold and at least 240-fold better than for T22d35 ($IC_{50}$=3.253 and 0.9491 nM, for TGF-β1 and TGF-β3, respectively), and 615-fold and 24-fold better than for T2m-Fc ($IC_{50}$=2.059 and 0.0943 nM, for TGF-β1 and TGF-β3, respectively). In addition, T22d35-Fc neutralizes TGF-β32, albeit to a much lesser extend than TGF-β1 and -β3. In contrast, TGF-432 neutralization is not observed for either the T2m-Fc or the T22d35 single chain trap. It should be noted that, although the neutralization potency of the T22d35-Fc trap is similar for TGF-β1 and -β3, the T2m-Fc variant displayed a -22-fold higher neutralization potency for TGF-β3 compared to TGF-β1 (2.059 nM and 0.0943 nM, respectively). Evaluation of the additional N-terminal Fc-fused T22d35 fusions [T22d35-Fc-IgG2-v2 (CC), T22d35-Fc-IgG1-v1 (CC), T22d35-Fc-IgG1-v2 (SCC), and T22d35-Fc-IgG1-v3 (GSL-CC)] (FIG. 8, Table 6) showed that all of these fusions display comparable TGF-31 neutralization potencies, which were very similar to the potency of T22d35-Fc. Additional evaluation of the T22d35-Fc-IgG1-v1 (CC) variant (FIG. 9) confirms that, in line with the T22d35-Fc variant, its neutralization potency for TGF-β1 and -β3 is very similar ($IC_{50}$=0.003327 nM and 0.003251 nM, respectively) whereas this potency is much lower for TGF-β2 ($IC_{50}$=17.33 nM).

TABLE 5

Overview of the statistical evaluation of the curves shown in Figure 5 using the 4-PL algorithm ((log (inhibitor) vs. response – variable slope (four parameters)) available in Graphpad Prism.

| | TGF-β1 | | | TGF-β2 | | | TGF-β3 | | |
|---|---|---|---|---|---|---|---|---|---|
| | T22d35 | T2m-Fc | T22d35-Fc | T22d35 | T2m-Fc | T22d35-Fc | T22d35 | T2m-Fc | T22d35-Fc |
| HillSlope | -1.236 | -1.088 | -1.991 | -0.08682 | ~ -16.05 | ~ -4.763 | -1.022 | -0.965 | -1.318 |
| IC50 (nM) | 3.253 | 2.059 | 0.003348 | None | None | ~10.58 | 0.9491 | 0.0943 | 0.003908 |
| R square | 0.9364 | 0.8918 | 0.9364 | — | — | 0.676 | 0.9258 | 0.8634 | 0.9624 |
| Outliers (excluded, Q = 1%) | 0 | 2 | 1 | — | — | — | — | — | — |

TABLE 6

Overview of the statistical evaluation of the curves shown in Figure 7 using the 4-PL algorithm ((log (inhibitor) vs. response –variable slope (four parameters)) available in Graphpad Prism.

| | TGF-β1 | | | | |
|---|---|---|---|---|---|
| | T22d35-Fc | T22d35-Fc-IgG2-v2 (CC) | T22d35-Fc-IgG1-v1 (CC) | T22d35-Fc-IgG1-v2 (SCC) | T22d35-Fc-IgG1-v3 (GSL-CC) |
| HillSlope | -2.25 | -2.13 | -2.056 | -2.063 | -2.655 |
| IC50 (nM) | 0.002863 | 0.002783 | 0.002345 | 0.002128 | 0.002476 |
| R square | 0.9805 | 0.9844 | 0.9422 | 0.9729 | 0.9464 |

Functional In Vivo Assessment

Figure 9:
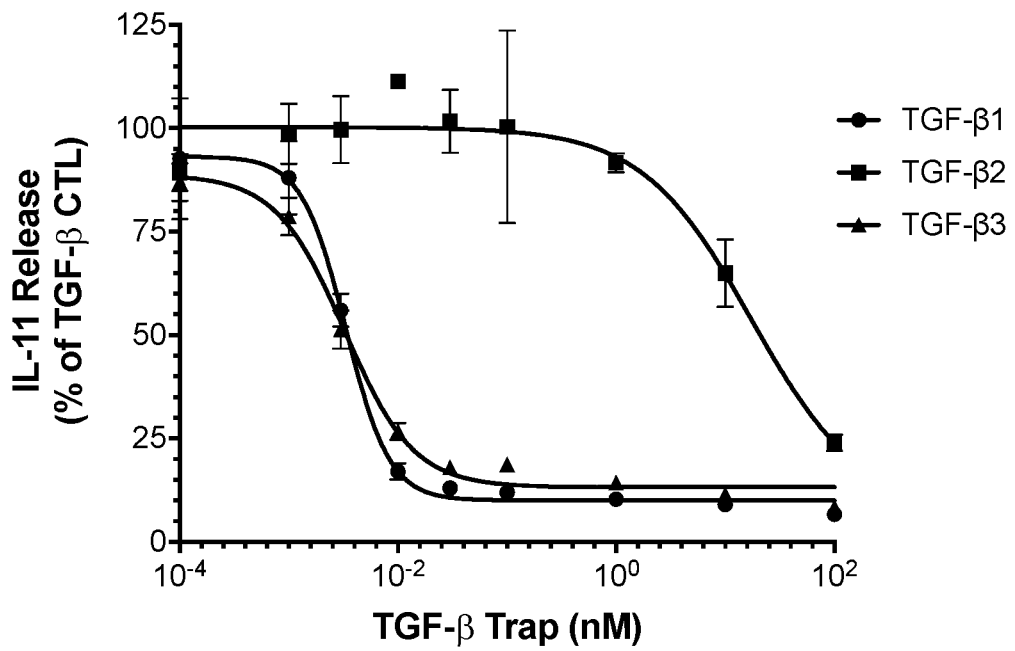
FIG. 9 provides a functional evaluation of the neutralization TGF-β1, -β2, and β3 by the T22d35-Fc-IgG1-v1(CC) variant in an A549 IL-11 release assay. TGF-β neutralization was assessed and calculated as a % of the TGF-β control (Average of a triplicate experiment+/−SD). The table lists the calculated $IC_{50}$ values calculated in Graphpad Prism (4-PL algorithm ((log (inhibitor) vs. response—variable slope (four parameters)).

The T22d35-Fc fusion protein (SEQ ID NO:10) was evaluated in vivo using a syngeneic MC-38 mouse colon carcinoma model (FIG. 9). The tumor growth in animals treated with the T22d35-Fc fusion was compared to the tumor growth in animals treated with a control IgG (CTL IgG). As shown in FIG. 9, no significant differences in tumor growth were observed up to day 11 post-treatment, however on day 15 a significant reduction in tumor growth can be observed in the tumor volume of animals treated with T22d35-Fc, when compared to the CTL IgG (Two-Way ANOVA). This data shows that administration of T22d35-Fc caused a significant inhibition in the growth of the MC-38 tumors compared to the group treated with the CTL IgG suggesting that blockage of TGF-β in vivo can abrogate the growth of tumors in this syngeneic model of colorectal cancer.

Listing of Sequences

| LISTING OF SEQUENCES | | |
|---|---|---|
| SEQ ID NO: | Sequence | Description |
| 1 | IPPHVQKSVNNDMIVTDNNGAVKFPQLCKFCDVRFSTCDNQKSC MSNCSITSICEKPQEVCVAVWRKNDENITLETVCHDPKLPYHDFI LEDAASPKCIMKEKKKPGETFFMCSCSSDECNDNIIFSEEYNTSN PD | TβRII-ECD including the structure domain and its natural linkers (also termed T2m) |
| 2 | IPPHVQKSVNNDMIVTDNNGAVKFPQLCKFCDVRFSTCDNQKSC MSNCSITSICEKPQEVCVAVWRKNDENITLETVCHDPKLPYHDFI LEDAASPKCIMKEKKKPGETFFMCSCSSDECNDNIIF | TβRII-ECD structured domain with its natural N-terminal linker |
| 3 | QLCKFCDVRFSTCDNQKSCMSNCSITSICEKPQEVCVAVWRKN DENITLETVCHDPKLPYHDFILEDAASPKCIMKEKKKPGETFFMC SCSSDECNDNIIFSEEYNTSNPD | TβRII-ECD structured domain with its with natural C-terminal linker |
| 4 | QLCKFCDVRFSTCDNQKSCMSNCSITSICEKPQEVCVAVWRKN DENITLETVCHDPKLPYHDFILEDAASPKCIMKEKKKPGETFFMC SCSSDECNDNIIF | TβRII-ECD structured domain |
| 5 | IPPHVQKSVNNDMIVTDNNGAVKFPQLCKFCDVRFSTCDNQKSC MSNCSITSICEKPQEVCVAVWRKNDENITLETVCHDPKLPYHDFI LEDAASPKCIMKEKKKPGETFFMCSCSSDECNDNIIFSEEYNTSN PDIPPHVQKSVNNDMIVTDNNGAVKFPQLCKFCDVRFSTCDNQK SCMSNCSITSICEKPQEVCVAVWRKNDENITLETVCHDPKLPYH DFILEDAASPKCIMKEKKKPGETFFMCSCSSDECNDNIIFSEEYN TSNPD | TβRII-ECD-TβRII-ECD fused dimer including structured domains and natural linkers (also termed T22d35) |
| 6 | SEEYNTSNPDIPPHVQKSVNNDMIVTDNNGAVKF | TβRII-ECD natural linker |
| 7 | IPPHVQKSVNNDMIVTDNNGAVKF | TβRII-ECD N-terminal natural linker |
| 8 | SEEYNTSNPD | TβRII-ECD C-terminal natural linker |
| 9 | IPPHVQKSVNNDMIVTDNNGAVKFPQLCKFCDVRFSTCDNQKSC MSNCSITSICEKPQEVCVAVWRKNDENITLETVCHDPKLPYHDFI LEDAASPKCIMKEKKKPGETFFMCSCSSDECNDNIIFSEEYNTSN PDERKCCVECPPCPAPPVAGPSVFLFPPKPKDTL MISRTPEVTCVVVDVSHEDPEVQFNWYVDGVEVHNAKTKPR EEQFNSTFRVVSVLTVVHQDWLNGKEYKCKVSNKGLPAPIE KTISKTKGQPREPQVYTLPPSREEMTKNQVSLTCLVKGFYPS DISVEWESNGQPENNYKTTPPMLDSDGSFFLYSKLTVDKSR WQQGNVFSCSVMHEALHNHYTQKSLSLSPG | T2m-Fc fusion of T2m with the hIgG2Fc(CCCC) Fc region |

LISTING OF SEQUENCES

| SEQ ID NO: | Sequence | Description |
|---|---|---|
| 10 | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD*ERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPG* | T22d35-Fc fusion f T22d35 *hIgG2Fc(CCCC)* Fc region |
| 11 | MDWTWRILFLVAAATGTHA | signal peptide |
| 12 | *ERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPG* | *hIgG2Fc(CCCC)* Fc region variant |
| 13 | SEEYNTSNPD*ERKCCVECPPCPAPP* | T22d35-Fc natural linker with the *hIgG2Fc(CCCC)* hinge region |
| 14 | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD*THTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKQVSLTCLVKGFYPSDIAVEWESNGQPENNYKTTPPVLDSDGSFFLYSKLTVDKSRWQQGNVFSCSVMHEALHNHYTQKSLSLSPG* | T22d35-Fc-IgG1-v1(CC) usion of *hIgG1Fc(CC)* Fc region |
| 15 | *THTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG* | *hIgG1Fc(CC)* Fc region variant |
| 16 | SEEYNTSNPD*THTCPPCPAPE* | T22d35-Fc-IgG1-v1(CC) natural linker with the *hIgG1Fc(CC)* hinge region |
| 17 | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD*VEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSPG* | T22d35-Fc-IgG1-v2(SCC) fusion of T22d35 with the *hIgG1Fc(CC)* Fc region |
| 18 | VEPKSSDKTHTCPPCPAPELLGG*PSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG* | *hIgG1Fc(CC)* Fc region variant |

LISTING OF SEQUENCES

| SEQ ID NO: | Sequence | Description |
|---|---|---|
| 19 | SEEYNTSNPD*VEPKSSDKTHTCPPCPAPE* | T22d35-Fc-IgG1-v2(SCC) natural linker with the *hIgG1Fc(CC)* hinge region |
| 20 | IPPHVQKSVNNDMIVTDNNGAVKFPQLCKFCDVRFSTCDNQKSC MSNCSITSICEKPQEVCVAVWRKNDENITLETVCHDPKLPYHDFI LEDAASPKCIMKEKKKPGETFFMCSCSSDECNDNIIFSEEYNTSN PDIPPHVQKSVNNDMIVTDNNGAVKFPQLCKFCDVRFSTCDNQK SCMSNCSITSICEKPQEVCVAVWRKNDENITLETVCHDPKLPYH DFILEDAASPKCIMKEKKKPGETFFMCSCSSDECNDNIIFSEEYN TSNPDGGGSGGGSGGG*THTCPPCPAPE LLGGPSVFLFPPKPKDTLMISRTPEVTCVVVDVSHEDPEVKF NWYVDGVEVHNAKTKPREEQYNSTYRVVSVLTVLHQDWLN GKEYKCKVSNKALPAPIEKTISKAKGQPREPQVYTLPPSRDE LTKNQVSLTCLVKGFYPSDIAVEWESNGQPENNYKTTPPVL DSDGSFFLYSKLTVDKSRWQQGNVFSCSVMHEALHNHYTQ KSLSLSPG* | T22d35-Fc-IgG1-v3(GSL-CC) with the fusion of T22d35 with the *hIgG1Fc(CC)* Fc region and including an artificial GS linker |
| 21 | GGGSGGGSGGG | Artificial GS linker of the T22d35-Fc-IgG1-v3(GSL-CC) fusion |
| 22 | SEEYNTSNPDGGGSGGGSGGG*THTCPPCPAPE* | T22d35-Fc-IgG1-v3(GSL-CC) linker including natural and artificial sequences and *hIgG1Fc(CC)* hinge region |
| 23 | IPPHVQKSVNNDMIVTDNNGAVKFPQLCKFCDVRFSTCDNQKSC MSNCSITSICEKPQEVCVAVWRKNDENITLETVCHDPKLPYHDFI LEDAASPKCIMKEKKKPGETFFMCSCSSDECNDNIIFSEEYNTSN PDIPPHVQKSVNNDMIVTDNNGAVKFPQLCKFCDVRFSTCDNQK SCMSNCSITSICEKPQEVCVAVWRKNDENITLETVCHDPKLPYH DFILEDAASPKCIMKEKKKPGETFFMCSCSSDECNDNIIFSEEYN TSNPD*VECPPCPAPPVAGPSVFLFPPKP KDTLMISRTPEVTCVVVDVSHEDPEVQFNWYVDGVEVHNAK TKPREEQFNSTFRVVSVLTVVHQDWLNGKEYKCKVSNKGLP APIEKTISKTKGQPREPQVYTLPPSREEMTKNQVSLTCLVKG FYPSDISVEWESNGQPENNYKTTPPMLDSDGSFFLYSKLTVD KSRWQQGNVFSCSVMHEALHNHYTQKSLSLSPG* | T22d35-Fc-IgG2-v2(CC) fusion of T22d35 with the *hIgG2Fc(CCCC)* Fc region |
| 24 | *VECPPCPAPPVAGPSVFLFPPKPKDTLMISRTPEVTCVVVDV SHEDPEVQFNWYVDGVEVHNAKTKPREEQFNSTFRVVSVLT VVHQDWLNGKEYKCKVSNKGLPAPIEKTISKTKGQPREPQV YTLPPSREEMTKNQVSLTCLVKGFYPSDISVEWESNGQPEN NYKTTPPMLDSDGSFFLYSKLTVDKSRWQQGNVFSCSVMH EALHNHYTQKSLSLSPG* | *hIgG2Fc(CCCC)* Fc region variant |
| 25 | SEEYNTSNPD*VECPPCPAPP* | T22d35-Fc-IgG2-v2(CC) natural linker with the *hIgG2Fc(CCCC)* hinge region |
| 26 | *PPCPAPELLGGPSVFLFPPKPKDTLMISRTPEVTCVVVDVSH EDPEVKFNWYVDGVEVHNAKTKPREEQYNSTYRVVSVLTVL HQDWLNGKEYKCKVSNKALPAPIEKTISKAKGQPREPQVYT LPPSRDELTKNQVSLTCLVKGFYPSDIAVEWESNGQPENNY KTTPPVLDSDGSFFLYSKLTVDKSRWQQGNVFSCSVMHEAL HNHYTQKSLSLSPG* IPPHVQKSVNNDMIVTDNNGAVKFPQLCKFCDVRFSTCDNQK SCMSNCSITSICEKPQEVCVAVWRKNDENITLETVCHDPKLPYH DFILEDAASPKCIMKEKKKPGETFFMCSCSSDECNDNIIFSEEYN TSNPDIPPHVQKSVNNDMIVTDNNGAVKFPQLCKFCDVRFSTCD NQKSCMSNCSITSICEKPQEVCVAVWRKNDENITLETYCHDPKL PYHDFILEDAASPKCIMKEKKKPGETFFMCSCSSDECNDNIIFSE EYNTSNPD | hIgG1FcΔK(C)-T22d35 |

| SEQ ID NO: | Sequence | Description |
|---|---|---|
| 27 | *DKTHTCPPCPAPELLGGPSVFLFPPKPKDTLMISRTPEVTCV VVDVSHEDPEVKFNWYVDG*VEVHNAKTKPREEQYNSTYRV VSVLTVLHQDWLNGKEYKCKVSNKALPAPIEKTISKAKGQP REPQVYTLPPSRDELTKNQV*SLTCLVKGFYPSDIAVEWESN GQPENNYKTTPPVLDSDGSFFLYSKLTVDKSRWQQNVFSC SVMHEALHNHYTQKSLSLPG* <u>IPPHVQKSVNNDMIVTDNNGAVKFPQLCKFCDVRFS TCDNQKSCMSNCSITSICEKPQEVCVAVWRKNDENITLETYCHD PKLPYHDFILEDAASPKCIMKEKKKPGETFFMCSCSSDECNDNII FSEEYNTSNPDIPPHVQKSVNNDMIVTDNNGAVKFPQLCKFCDV RFSTCDNQKSCMSNCSITSICEKPQEVCVAVWRKNDENITLETV CHDPKLPYHDFILEDAASPKCIMKEKKKPGETFFMCSCSSDECN DNIIFSEEYNTSNPD</u> | h1gG1FcΔK(CC)- T22d35 |
| 28 | *VECPPCPAPPVAGPSVFLFPPKPKDTLMISRTPEVTCVVVDV SHEDPEVQFNWYVDGVEVHNAKTKPREEQFNSTFRVVSVLT VVHQDWLNGKEYKCKVSNKGLPAPIEKTISKTKGQPREPQV YTLPPSREEMTKNQVSLTCLVKGFYPSDISVEWESNGQPEN NYKTTPPMLDSDGSFFLYS*KLTVDKSRWQQGNVFSCSVMH EALHNHYTQKSLSLSPG <u>IPPHVQKSVNNDMIVIDNNGAVKFPQLCKFCDVRFSTCD NQKSCMSNCSITSICEKPQEVCVAVWRKNDENITLETVCHDPKL PYHDFILEDAASPKCIMKEKKKPGETFFMCSCSSDECNDNIIFSE EYNTSNPDIPPHVQKSVNNDMIVTDNNGAVKFPQLCKFCDVRFS TCDNQKSCMSNCSITSICEKPQEVCVAVWRKNDENITLETYCHD PKLPYHDFILEDAASPKCIMKEKKKPGETFFMCSCSSDECNDNII FSEEYNTSNPD</u> | h1gG2FcΔK(CC)- T22d35 |
| 29 | ATGGATTGGACCTGGAGAATCCTCTTCCTTGTAGCAGCAGCAA CAGGTACACATGCTATCCCTCCTCATGTTCAAAAGTCCGTTAA CAACGACATGATCGTCACCGATAACAACGGTGCTGTCAAGTTC CCACAACTCTGTAAGTTCTGCGATGTGCGTTTCTCCACATGTG ATAACCAGAAGTCCTGTATGAGCAACTGCTCAATCACCTCCAT CTGCGAAAAGCCACAAGAGGTATGCGTAGCTGTATGGCGAAA GAACGATGAAAACATCACCCTGGAAACCGTCTGTCACGATCCA AAGCTCCCATACCATGATTTCATCCTGGAAGACGCAGCTTCTC CAAAGTGTATCATGAAGGAGAAGAAGAAGCCCGGTGAAACCTT CTTCATGTGCTCCTGTTCCTCAGATGAATGCAACGATAACATC ATCTTCTCCGAGGAGTACAACACCTCCAACCCAGATATCCCTC CACACGTTCAGAAGTCCGTAAACAATGACATGATTGTGACCGA CAACAACGGGGCTGTTAAGTTCCCACAGCTCTGTAAGTTTTGC GACGTTAGGITCAGCACCIGTGATAATCAGAAGAGCTGCATGT CCAACTGCAGCATCACCAGTATTTGCGAGAAGCCTCAAGAAGT GTGTGTCGCTGTTTGGAGAAAGAACGACGAAAACATAACCCTG GAGACCGTTTGCCACGATCCAAAACTCCCATATCACGATTTCA TTCTGGAGGACGCCGCCAGTCCTAAATGTATAATGAAAGAGAA GAAGAAACCAGGGGAGACCTTCTTTATGTGCAGCTGCAGCAG CGACGAGTGTAACGATAATATAATTTTTAGCGAGGAGTATAATA CAAGCAATCCCGACGAGCGCAAGTGCTGCGTCGAGTGCCCTC CATGCCCTGCCCCTCCTGTTGCCGGACCTAGTGTGTTTTTGTT TCCTCCTAAACCTAAAGATACACTCATGATTAGCAGGACACCT GAGGTGACATGTCGTCGTGGACGTGAGTCATGAAGACCCC GAAGTGCAGTTTAATTGGTATGTCGACGGAGTCGAAGTCCATA ATGCCAAAACTAAACCAAGGGAAGAACAGTTTAATTCAACTTTT CGCGTGGTCTCTGTGCTGACTGTGGTCACCAGGACTGGCTT AATGGAAAGGAATACAAGTGTAAGGTGAGTAATAAGGGCCTGC CCGCCCCCATTGAAAAAACTATTAGTAAGACTAAAGGGCAGCC CCGAGAGCCCCAGGTGTATACTTTGCCCCCCTCTCGGGAGGA GATGACTAAAAATCAGGTGAGTCTTACATGTCTTGTGAAAGGA TTTTACCCCTCTGACATTTCAGTGGAGTGGGAGTCTAATGGCC AGCCCGAGAATAATTACAAAACTACTCCCCCCATGTTGGACTC TGACGGCTCATTTTCTTGTACTCTAAACTGACAGTGGACAAAA GTCGGTGGCAGCAGGGCAATGTGTTTTCTTGTTCAGTGATGCA CGAGGCCCTGCATAATCACTATACACAGAAATCTCTGTCTCTG TCACCCGGCTGATGA | Nucleic acid sequence encoding T22d35-Fc in secretable form |

| SEQ ID NO: | Sequence | Description |
|---|---|---|
| 30 | ATGGACTGGACCTGGAGAATCCTGTTCCTGGTGGCTGCTGCT<br>ACCGGAACACACGCTATCCCCCCTCATGTGCAGAAGTCCGTG<br>AACAATGACATGATCGTGACAGATAACAATGGCGCCGTGAAGT<br>TTCCTCAGCTGTGCAAGTTCTGTGACGTGAGGTTTAGCACCTG<br>CGATAACCAGAAGTCCTGCATGAGCAATTGTTCTATCACATCC<br>ATCTGCGAGAAGCCACAGGAGGTGTGCGTGGCCGTGTGGCG<br>GAAGAACGACGAGAATATCACCCTGGAGACAGTGTGCCACGA<br>TCCTAAGCTGCCATACCATGACTTCATCCTGGAGGATGCTGCC<br>TCTCCCAAGTGTATCATGAAGGAGAAGAAGAAGCCTGGCGAG<br>ACATTCTTCATGTGCTCCTGTTCCAGCGACGAGTGCAACGATA<br>ATATCATCTTCAGCGAGGAGTATAACACCTCTAATCCAGATATC<br>CCACCCCACGTGCAGAAGTCTGTCAATAACGATATGATTGTCA<br>CAGATAACAATGGCGCTGTGAAGTTTCCCCAGCTGTGCAAATT<br>TTGTGACGTGAGATTTTCCACCTGTGATAACCAGAAGAGCTGC<br>ATGTCTAATTGTTCCATCACATCTATTTGTGAAAAACCTCAGGA<br>AGTGTGCGTGGCCGTGTGGAGAAAAAATGATGAAAACATCAC<br>CCTGGAGACAGTGTGCCATGATCCCAAGCTGCCTTATCACGA<br>CTTCATCCTGGAAGACGCTGCCAGCCCAAAATGCATTATGAAA<br>GAGAAGAAGAAGCCCGGTGAGACATTCTTCATGTGCAGCTGTT<br>CTTCTGATGAATGTAACGATAATATCATCTTTTCCGAGGAGTAT<br>AACACAAGCAATCCCGACACCCACACATGCCCTCCATGTCCAG<br>CTCCTGAGCTGCTGGGAGGACCTAGCGTGTTCCTGTTTCCCC<br>CTAAGCCAAAGGATACCCTGATGATCAGCAGGACCCCCGAGG<br>TGACATGCGTGGTGGTGGACGTGTCTCACGAGGACCCCGAGG<br>TGAAGTTTAACTGGTACGTGGACGGCGTGGAGGTGCATAATG<br>CCAAGACCAAGCCTAGGGAGGAGCAGTACAACTCTACCTATC<br>GGGTGGTGTCCGTGCTGACAGTGCTGCATCAGGATTGGCTGA<br>ACGGCAAGGAGTATAAGTGCAAGGTGTCCAATAAGGCTCTGC<br>CAGCCCCCATTGAGAAGACCATCAGCAAGGCTAAGGGCCAGC<br>CAAGAGAGCCCCAGGTGTACACACTGCCACCCTCTCGCGACG<br>AGCTGACCAAGAACCAGGTGTCCCTGACATGTCTGGTGAAGG<br>GCTTCTATCCTTCCGATATCGCTGTGGAGTGGGAGAGCAACG<br>GACAGCCAGAGAACAATTACAAGACCACACCTCCAGTGCTGG<br>ACTCTGATGGCTCCTTCTTTCTGTATAGCAAGCTGACCGTGGA<br>CAAGTCTAGGTGGCAGCAGGGCAACGTGTTTAGCTGTTCTGT<br>GATGCATGAGGCCCTGCACAATCATTACACACAGAAGTCCCTG<br>AGCCTGTCTCCTGGC | Nucleic acid sequence encoding T22d35-Fc-IgG1-v1(CC) in secretable form |
| 31 | ATGGACTGGACCTGGAGAATCCTGTTCCTGGTGGCTGCTGCT<br>ACCGGAACACACGCTATCCCCCCTCATGTGCAGAAGTCTGTG<br>AACAATGACATGATCGTGACAGATAACAATGGCGCCGTGAAGT<br>TTCCCCAGCTGTGCAAGTTCTGTGACGTGAGGTTTTCCACCTG<br>CGATAACCAGAAGTCTTGCATGTCCAATTGTAGCATCACATCT<br>ATCTGCGAGAAGCCTCAGGAGGTGTGCGTGGCCGTGTGGCG<br>GAAGAACGACGAGAATATCACCCTGGAGACAGTGTGCCACGA<br>TCCTAAGCTGCCATACCATGACTTCATCCTGGAGGATGCTGCC<br>AGCCCAAAGTGTATCATGAAGGAGAAGAAGAAGCCCGGCGAG<br>ACATTCTTCATGTGCTCTTGTTCCAGCGACGAGTGCAACGATA<br>ATATCATCTTCTCCGAGGAGTATAACACCAGCAATCCTGACAT<br>CCCACCCCACGTGCAGAAGAGCGTCAATAACGATATGATTGTC<br>ACAGATAACAATGGCGCTGTGAAGTTTCCACAGCTGTGCAAAT<br>TTTGTGACGTGAGATTTTCTACCTGTGATAACCAGAAGTCCTG<br>CATGAGCAATTGTTCTATCACATCCATCTGCGAGAAGCCACAG<br>GAAGTGTGCGTGGCCGTGTGGAGAAAAAATGATGAAAACATC<br>ACCCTGGAGACAGTGTGCCATGATCCCAAGCTGCCTTATCAC<br>GACTTCATCCTGGAAGACGCTGCCTCCCCTAAATGCATTATGA<br>AGAGAAGAAGAAGCCAGGTGAGACATTCTTCATGTGCAGCT<br>GTTCTTCTGATGAGTGCAACGATAACATCATCTTTTCTGAGGA<br>GTACAACACATCCAATCCTGACGTGGAGCCAAAGAGCTCTGAT<br>AAGACCCACACATGCCCTCCATGTCCAGCTCCTGAGCTGCTG<br>GGAGGACCATCCGTGTTCCTGTTTCCACCTAAGCCTAAGGACA<br>CCCTGATGATCTCCAGGACCCCAGAGGTGACATGCGTGGTGG<br>TGGACGTGAGCCACGAGGACCCCGAGGTGAAGTTTAACTGGT<br>ACGTGGATGGCGTGGAGGTGCATAATGCCAAGACCAAGCCAA<br>GGGAGGAGCAGTACAACAGCACCTATCGGGTGGTGTCTGTGC<br>TGACAGTGCTGCATCAGGACTGGCTGAACGGCAAGGAGTATA<br>AGTGCAAGGTGTCTAATAAGGCTCTGCCAGCCCCCATCGAGA<br>AGACCATCTCCAAGGCTAAGGGCCAGCCAAGAGAGCCCCAGG<br>TGTACACACTGCCACCCAGCCGCGACGAGCTGACCAAGAACC<br>AGGTGTCTCTGACATGTCTGGTGAAGGGCTTCTATCCCTCTGA<br>TATCGCTGTGGAGTGGGAGTCCAACGGACAGCCTGAGAACAA<br>TTACAAGACCACACCTCCAGTGCTGGACAGCGATGGCTCTTTC | Nucleic acid sequence encoding T22d35-Fc-IgG1-v2(SCC) in secretable form |

-continued

LISTING OF SEQUENCES

| SEQ ID NO: | Sequence | Description |
|---|---|---|
| | TTTCTGTATTCCAAGCTGACCGTGGATAAGAGCAGGTGGCAGC<br>AGGGCAACGTGTTTTCCTGTAGCGTGATGCATGAGGCCCTGC<br>ACAATCATTACACACAGAAGTCTCTGTCCCTGAGCCCTGGC | |
| 32 | ATGGATTGGACCTGGAGAATCCTGTTCCTGGTGGCTGCTGCTA<br>CCGGAACACACGCTATCCCCCCTCATGTGCAGAAGTCTGTGA<br>ACAATGACATGATCGTGACAGATAACAATGGCGCCGTGAAGTT<br>TCCTCAGCTGTGCAAGTTCTGTGACGTGAGGTTTTCCACCTGC<br>GATAACCAGAAGTCCTGCATGAGCAATTGTTCTATCACATCCA<br>TCTGCGAGAAGCCACAGGAGGTGTGCGTGGCCGTGTGGCGG<br>AAGAACGACGAGAATATCACCCTGGAGACAGTGTGCCACGAT<br>CCTAAGCTGCCATACCATGACTTCATCCTGGAGGATGCTGCCA<br>GCCCCAAGTGTATCATGAAGGAGAAGAAGAAGCCTGGCGAGA<br>CATTCTTCATGTGCTCTTGTTCCAGCGACGAGTGCAACGATAA<br>TATCATCTTCTCCGAGGAGTATAACACCAGCAATCCAGACATC<br>CCACCCCACGTGCAGAAGAGCGTCAATAACGATATGATTGTCA<br>CAGATAACAATGGCGCTGTGAAGITTCCOCAGCTGTGCAAATT<br>TTGTGACGTGAGATTTTCTACCTGTGATAACCAGAAGAGCTGC<br>ATGTCTAATTGTTCCATCACATCTATTTGTGAAAAACCTCAGGA<br>AGTGTGCGTGGCCGTGTGGAGAAAAAATGATGAAAACATCAC<br>CCTGGAGACAGTGTGCCATGATCCCAAGCTGCCTTATCACGA<br>CTTCATCCTGGAAGACGCTGCCTCCCCAAAATGCATTATGAAA<br>GAGAAGAAGAAGCCCGGTGAGACATTCTTCATGTGCAGCTGTT<br>CTTCTGATGAGTGCAACGATAACATCATCTTTTCTGAGGAGTA<br>CAACACATCCAATCCTGACGGAGGAGGCAGCGGAGGAGGCTC<br>TGGAGGCGGCACCCACACATGCCCTCCATGTCCAGCTCCTGA<br>GCTGCTGGGAGGACCTTCCGTGTTCCTGTTTCCCCCTAAGCC<br>AAAGGACACCCTGATGATCTCCAGGACCCCCGAGGTGACATG<br>CGTGGTGGTGGACGTGAGCCACGAGGACCCCGAGGTGAAGT<br>TTAACTGGTACGTGGATGGCGTGGAGGTGCATAATGCCAAGA<br>CCAAGCCAAGGGAGGAGCAGTACAACAGCACCTATCGGGTGG<br>TGTCTGTGCTGACAGTGCTGCATCAGGATTGGCTGAACGGCA<br>AGGAGTATAAGTGCAAGGTGTCTAATAAGGCTCTGCCAGCCC<br>CCATTGAGAAGACCATCTCCAAGGCTAAGGGCCAGCCAAGAG<br>AGCCCCAGGTGTACACACTGCCACCCAGCCGCGACGAGCTGA<br>CCAAGAACCAGGTGTCTCTGACATGTCTGGTGAAGGGCTTCTA<br>TCCTTCTGATATCGCTGTGGAGTGGGAGTCCAACGGACAGCC<br>AGAGAACAATTACAAGACCACACCTCCAGTGCTGGACTCTGAT<br>GGCTCCTTCTTTCTGTATTCCAAGCTGACCGTGGACAAGAGCA<br>GGTGGCAGCAGGGCAACGTGTTTAGCTGTTCTGTGATGCATG<br>AGGCCCTGCACAATCATTACACACAGAAGTCCCTGAGCCTGTC<br>TCCTGGC | Nucleic acid sequence encoding T22d35-Fc-IgG10 v3(GSL-CC) in secretable form |
| 33 | ATGGATTGGACCTGGAGAATCCTCTTCCTTGTAGCAGCAGCAA<br>CAGGTACACATGCTATCCCTCCTCATGTTCAAAAGTCCGTTAA<br>CAACGACATGATCGTCACCGATAACAACGGTGCTGTCAAGTTC<br>CCACAACTCTGTAAGTTCTGCGATGTGCGTTTCTCCACATGTG<br>ATAACCAGAAGTCCTGTATGAGCAACTGCTCAATCACCTCCAT<br>CTGCGAAAAGCCACAAGAGGTATGCGTAGCTGTATGGCGAAA<br>GAACGATGAAAACATCACCCTGGAAACCGTCTGTCACGATCCA<br>AAGCTCCCATACCATGATTTCATCCTGGAAGACGCAGCTTCTC<br>CAAAGTGTATCATGAAGGAGAAGAAGAAGCCCGGTGAAACCTT<br>CTTCATGTGCTCCTGTTCCTCAGATGAATGCAACGATAACATC<br>ATCTTCTCCGAGGAGTACAACACCTCCAACCCAGATATCCCTC<br>CACACGTTCAGAAGTCCGTAAACAATGACATGATTGTGACCGA<br>CAACAACGGGGCTGTTAAGTTCCCACAGCTCTGTAAGTTTTGC<br>GACGTTAGGTTCAGCACCTGTGATAATCAGAAGAGCTGCATGT<br>CCAACTGCAGCATCACCAGTATTTGCGAGAAGCCTCAAGAAGT<br>GTGTGTCGCTGTTTGGAGAAAGAACGACGAAAACATAACCCTG<br>GAGACCGTTTGCCACGATCCAAAACTCCCATATCACGATTTCA<br>TTCTGGAGGACGCCGCCAGTCCTAAATGTATAATGAAAGAGAA<br>GAAGAAACCAGGGGAGACCTTCTTTATGTGCAGCTGCAGCAG<br>CGACGAGTGTAACGATAATATAATTTTTAGCGAGGAGTATAATA<br>CAAGCAATCCCGACGTCGAGTGCCCTCCATGCCCTGCCCCTC<br>CTGTTGCCGGACCTAGTGTGTTTTTGTTTCCTCCTAAACCTAAA<br>GATACACTCATGATTAGCAGGACACCTGAGGTGACATGTGTCG<br>TCGTGGACGTGAGTCATGAAGACCCCGAAGTGCAGTTTAATTG<br>GTATGTCGACGGAGTCGAAGTCCATAATGCCAAAACTAAACCA<br>AGGGAAGAACAGTTTAATTCAACTTTTCGCGTGGTCTCTGTGC<br>TGACTGTGGTGCACCAGGACTGGCTTAATGGAAAGGAATACAA<br>GTGTAAGGTGAGTAATAAGGGCCTGCCCGCCCCCATTGAAAA<br>AACTATTAGTAAGACTAAAGGGCAGCCCCGAGAGCCCCAGGT<br>GTATACTTTGCCCCCCTCTCGGGAGGAGATGACTAAAAATCAG<br>GTGAGTCTTACATGTCTTGTGAAAGGATTTTACCCCTCTGACAT | Nucleic acid sequence encoding T22d357-Fc-IgG2-v2(CC) in secretable form |

LISTING OF SEQUENCES

| SEQ ID NO: | Sequence | Description |
|---|---|---|
| | TTCAGTGGAGTGGGAGTCTAATGGCCAGCCCGAGAATAATTAC AAAACTACTCCCCCATGTTGGACTCTGACGGCTCATTTTTCTT GTACTCTAAACTGACAGTGGACAAAAGTCGGTGGCAGCAGGG CAATGTGTTTTCTTGTTCAGTGATGCACGAGGCCCTGCATAAT CACTATACACAGAAATCTCTGTCTCTGTCACCCGGCTGATGA | |
| 34 | (GGGGS)n | glycine-serine linker (GSL) - may be repeated between 1 and 50 times |
| 35 | ERKCCVECPPCPAPP | amino acid variations in the linker region of the N- and C-terminal FC-fused T22d35 fusions |
| 36 | VECPPCPAPP | amino acid variations in the linker region of the N- and C-terminal FC-fused T22d35 fusions |
| 37 | THTCPPCPAPE | amino acid variations in the linker region of the N- and C-terminal FC-fused T22d35 fusions |
| 38 | VEPKSSDKTHTCPPCPAPE | amino acid variations in the linker region of the N- and C-terminal FC-fused T22d35 fusions |
| 39 | *GGGSGGGSGGG*THTCPPCPAPE | amino acid variations in the linker region of the N- and C-terminal FC-fused T22d35 fusions |
| 40 | PPCPAPE | amino acid variations in the linker region of the N- and C-terminal FC-fused T22d35 fusions |
| 41 | DKTHTCPPCPAPE | amino acid variations in the linker region of the N- and C-terminal FC-fused T22d35 fusions |

-continued

LISTING OF SEQUENCES

| SEQ ID NO: | Sequence | Description |
|---|---|---|
| 42 | VECPPCPAPP | amino acid variations in the linker region of the N- and C-terminal FC-fused T22d35 fusions |

REFERENCES

All patents, patent applications and publications referred to throughout the application are listed below.

Arteaga C L (2006) Inhibition of TGFβeta signaling in cancer therapy. *Curr Opin Genet Dev* 16: 30-37

De Crescenzo G, Grothe S, Zwaagstra J, Tsang M, O'Connor-McCourt M D (2001) Real-time monitoring of the interactions of transforming growth factor-beta (TGF-beta) isoforms with latency-associated protein and the ectodomains of the TGF-beta type II and III receptors reveals different kinetic models and stoichiometries of binding. *J Biol Chem* 276: 29632-29643

Durocher Y, Perret S, Kamen A (2002) High-level and high-throughput recombinant protein production by transient transfection of suspension-growing human 293-EBNA1 cells. *Nucleic Acids Res* 30: E9

Economides A N, Carpenter L R, Rudge J S, Wong V, Koehler-Stec E M, Hartnett C, Pyles E A, Xu X, Daly T J, Young M R, Fandl J P, Lee F, Carver S, McNay J, Bailey K, Ramakanth S, Hutabarat R, Huang T T, Radziejewski C, Yancopoulos G D, Stahl N (2003) Cytokine traps: multi-component, high-affinity blockers of cytokine action. *Nat Med* 9: 47-52

Eisenberg D, Schwarz E, Komaromy M, Wall R (1984) Analysis of membrane and surface protein sequences with the hydrophobic moment plot. *J Mol Biol* 179: 125-142

Gajewski T F (2015) The Next Hurdle in Cancer Immunotherapy: Overcoming the Non-T-Cell-Inflamed Tumor Microenvironment. *Semin Oncol* 42: 663-671

Garberg P, Ball M, Borg N, Cecchelli R, Fenart L, Hurst R D, Lindmark T, Mabondzo A, Nilsson J E, Raub T J, Stanimirovic D, Terasaki T, Oberg J O, Osterberg T (2005) In vitro models for the blood-brain barrier. *Toxicol In Vitro* 19: 299-334

Hahn T, Akporiaye E T (2006) Targeting transforming growth factor beta to enhance cancer immunotherapy. *Curr Oncol* 13: 141-143

Haqqani A S, Caram-Salas N, Ding W, Brunette E, Delaney C E, Baumann E, Boileau E, Stanimirovic D (2013) Multiplexed evaluation of serum and CSF pharmacokinetics of brain-targeting single-domain antibodies using a NanoLC-SRM-ILIS method. *Mol Pharm* 10: 1542-1556

Hawinkels L J, Ten Dijke P (2011) Exploring anti-TGF-beta therapies in cancer and fibrosis. *Growth Factors* 29: 140-152

Holash J, Davis S, Papadopoulos N, Croll S D, Ho L, Russell M, Boland P, Leidich R, Hylton D, Burova E, Ioffe E, Huang T, Radziejewski C, Bailey K, Fandl J P, Daly T, Wiegand S J, Yancopoulos G D, Rudge J S (2002) VEGF-Trap: a VEGF blocker with potent antitumor effects. *Proc Natl Acad Sci USA* 99: 11393-11398

Jin P, Zhang J, Beryt M, Turin L, Brdlik C, Feng Y, Bai X, Liu J, Jorgensen B, Shepard H M (2009) Rational optimization of a bispecific ligand trap targeting EGF receptor family ligands. *Mol Med* 15: 11-20

Li M O, Wan Y Y, Sanjabi S, Robertson A K, Flavell R A (2006) Transforming growth factor-beta regulation of immune responses. *Annu Rev Immunol* 24: 99-146

Massague J, Blain S W, Lo R S (2000) TGFβeta signaling in growth control, cancer, and heritable disorders. *Cell* 103: 295-309

Mourskaia A A, Northey J J, Siegel P M (2007) Targeting aberrant TGF-beta signaling in pre-clinical models of cancer. *Anticancer Agents Med Chem* 7: 504-514

Rodgarkia-Dara C, Vejda S, Erlach N, Losert A, Bursch W, Berger W, Schulte-Hermann R, Grusch M (2006) The activin axis in liver biology and disease. *Mutat Res* 613: 123-137

Santarpia M, Gonzalez-Cao M, Viteri S, Karachaliou N, Altavilla G, Rosell R (2015) Programmed cell death protein-1/programmed cell death ligand-1 pathway inhibition and predictive biomarkers: understanding transforming growth factor-beta role. *Trans/Lung Cancer Res* 4: 728-742

Thiery J P, Acloque H, Huang R Y, Nieto M A (2009) Epithelial-mesenchymal transitions in development and disease. *Cell* 139: 871-890

Wojtowicz-Praga S (2003) Reversal of tumor-induced immunosuppression by TGF-beta inhibitors. *Invest New Drugs* 21: 21-32

Yang L, Pang Y, Moses H L (2010) TGF-beta and immune cells: an important regulatory axis in the tumor microenvironment and progression. *Trends Immunol* 31: 220-227

Yang X, Ambrogelly A (2014) Enlarging the repertoire of therapeutic monoclonal antibodies platforms: domesticating half molecule exchange to produce stable IgG4 and IgG1 bispecific antibodies. *Curr Opin Biotechnol* 30: 225-229

Zheng X, Koropatnick J, Chen D, Velenosi T, Ling H, Zhang X, Jiang N, Navarro B, Ichim T E, Urquhart B, Min W (2013) Silencing IDO in dendritic cells: a novel approach to enhance cancer immunotherapy in a murine breast cancer model. *Int J Cancer* 132: 967-977

Zwaagstra J C, Sulea T, Baardsnes J, Lenferink A E, Collins C, Cantin C, Paul-Roc B, Grothe S, Hossain S, Richer L P, L'Abbe D, Tom R, Cass B, Durocher Y, O'Connor-McCourt M D (2012) Engineering and therapeutic application of single-chain bivalent TGF-beta family traps. *Mol Cancer Ther* 11: 1477-1487

WO/1995/04069
WO/2004/076670
WO 2008/113185
WO 2010/031168

U.S. Pat. No. 8,815,247
U.S. 62/777,375
US2015/0225483
WO01/83525;
WO2005/028517;
WO2008/113185;
WO2008/157367;
WO2010/003118;
WO2010/099219;
WO2012/071649;

WO2012/142515;
WO2013/000234;
U.S. Pat. No. 5,693,607;
US2005/0203022;
US2007/0244042;
U.S. Pat. Nos. 8,318,135;
U.S. Pat. No. 8,658,135;
U.S. Pat. No. 8,815,247;
US2015/0225483; and
US2015/0056199

The invention claimed is:

1. A polypeptide useful to inhibit an effect of a Transforming Growth Factor Beta (TGF-β) isotype, the polypeptide comprising from N-terminus to C-terminus:
   a first region comprising a first TGF-β receptor ectodomain (TβR-ECD) linked to a second TβR-ECD, wherein the C-terminus of the first TβR-ECD is linked to the N-terminus of the second TβR-ECD by a first linker; and
   a second region comprising the second constant domain (CH2) and/or third constant domain (CH3) of an antibody heavy chain, wherein the second region comprises an amino acid sequence selected from the group consisting of SEQ ID NO:12, SEQ ID NO:15, SEQ ID NO:18, and SEQ ID NO:24;
   wherein the N-terminus of the second region is linked to the C-terminus of the first region by a second linker having the amino acid sequence of SEQ ID NO: 8.

2. The polypeptide according to claim 1, wherein the polypeptide comprises an amino acid sequence selected from the group consisting of SEQ ID NO:10, SEQ ID NO:14, SEQ ID NO:17, SEQ ID NO:20, and SEQ ID NO:23.

3. A homodimeric protein comprising a first polypeptide and a second polypeptide each according to claim 1, wherein the first and second polypeptide are linked between respective antibody constant domains by at least one disulfide bridge, and wherein the first polypeptide and the second polypeptide each comprise an amino acid sequence selected from the group consisting of SEQ ID NO:10, SEQ ID NO:14, SEQ ID NO:17, SEQ ID NO:20, and SEQ ID NO:23.

4. The polypeptide according to claim 1, wherein the first linker comprises the amino acid sequence of SEQ ID NO:6.

5. The polypeptide according to claim 4, wherein the first TβR-ECD and the second TβR-ECD each consists of the amino acid sequence of SEQ ID NO:4.

6. The polypeptide according to claim 1, wherein each of the first and second TβR-ECD comprises the amino acid sequence of SEQ ID NO: 4.

7. A pharmaceutical composition comprising the polypeptide of claim 1 and a pharmaceutically-acceptable carrier, diluent, or excipient.

8. A pharmaceutical composition comprising the homodimeric protein of claim 3 and a pharmaceutically acceptable carrier.

9. A polypeptide comprising the amino acid sequence of SEQ ID NO:14.

10. A protein comprising two polypeptides of claim 9, wherein the protein is a homodimer.

11. A pharmaceutical composition comprising the polypeptide of claim 9 and a pharmaceutically-acceptable carrier, diluent, or excipient.

12. A polypeptide comprising from N-terminus to C-terminus: (i) an amino acid sequence consisting of the amino acid sequence of SEQ ID NO:5; and (ii) the Fc region of an antibody heavy chain.

13. The polypeptide of claim 12, wherein the Fc region is the Fc region of an IgG1 antibody.

14. A pharmaceutical composition comprising the polypeptide of claim 12 and a pharmaceutically-acceptable carrier, diluent, or excipient.

15. A nucleic acid molecule encoding the polypeptide of claim 1.

16. A vector comprising the nucleic acid molecule of claim 15.

17. The nucleic acid molecule according to claim 15, wherein the nucleic acid molecule encodes a polypeptide comprising an amino acid sequence selected from the group consisting of SEQ ID NO:10, SEQ ID NO:14, SEQ ID NO:17, SEQ ID NO:20, and SEQ ID NO:23.

18. The nucleic acid molecule according to claim 17, wherein the nucleic acid molecule comprises a nucleotide sequence selected from the group consisting of SEQ ID NO:29, SEQ ID NO:30, SEQ ID NO:31, SEQ ID NO:32, and SEQ ID NO:33.

19. A host cell comprising the nucleic acid molecule of claim 17 or a vector comprising the nucleic acid molecule of claim 15.

20. A method for producing a polypeptide, wherein the method comprises culturing the host cell of claim 19 and recovering the polypeptide.

21. A method of manufacturing the polypeptide of claim 1, comprising culturing a host cell comprising a nucleic acid molecule encoding the polypeptide under conditions suitable for protein expression; and harvesting the polypeptide.

22. The method of manufacturing according to claim 1, wherein the polypeptide comprises the amino acid sequence of SEQ ID NO:14.

23. A nucleic acid molecule encoding the polypeptide of claim 12.

24. A vector comprising the nucleic acid molecule of claim 23.

25. A host cell comprising the nucleic acid molecule of claim 23 or a vector comprising the nucleic acid molecule of claim 23.

26. A method for producing a polypeptide, wherein the method comprises culturing the host cell of claim 25 in a culture medium and recovering the polypeptide from the culture medium.

27. A method of manufacturing a polypeptide comprising culturing the host cell of claim 25 under conditions suitable for protein expression; and harvesting the polypeptide.

28. A method for treating a medical condition, disease or disorder associated with over-expression of ligands of the TGF-β superfamily in a subject, comprising administering to the subject the polypeptide of claim 1.

29. The method according to claim 28, wherein the medical condition, disease or disorder is a cancer, an ocular disease, a fibrotic disease, or a genetic disorder of connective tissue.

30. The method according to claim 28, wherein the polypeptide inhibits TGF-β1 isotype and TGF-β3 isotype and wherein the polypeptide comprises an amino acid sequence selected from the group consisting of SEQ ID NO:10, SEQ ID NO:14, SEQ ID NO:17, SEQ ID NO:20, and SEQ ID NO:23.

31. The method according to claim 30, wherein the polypeptide comprises the amino acid sequence of SEQ ID NO: 14.

32. A method for treating cancer associated with over-expression or over-activation of ligands of the TGF-β superfamily in a subject comprising administering to the subject the polypeptide of claim and an immunotherapeutic agent.

33. The method according to claim 32, wherein the polypeptide inhibits TGF-β1 isotype and TGF-β3 isotype and wherein the polypeptide comprises the amino acid sequence of SEQ ID NO: 14.

34. A method for treating a medical condition, disease or disorder associated with over-activation of ligands of the TGF-β superfamily in a subject, comprising administering to the subject the polypeptide of claim 12.

35. The method according to claim 34, wherein the polypeptide inhibits TGF-β1 isotype and TGF-β3 isotype and wherein the polypeptide comprises an amino acid sequence selected from the group consisting of SEQ ID NO:10, SEQ ID NO:14, SEQ ID NO:17, SEQ ID NO:20, and SEQ ID NO:23.

36. The method according to claim 35, wherein the polypeptide comprises the amino acid sequence of SEQ ID NO: 14.

37. The method according to claim 34, wherein the medical condition, disease or disorder is a cancer, an ocular disease, a fibrotic disease, or a genetic disorder of connective tissue.

38. A method for treating a medical condition, disease or disorder associated with perturbation of members of the TGF-β superfamily or its ligands in a subject, comprising administering to the subject the polypeptide of claim 9.

39. The method according to claim 38, wherein the polypeptide inhibits TGF-β1 isotype and TGF-β3 isotype.

40. The method according to claim 38, wherein the medical condition, disease or disorder is a cancer.

41. A method treating a medical condition, disease or disorder associated with over-expression of ligands of the TGF-β superfamily in a subject, comprising administering to the subject the homodimeric protein of claim 3.

42. A method treating a medical condition, disease or disorder associated with over-activation of ligands of the TGF-β superfamily in a subject, comprising administering to the subject the homodimeric protein of claim 3.

43. A method for inhibiting TGFβ comprising contacting the polypeptide of claim 1 to a sample containing a TGFβ isotype.

\* \* \* \* \*

```
                        SEQUENCE LISTING

<160> NUMBER OF SEQ ID NOS: 42

<210> SEQ ID NO 1
<211> LENGTH: 136
<212> TYPE: PRT
<213> ORGANISM: Artificial Sequence
<220> FEATURE:
<223> OTHER INFORMATION: T RII-ECD including the structure domain and
      its natural linkers (also termed T2m)

<400> SEQUENCE: 1

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 2
<211> LENGTH: 126
<212> TYPE: PRT
<213> ORGANISM: Artificial Sequence
<220> FEATURE:
<223> OTHER INFORMATION: T RII-ECD structured domain with its natural N-
      terminal linker

<400> SEQUENCE: 2

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80
```

```
Pro Lys Leu Pro Tyr His Asp Phe Ile Leu Glu Asp Ala Ala Ser Pro
            85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe
            115                 120                 125

<210> SEQ ID NO 3
<211> LENGTH: 111
<212> TYPE: PRT
<213> ORGANISM: Artificial Sequence
<220> FEATURE:
<223> OTHER INFORMATION: T RII-ECD structured domain with its with
      natural C-terminal linker

<400> SEQUENCE: 3

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
            35                  40                  45

Leu Glu Thr Val Cys His Asp Pro Lys Leu Pro Tyr His Asp Phe Ile
        50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe Ser Glu Gly Tyr Asn Thr Ser Asn Pro Asp
            100                 105                 110

<210> SEQ ID NO 4
<211> LENGTH: 101
<212> TYPE: PRT
<213> ORGANISM: Artificial Sequence
<220> FEATURE:
<223> OTHER INFORMATION: T RII-ECD structured domain

<400> SEQUENCE: 4

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
            35                  40                  45

Leu Glu Thr Val Cys His Asp Pro Lys Leu Pro Tyr His Asp Phe Ile
        50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100

<210> SEQ ID NO 5
<211> LENGTH: 272
<212> TYPE: PRT
<213> ORGANISM: Artificial Sequence
```

<220> FEATURE:
<223> OTHER INFORMATION: T RII-ECD- T RII-ECD fused dimer including structured domains and natural linkers (also termed T22d35)

<400> SEQUENCE: 5

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Ile Pro Pro His Val Gln Lys Ser
    130                 135                 140

Val Asn Asn Asp Met Ile Val Thr Asp Asn Asn Gly Ala Val Lys Phe
145                 150                 155                 160

Pro Gln Leu Cys Lys Phe Cys Asp Val Arg Phe Ser Thr Cys Asp Asn
                165                 170                 175

Gln Lys Ser Cys Met Ser Asn Cys Ser Ile Thr Ser Ile Cys Glu Lys
            180                 185                 190

Pro Gln Glu Val Cys Val Ala Val Trp Arg Lys Asn Asp Glu Asn Ile
        195                 200                 205

Thr Leu Glu Thr Val Cys His Asp Pro Lys Leu Pro Tyr His Asp Phe
    210                 215                 220

Ile Leu Glu Asp Ala Ala Ser Pro Lys Cys Ile Met Lys Glu Lys Lys
225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
            260                 265                 270

<210> SEQ ID NO 6
<211> LENGTH: 34
<212> TYPE: PRT
<213> ORGANISM: Artificial Sequence
<220> FEATURE:
<223> OTHER INFORMATION: T RII-ECD natural linker

<400> SEQUENCE: 6

Ser Glu Glu Tyr Asn Thr Ser Asn Pro Asp Ile Pro Pro His Val Gln
1               5                   10                  15

Lys Ser Val Asn Asn Asp Met Ile Val Thr Asp Asn Asn Gly Ala Val
            20                  25                  30

Lys Phe

```
<210> SEQ ID NO 7
<211> LENGTH: 24
<212> TYPE: PRT
<213> ORGANISM: Artificial Sequence
<220> FEATURE:
<223> OTHER INFORMATION: T RII-ECD N-terminal natural linker

<400> SEQUENCE: 7

Ile Pro Pro His Val Gln Lys Ser Val Asn Asn Asp Met Ile Val Thr
1               5                   10                  15

Asp Asn Asn Gly Ala Val Lys Phe
            20

<210> SEQ ID NO 8
<211> LENGTH: 10
<212> TYPE: PRT
<213> ORGANISM: Artificial Sequence
<220> FEATURE:
<223> OTHER INFORMATION: T RII-ECD C-terminal natural linker

<400> SEQUENCE: 8

Ser Glu Glu Tyr Asn Thr Ser Asn Pro Asp
1               5                   10

<210> SEQ ID NO 9
<211> LENGTH: 363
<212> TYPE: PRT
<213> ORGANISM: Artificial Sequence
<220> FEATURE:
<223> OTHER INFORMATION: T2m-Fc fusion of T2m with the hIgG2Fc(CCCC) Fc
      region

<400> SEQUENCE: 9

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Glu Arg Lys Cys Cys Val Glu Cys
    130                 135                 140

Pro Pro Cys Pro Ala Pro Pro Val Ala Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Gln Phe
            180                 185                 190

Asn Trp Tyr Val Asp Gly Val Glu Val His Asn Ala Lys Thr Lys Pro
        195                 200                 205
```

```
Arg Glu Glu Gln Phe Asn Ser Thr Phe Arg Val Val Ser Val Leu Thr
    210                 215                 220
Val Val His Gln Asp Trp Leu Asn Gly Lys Glu Tyr Lys Cys Lys Val
225                 230                 235                 240
Ser Asn Lys Gly Leu Pro Ala Pro Ile Glu Lys Thr Ile Ser Lys Thr
                245                 250                 255
Lys Gly Gln Pro Arg Glu Pro Gln Val Tyr Thr Leu Pro Pro Ser Arg
            260                 265                 270
Glu Glu Met Thr Lys Asn Gln Val Ser Leu Thr Cys Leu Val Lys Gly
        275                 280                 285
Phe Tyr Pro Ser Asp Ile Ser Val Glu Trp Glu Ser Asn Gly Gln Pro
290                 295                 300
Glu Asn Asn Tyr Lys Thr Thr Pro Pro Met Leu Asp Ser Asp Gly Ser
305                 310                 315                 320
Phe Phe Leu Tyr Ser Lys Leu Thr Val Asp Lys Ser Arg Trp Gln Gln
                325                 330                 335
Gly Asn Val Phe Ser Cys Ser Val Met His Glu Ala Leu His Asn His
            340                 345                 350
Tyr Thr Gln Lys Ser Leu Ser Leu Ser Pro Gly
        355                 360

<210> SEQ ID NO 10
<211> LENGTH: 499
<212> TYPE: PRT
<213> ORGANISM: Artificial Sequence
<220> FEATURE:
<223> OTHER INFORMATION: T22d35-Fc fusion of T22d35 with the
      hIgG2Fc(CCCC) Fc region

<400> SEQUENCE: 10

Ile Pro Pro His Val Gln Lys Ser Val Asn Asn Asp Met Ile Val Thr
1               5                   10                  15
Asp Asn Asn Gly Ala Val Lys Phe Pro Gln Leu Cys Lys Phe Cys Asp
            20                  25                  30
Val Arg Phe Ser Thr Cys Asp Asn Gln Lys Ser Cys Met Ser Asn Cys
        35                  40                  45
Ser Ile Thr Ser Ile Cys Glu Lys Pro Gln Glu Val Cys Val Ala Val
    50                  55                  60
Trp Arg Lys Asn Asp Glu Asn Ile Thr Leu Glu Thr Val Cys His Asp
65                  70                  75                  80
Pro Lys Leu Pro Tyr His Asp Phe Ile Leu Glu Asp Ala Ala Ser Pro
                85                  90                  95
Lys Cys Ile Met Lys Glu Lys Lys Pro Gly Glu Thr Phe Phe Met
            100                 105                 110
Cys Ser Cys Ser Ser Asp Glu Cys Asn Asp Asn Ile Ile Phe Ser Glu
        115                 120                 125
Glu Tyr Asn Thr Ser Asn Pro Asp Ile Pro His Val Gln Lys Ser
    130                 135                 140
Val Asn Asn Asp Met Ile Val Thr Asp Asn Asn Gly Ala Val Lys Phe
145                 150                 155                 160
Pro Gln Leu Cys Lys Phe Cys Asp Val Arg Phe Ser Thr Cys Asp Asn
                165                 170                 175
Gln Lys Ser Cys Met Ser Asn Cys Ser Ile Thr Ser Ile Cys Glu Lys
            180                 185                 190
Pro Gln Glu Val Cys Val Ala Val Trp Arg Lys Asn Asp Glu Asn Ile
        195                 200                 205
```

Thr Leu Glu Thr Val Cys His Asp Pro Lys Leu Pro Tyr His Asp Phe
    210                 215                 220

Ile Leu Glu Asp Ala Ala Ser Pro Lys Cys Ile Met Lys Glu Lys Lys
225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
                260                 265                 270

Glu Arg Lys Cys Cys Val Glu Cys Pro Pro Cys Pro Ala Pro Pro Val
            275                 280                 285

Ala Gly Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

His Glu Asp Pro Glu Val Gln Phe Asn Trp Tyr Val Asp Gly Val Glu
                325                 330                 335

Val His Asn Ala Lys Thr Lys Pro Arg Glu Glu Gln Phe Asn Ser Thr
            340                 345                 350

Phe Arg Val Val Ser Val Leu Thr Val Val His Gln Asp Trp Leu Asn
        355                 360                 365

Gly Lys Glu Tyr Lys Cys Lys Val Ser Asn Lys Gly Leu Pro Ala Pro
370                 375                 380

Ile Glu Lys Thr Ile Ser Lys Thr Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ser Val
            420                 425                 430

Glu Trp Glu Ser Asn Gly Gln Pro Glu Asn Asn Tyr Lys Thr Thr Pro
        435                 440                 445

Pro Met Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 11
<211> LENGTH: 19
<212> TYPE: PRT
<213> ORGANISM: Artificial Sequence
<220> FEATURE:
<223> OTHER INFORMATION: signal peptide

<400> SEQUENCE: 11

Met Asp Trp Thr Trp Arg Ile Leu Phe Leu Val Ala Ala Thr Gly
1               5                   10                  15

Thr His Ala

<210> SEQ ID NO 12
<211> LENGTH: 227
<212> TYPE: PRT
<213> ORGANISM: Artificial Sequence
<220> FEATURE:
<223> OTHER INFORMATION: hIgG2Fc(CCCC) Fc region variant

```
<400> SEQUENCE: 12

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 13
<211> LENGTH: 25
<212> TYPE: PRT
<213> ORGANISM: Artificial Sequence
<220> FEATURE:
<223> OTHER INFORMATION: T22d35-Fc  natural linker with the
      hIgG2Fc(CCCC) hinge region

<400> SEQUENCE: 13

Ser Glu Glu Tyr Asn Thr Ser Asn Pro Asp Glu Arg Lys Cys Cys Val
1               5                   10                  15

Glu Cys Pro Pro Cys Pro Ala Pro Pro
            20                  25

<210> SEQ ID NO 14
<211> LENGTH: 496
<212> TYPE: PRT
<213> ORGANISM: Artificial Sequence
<220> FEATURE:
<223> OTHER INFORMATION: T22d35-Fc-IgG1-v1(CC) fusion  of T22d35 with
      the hIgG1Fc(CC) Fc region
```

<400> SEQUENCE: 14

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Ile Pro Pro His Val Gln Lys Ser
    130                 135                 140

Val Asn Asn Asp Met Ile Val Thr Asp Asn Asn Gly Ala Val Lys Phe
145                 150                 155                 160

Pro Gln Leu Cys Lys Phe Cys Asp Val Arg Phe Ser Thr Cys Asp Asn
                165                 170                 175

Gln Lys Ser Cys Met Ser Asn Cys Ser Ile Thr Ser Ile Cys Glu Lys
            180                 185                 190

Pro Gln Glu Val Cys Val Ala Val Trp Arg Lys Asn Asp Glu Asn Ile
        195                 200                 205

Thr Leu Glu Thr Val Cys His Asp Pro Lys Leu Pro Tyr His Asp Phe
    210                 215                 220

Ile Leu Glu Asp Ala Ala Ser Pro Lys Cys Ile Met Lys Glu Lys Lys
225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
            260                 265                 270

Thr His Thr Cys Pro Pro Cys Pro Ala Pro Glu Leu Leu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415
```

```
Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
            485                 490                 495

<210> SEQ ID NO 15
<211> LENGTH: 224
<212> TYPE: PRT
<213> ORGANISM: Artificial Sequence
<220> FEATURE:
<223> OTHER INFORMATION: hIgG1Fc(CC) Fc region variant

<400> SEQUENCE: 15

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
210                 215                 220

<210> SEQ ID NO 16
<211> LENGTH: 21
<212> TYPE: PRT
<213> ORGANISM: Artificial Sequence
<220> FEATURE:
<223> OTHER INFORMATION: T22d35-Fc-IgG1-v1(CC) natural linker with the
      hIgG1Fc(CC) hinge region
```

```
<400> SEQUENCE: 16

Ser Glu Glu Tyr Asn Thr Ser Asn Pro Asp Thr His Thr Cys Pro Pro
1               5                   10                  15

Cys Pro Ala Pro Glu
            20

<210> SEQ ID NO 17
<211> LENGTH: 504
<212> TYPE: PRT
<213> ORGANISM: Artificial Sequence
<220> FEATURE:
<223> OTHER INFORMATION: T22d35-Fc-IgG1-v2(SCC) fusion  of T22d35 with
      the hIgG1Fc(SCC) Fc region

<400> SEQUENCE: 17

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Ile Pro Pro His Val Gln Lys Ser
130                 135                 140

Val Asn Asn Asp Met Ile Val Thr Asp Asn Asn Gly Ala Val Lys Phe
145                 150                 155                 160

Pro Gln Leu Cys Lys Phe Cys Asp Val Arg Phe Ser Thr Cys Asp Asn
                165                 170                 175

Gln Lys Ser Cys Met Ser Asn Cys Ser Ile Thr Ser Ile Cys Glu Lys
            180                 185                 190

Pro Gln Glu Val Cys Val Ala Val Trp Arg Lys Asn Asp Glu Asn Ile
        195                 200                 205

Thr Leu Glu Thr Val Cys His Asp Pro Lys Leu Pro Tyr His Asp Phe
210                 215                 220

Ile Leu Glu Asp Ala Ala Ser Pro Lys Cys Ile Met Lys Glu Lys Lys
225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
            260                 265                 270

Val Glu Pro Lys Ser Ser Asp Lys Thr His Thr Cys Pro Pro Cys Pro
        275                 280                 285

Ala Pro Glu Leu Leu Gly Gly Pro Ser Val Phe Leu Phe Pro Pro Lys
290                 295                 300

Pro Lys Asp Thr Leu Met Ile Ser Arg Thr Pro Glu Val Thr Cys Val
305                 310                 315                 320
```

```
Val Val Asp Val Ser His Glu Asp Pro Glu Val Lys Phe Asn Trp Tyr
            325                 330                 335

Val Asp Gly Val Glu Val His Asn Ala Lys Thr Lys Pro Arg Glu Glu
        340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly
            500

<210> SEQ ID NO 18
<211> LENGTH: 232
<212> TYPE: PRT
<213> ORGANISM: Artificial Sequence
<220> FEATURE:
<223> OTHER INFORMATION: hIgG1Fc(SCC) Fc region variant

<400> SEQUENCE: 18

Val Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175
```

```
Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly
225                 230

<210> SEQ ID NO 19
<211> LENGTH: 29
<212> TYPE: PRT
<213> ORGANISM: Artificial Sequence
<220> FEATURE:
<223> OTHER INFORMATION: T22d35-Fc-IgG1-v2(SCC) natural linker with the
      hIgG1Fc(SCC) hinge region

<400> SEQUENCE: 19

Ser Glu Glu Tyr Asn Thr Ser Asn Pro Asp Val Glu Pro Lys Ser Ser
1               5                   10                  15

Asp Lys Thr His Thr Cys Pro Pro Cys Pro Ala Pro Glu
            20                  25

<210> SEQ ID NO 20
<211> LENGTH: 507
<212> TYPE: PRT
<213> ORGANISM: Artificial Sequence
<220> FEATURE:
<223> OTHER INFORMATION: T22d35-Fc-IgG1-v3(GSL-CC) fusion of T22d35
      with the hIgG1Fc(CC) Fc region and including an artificial GS
      linker

<400> SEQUENCE: 20

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Ile Pro His Val Gln Lys Ser
        130                 135                 140

Val Asn Asn Asp Met Ile Val Thr Asp Asn Asn Gly Ala Val Lys Phe
145                 150                 155                 160

Pro Gln Leu Cys Lys Phe Cys Asp Val Arg Phe Ser Thr Cys Asp Asn
                165                 170                 175

Gln Lys Ser Cys Met Ser Asn Cys Ser Ile Thr Ser Ile Cys Glu Lys
            180                 185                 190

Pro Gln Glu Val Cys Val Ala Val Trp Arg Lys Asn Asp Glu Asn Ile
        195                 200                 205
```

Thr Leu Glu Thr Val Cys His Asp Pro Lys Leu Pro Tyr His Asp Phe
210                 215                 220

Ile Leu Glu Asp Ala Ala Ser Pro Lys Cys Ile Met Lys Glu Lys Lys
225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
                260                 265                 270

Gly Gly Gly Ser Gly Gly Gly Ser Gly Gly Gly Thr His Thr Cys Pro
            275                 280                 285

Pro Cys Pro Ala Pro Glu Leu Leu Gly Gly Pro Ser Val Phe Leu Phe
290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
                340                 345                 350

Arg Glu Glu Gln Tyr Asn Ser Thr Tyr Arg Val Val Ser Val Leu Thr
            355                 360                 365

Val Leu His Gln Asp Trp Leu Asn Gly Lys Glu Tyr Lys Cys Lys Val
370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Asp Glu Leu Thr Lys Asn Gln Val Ser Leu Thr Cys Leu Val Lys Gly
                420                 425                 430

Phe Tyr Pro Ser Asp Ile Ala Val Glu Trp Glu Ser Asn Gly Gln Pro
            435                 440                 445

Glu Asn Asn Tyr Lys Thr Thr Pro Pro Val Leu Asp Ser Asp Gly Ser
        450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly
            500                 505

<210> SEQ ID NO 21
<211> LENGTH: 11
<212> TYPE: DNA
<213> ORGANISM: Artificial Sequence
<220> FEATURE:
<223> OTHER INFORMATION: Artificial GS linker of the T22d35-Fc-IgG1-
     v3(GSL-CC) fusion

<400> SEQUENCE: 21
gggsgggsgg g                                                          11

<210> SEQ ID NO 22
<211> LENGTH: 32
<212> TYPE: PRT
<213> ORGANISM: Artificial Sequence
<220> FEATURE:
<223> OTHER INFORMATION: T22d35-Fc-IgG1-v3(GSL-CC) linker including
     natural and artificial sequences and hIgG1Fc(CC) hinge region

<400> SEQUENCE: 22

| Ser | Glu | Glu | Tyr | Asn | Thr | Ser | Asn | Pro | Asp | Gly | Gly | Ser | Gly | Gly |
|---|---|---|---|---|---|---|---|---|---|---|---|---|---|---|
| 1 | | | | 5 | | | | | 10 | | | | | 15 |

| Gly | Ser | Gly | Gly | Gly | Thr | His | Thr | Cys | Pro | Pro | Cys | Pro | Ala | Pro | Glu |
|---|---|---|---|---|---|---|---|---|---|---|---|---|---|---|---|
| | | | 20 | | | | | 25 | | | | | 30 | | |

<210> SEQ ID NO 23
<211> LENGTH: 494
<212> TYPE: PRT
<213> ORGANISM: Artificial Sequence
<220> FEATURE:
<223> OTHER INFORMATION: T22d35-Fc-IgG2-v2(CC) fusion of T22d35 with
      the hIgG2Fc(CC) Fc region

<400> SEQUENCE: 23

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Ile Pro Pro His Val Gln Lys Ser
    130                 135                 140

Val Asn Asn Asp Met Ile Val Thr Asp Asn Asn Gly Ala Val Lys Phe
145                 150                 155                 160

Pro Gln Leu Cys Lys Phe Cys Asp Val Arg Phe Ser Thr Cys Asp Asn
                165                 170                 175

Gln Lys Ser Cys Met Ser Asn Cys Ser Ile Thr Ser Ile Cys Glu Lys
            180                 185                 190

Pro Gln Glu Val Cys Val Ala Val Trp Arg Lys Asn Asp Glu Asn Ile
        195                 200                 205

Thr Leu Glu Thr Val Cys His Asp Pro Lys Leu Pro Tyr His Asp Phe
210                 215                 220

Ile Leu Glu Asp Ala Ala Ser Pro Lys Cys Ile Met Lys Glu Lys Lys
225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
            260                 265                 270

Val Glu Cys Pro Pro Cys Pro Ala Pro Val Ala Gly Pro Ser Val
        275                 280                 285

Phe Leu Phe Pro Pro Lys Pro Lys Asp Thr Leu Met Ile Ser Arg Thr
290                 295                 300

Pro Glu Val Thr Cys Val Val Val Asp Val Ser His Glu Asp Pro Glu
305                 310                 315                 320

```
Val Gln Phe Asn Trp Tyr Val Asp Gly Val Glu Val His Asn Ala Lys
                325                 330                 335

Thr Lys Pro Arg Glu Glu Gln Phe Asn Ser Thr Phe Arg Val Val Ser
            340                 345                 350

Val Leu Thr Val Val His Gln Asp Trp Leu Asn Gly Lys Glu Tyr Lys
        355                 360                 365

Cys Lys Val Ser Asn Lys Gly Leu Pro Ala Pro Ile Glu Lys Thr Ile
    370                 375                 380

Ser Lys Thr Lys Gly Gln Pro Arg Glu Pro Gln Val Tyr Thr Leu Pro
385                 390                 395                 400

Pro Ser Arg Glu Glu Met Thr Lys Asn Gln Val Ser Leu Thr Cys Leu
                405                 410                 415

Val Lys Gly Phe Tyr Pro Ser Asp Ile Ser Val Glu Trp Glu Ser Asn
            420                 425                 430

Gly Gln Pro Glu Asn Asn Tyr Lys Thr Thr Pro Pro Met Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly
                485                 490

<210> SEQ ID NO 24
<211> LENGTH: 222
<212> TYPE: PRT
<213> ORGANISM: Artificial Sequence
<220> FEATURE:
<223> OTHER INFORMATION: hIgG2Fc(CC) Fc region variant

<400> SEQUENCE: 24

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190
```

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly
    210                 215                 220

<210> SEQ ID NO 25
<211> LENGTH: 20
<212> TYPE: PRT
<213> ORGANISM: Artificial Sequence
<220> FEATURE:
<223> OTHER INFORMATION: T22d35-Fc-IgG2-v2(CC) natural linker with the
      hIgG2Fc(CC) hinge region

<400> SEQUENCE: 25

Ser Glu Glu Tyr Asn Thr Ser Asn Pro Asp Val Glu Cys Pro Pro Cys
1               5                   10                  15

Pro Ala Pro Pro
            20

<210> SEQ ID NO 26
<211> LENGTH: 492
<212> TYPE: PRT
<213> ORGANISM: Artificial Sequence
<220> FEATURE:
<223> OTHER INFORMATION: hIgG1Fc?K(C)-T22d35

<400> SEQUENCE: 26

Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
            35                  40                  45

Phe Asn Trp Tyr Val Asp Gly Val Glu Val His Asn Ala Lys Thr Lys
        50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Arg Asp Glu Leu Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Ile Pro Pro His
    210                 215                 220

Val Gln Lys Ser Val Asn Asn Asp Met Ile Val Thr Asp Asn Asn Gly
225                 230                 235                 240

Ala Val Lys Phe Pro Gln Leu Cys Lys Phe Cys Asp Val Arg Phe Ser
               245                 250                 255

Thr Cys Asp Asn Gln Lys Ser Cys Met Ser Asn Cys Ser Ile Thr Ser
        260                 265                 270

Ile Cys Glu Lys Pro Gln Glu Val Cys Val Ala Val Trp Arg Lys Asn
    275                 280                 285

Asp Glu Asn Ile Thr Leu Glu Thr Val Cys His Asp Pro Lys Leu Pro
290                 295                 300

Tyr His Asp Phe Ile Leu Glu Asp Ala Ala Ser Pro Lys Cys Ile Met
305                 310                 315                 320

Lys Glu Lys Lys Lys Pro Gly Glu Thr Phe Phe Met Cys Ser Cys Ser
                325                 330                 335

Ser Asp Glu Cys Asn Asp Asn Ile Ile Phe Ser Glu Glu Tyr Asn Thr
            340                 345                 350

Ser Asn Pro Asp Ile Pro Pro His Val Gln Lys Ser Val Asn Asn Asp
        355                 360                 365

Met Ile Val Thr Asp Asn Asn Gly Ala Val Lys Phe Pro Gln Leu Cys
    370                 375                 380

Lys Phe Cys Asp Val Arg Phe Ser Thr Cys Asp Asn Gln Lys Ser Cys
385                 390                 395                 400

Met Ser Asn Cys Ser Ile Thr Ser Ile Cys Glu Lys Pro Gln Glu Val
                405                 410                 415

Cys Val Ala Val Trp Arg Lys Asn Asp Glu Asn Ile Thr Leu Glu Thr
            420                 425                 430

Val Cys His Asp Pro Lys Leu Pro Tyr His Asp Phe Ile Leu Glu Asp
        435                 440                 445

Ala Ala Ser Pro Lys Cys Ile Met Lys Glu Lys Lys Lys Pro Gly Glu
    450                 455                 460

Thr Phe Phe Met Cys Ser Cys Ser Ser Asp Glu Cys Asn Asp Asn Ile
465                 470                 475                 480

Ile Phe Ser Glu Glu Tyr Asn Thr Ser Asn Pro Asp
                485                 490

<210> SEQ ID NO 27
<211> LENGTH: 498
<212> TYPE: PRT
<213> ORGANISM: Artificial Sequence
<220> FEATURE:
<223> OTHER INFORMATION: hIgG1Fc?K(CC)-T22d35

<400> SEQUENCE: 27

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ile Pro Pro His Val Gln Lys Ser Val Asn Asn Asp Met Ile
225                 230                 235                 240

Val Thr Asp Asn Asn Gly Ala Val Lys Phe Pro Gln Leu Cys Lys Phe
                245                 250                 255

Cys Asp Val Arg Phe Ser Thr Cys Asp Asn Gln Lys Ser Cys Met Ser
            260                 265                 270

Asn Cys Ser Ile Thr Ser Ile Cys Glu Lys Pro Gln Glu Val Cys Val
        275                 280                 285

Ala Val Trp Arg Lys Asn Asp Glu Asn Ile Thr Leu Glu Thr Val Cys
    290                 295                 300

His Asp Pro Lys Leu Pro Tyr His Asp Phe Ile Leu Glu Asp Ala Ala
305                 310                 315                 320

Ser Pro Lys Cys Ile Met Lys Glu Lys Lys Pro Gly Glu Thr Phe
                325                 330                 335

Phe Met Cys Ser Cys Ser Ser Asp Glu Cys Asn Asp Asn Ile Ile Phe
            340                 345                 350

Ser Glu Glu Tyr Asn Thr Ser Asn Pro Asp Ile Pro Pro His Val Gln
        355                 360                 365

Lys Ser Val Asn Asn Asp Met Ile Val Thr Asp Asn Asn Gly Ala Val
    370                 375                 380

Lys Phe Pro Gln Leu Cys Lys Phe Cys Asp Val Arg Phe Ser Thr Cys
385                 390                 395                 400

Asp Asn Gln Lys Ser Cys Met Ser Asn Cys Ser Ile Thr Ser Ile Cys
                405                 410                 415

Glu Lys Pro Gln Glu Val Cys Val Ala Val Trp Arg Lys Asn Asp Glu
            420                 425                 430

Asn Ile Thr Leu Glu Thr Val Cys His Asp Pro Lys Leu Pro Tyr His
        435                 440                 445

Asp Phe Ile Leu Glu Asp Ala Ala Ser Pro Lys Cys Ile Met Lys Glu
    450                 455                 460

Lys Lys Pro Gly Glu Thr Phe Phe Met Cys Ser Cys Ser Ser Asp
465                 470                 475                 480

Glu Cys Asn Asp Asn Ile Ile Phe Ser Glu Glu Tyr Asn Thr Ser Asn
                485                 490                 495

Pro Asp

<210> SEQ ID NO 28
<211> LENGTH: 494
<212> TYPE: PRT
<213> ORGANISM: Artificial Sequence
<220> FEATURE:
<223> OTHER INFORMATION: hIgG2Fc?K(CC)-T22d35

<400> SEQUENCE: 28

```
Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
                35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Ile Pro
    210                 215                 220

Pro His Val Gln Lys Ser Val Asn Asn Asp Met Ile Val Thr Asp Asn
225                 230                 235                 240

Asn Gly Ala Val Lys Phe Pro Gln Leu Cys Lys Phe Cys Asp Val Arg
                245                 250                 255

Phe Ser Thr Cys Asp Asn Gln Lys Ser Cys Met Ser Asn Cys Ser Ile
            260                 265                 270

Thr Ser Ile Cys Glu Lys Pro Gln Glu Val Cys Val Ala Val Trp Arg
        275                 280                 285

Lys Asn Asp Glu Asn Ile Thr Leu Glu Thr Val Cys His Asp Pro Lys
    290                 295                 300

Leu Pro Tyr His Asp Phe Ile Leu Glu Asp Ala Ala Ser Pro Lys Cys
305                 310                 315                 320

Ile Met Lys Glu Lys Lys Lys Pro Gly Glu Thr Phe Phe Met Cys Ser
                325                 330                 335

Cys Ser Ser Asp Glu Cys Asn Asp Asn Ile Ile Phe Ser Glu Glu Tyr
            340                 345                 350

Asn Thr Ser Asn Pro Asp Ile Pro Pro His Val Gln Lys Ser Val Asn
        355                 360                 365

Asn Asp Met Ile Val Thr Asp Asn Asn Gly Ala Val Lys Phe Pro Gln
    370                 375                 380

Leu Cys Lys Phe Cys Asp Val Arg Phe Ser Thr Cys Asp Asn Gln Lys
385                 390                 395                 400
```

```
Ser Cys Met Ser Asn Cys Ser Ile Thr Ser Ile Cys Glu Lys Pro Gln
                405                 410                 415

Glu Val Cys Val Ala Val Trp Arg Lys Asn Asp Glu Asn Ile Thr Leu
            420                 425                 430

Glu Thr Val Cys His Asp Pro Lys Leu Pro Tyr His Asp Phe Ile Leu
        435                 440                 445

Glu Asp Ala Ala Ser Pro Lys Cys Ile Met Leu Glu Lys Lys Lys Pro
    450                 455                 460

Gly Glu Thr Phe Phe Met Cys Ser Cys Ser Ser Asp Glu Cys Asn Asp
465                 470                 475                 480

Asn Ile Ile Phe Ser Glu Glu Tyr Asn Thr Ser Asn Pro Asp
                485                 490
```

<210> SEQ ID NO 29
<211> LENGTH: 1560
<212> TYPE: DNA
<213> ORGANISM: Artificial Sequence
<220> FEATURE:
<223> OTHER INFORMATION: Nucleic acid sequence encoding T22d35-Fc in secretable form

<400> SEQUENCE: 29

```
atggattgga cctggagaat cctcttcctt gtagcagcag caacaggtac acatgctatc      60
cctcctcatg ttcaaaagtc cgttaacaac gacatgatcg tcaccgataa caacggtgct     120
gtcaagttcc cacaactctg taagttctgc gatgtgcgtt ctccacatg tgataaccag      180
aagtcctgta tgagcaactg ctcaatcacc tccatctgcg aaaagccaca agaggtatgc     240
gtagctgtat ggcgaaagaa cgatgaaaac atcaccctgg aaaccgtctg tcacgatcca     300
aagctcccat accatgattt catcctggaa gacgcagctt ctccaaagtg tatcatgaag     360
gagaagaaga agcccggtga aaccttcttc atgtgctcct gttcctcaga tgaatgcaac     420
gataacatca tcttctccga ggagtacaac acctccaacc cagatatccc tccacacgtt     480
cagaagtccg taaacaatga catgattgtg accgacaaca cgggggctgt taagttccca     540
cagctctgta agttttgcga cgttaggttc agcacctgtg ataatcagaa gagctgcatg     600
tccaactgca gcatcaccag tatttgcgag aagcctcaag aagtgtgtgt cgctgtttgg     660
agaaagaacg acgaaaacat aaccctggag accgtttgcc acgatccaaa actcccctat     720
cacgatttca ttctggagga cgccgccagt cctaaatgta atgaaagaga agaagaaaa      780
ccagggagaa ccttctttat gtgcagctgc agcagcgacg agtgtaacga taatataatt     840
tttagcgagg agtataatac aagcaatccc gacgagcgca agctgcgt cgagtgccct      900
ccatgccctg cccctcctgt tgccggacct agtgtgtttt tgttcctcc taaacctaaa      960
gatacactca tgattagcag gacacctgag gtgacatgtg tcgtcgtgga cgtgagtcat    1020
gaagaccccg aagtgcagtt taattggtat gtcgacggag tcgaagtcca taatgccaaa    1080
actaaaccaa gggaagaaca gtttaattca acttttcgcg tggtctctgt gctgactgtg    1140
gtgcaccagg actggcttaa tggaaaggaa tacaagtgta aggtgagtaa taagggcctg    1200
cccgccccca ttgaaaaaac tattagtaag actaaagggc agccccgaga gccccaggtg    1260
tatactttgc cccctctcg ggaggagatg actaaaaatc aggtgagtct tacatgtctt     1320
gtgaaaggat ttacccctc tgacatttca gtggagtggg agtctaatgg ccagcccgag    1380
aataattaca aaactactcc ccccatgttg gactctgacg gctcatttt cttgtactct    1440
```

| aaactgacag tggacaaaag tcggtggcag cagggcaatg tgttttcttg ttcagtgatg | 1500 |
| cacgaggccc tgcataatca ctatacacag aaatctctgt ctctgtcacc cggctgatga | 1560 |

<210> SEQ ID NO 30
<211> LENGTH: 1545
<212> TYPE: DNA
<213> ORGANISM: Artificial Sequence
<220> FEATURE:
<223> OTHER INFORMATION: Nucleic acid sequence encoding T22d35-Fc-IgG1-
     v1(CC) in secretable form

<400> SEQUENCE: 30

| atggactgga cctggagaat cctgttcctg gtggctgctg ctaccggaac acacgctatc | 60 |
| cccctcatg tgcagaagtc cgtgaacaat gacatgatcg tgacagataa caatggcgcc | 120 |
| gtgaagtttc ctcagctgtg caagttctgt gacgtgaggt ttagcacctg cgataaccag | 180 |
| aagtcctgca tgagcaattg ttctatcaca tccatctgcg agaagccaca ggaggtgtgc | 240 |
| gtggccgtgt ggcggaagaa cgacgagaat atcaccctgg agacagtgtg ccacgatcct | 300 |
| aagctgccat accatgactt catcctggag gatgctgcct ctcccaagtg tatcatgaag | 360 |
| gagaagaaga agcctggcga gacattcttc atgtgctcct gttccagcga cgagtgcaac | 420 |
| gataatatca tcttcagcga ggagtataac acctctaatc agatatccc accccacgtg | 480 |
| cagaagtctg tcaataacga tatgattgtc acagataaca atggcgctgt gaagtttccc | 540 |
| cagctgtgca atttttgtga cgtgagattt ccacctgtg ataaccagaa gagctgcatg | 600 |
| tctaattgtt ccatcacatc tatttgtgaa aaacctcagg aagtgtgcgt ggccgtgtgg | 660 |
| agaaaaaatg atgaaaacat caccctggag acagtgtgcc atgatcccaa gctgccttat | 720 |
| cacgacttca tcctggaaga cgctgccagc ccaaaatgca ttatgaaaga gaagaagaag | 780 |
| cccggtgaga cattcttcat gtgcagctgt tcttctgatg aatgtaacga taatatcatc | 840 |
| ttttccgagg agtataacac aagcaatccc gacacccaca catgccctcc atgtccagct | 900 |
| cctgagctgc tgggaggacc tagcgtgttc ctgtttcccc ctaagccaaa ggatacctg | 960 |
| atgatcagca ggacccccga ggtgacatgc gtggtggtgg acgtgtctca cgaggacccc | 1020 |
| gaggtgaagt ttaactggta cgtggacggc gtggaggtgc ataatgccaa gaccaagcct | 1080 |
| agggaggagc agtacaactc tacctatcgg gtggtgtccg tgctgacagt gctgcatcag | 1140 |
| gattggctga acggcaagga gtataagtgc aaggtgtcca ataaggctct gccagcccc | 1200 |
| attgagaaga ccatcagcaa ggctaagggc cagccaagag agcccaggt gtacacactg | 1260 |
| ccaccctctc gcgacgagct gaccaagaac caggtgtccc tgacatgtct ggtgaagggc | 1320 |
| ttctatcctt ccgatatcgc tgtggagtgg gagagcaacg gacagccaga gaacaattac | 1380 |
| aagaccacac ctccagtgct ggactctgat ggctccttct ttctgtatag caagctgacc | 1440 |
| gtggacaagt ctaggtggca gcagggcaac gtgtttagct gttctgtgat gcatgaggcc | 1500 |
| ctgcacaatc attacacaca gaagtccctg agcctgtctc tggc | 1545 |

<210> SEQ ID NO 31
<211> LENGTH: 1569
<212> TYPE: DNA
<213> ORGANISM: Artificial Sequence
<220> FEATURE:
<223> OTHER INFORMATION: Nucleic acid sequence encoding T22d35-Fc-IgG1-
     v2(SCC) in secretable form

<400> SEQUENCE: 31

```
atggactgga cctggagaat cctgttcctg gtggctgctg ctaccggaac acacgctatc      60
ccccctcatg tgcagaagtc tgtgaacaat gacatgatcg tgacagataa caatggcgcc     120
gtgaagtttc cccagctgtg caagttctgt gacgtgaggt tttccacctg cgataaccag     180
aagtcttgca tgtccaattg tagcatcaca tctatctgcg agaagcctca ggaggtgtgc     240
gtggccgtgt ggcggaagaa cgacgagaat atcaccctgg agacagtgtg ccacgatcct     300
aagctgccat accatgactt catcctggag gatgctgcca gcccaaagtg tatcatgaag     360
gagaagaaga agcccggcga gacattcttc atgtgctctt gttccagcga cgagtgcaac     420
gataatatca tcttctccga ggagtataac accagcaatc tgacatccc accccacgtg      480
cagaagagcg tcaataacga tatgattgtc acagataaca atggcgctgt gaagtttcca     540
cagctgtgca attttgtga cgtgagattt tctacctgtg ataaccagaa gtcctgcatg      600
agcaattgtt ctatcacatc catctgcgag aagccacagg aagtgtgcgt ggccgtgtgg     660
agaaaaaatg atgaaaacat caccctggag acagtgtgcc atgatcccaa gctgccttat     720
cacgacttca tcctggaaga cgctgcctcc cctaaatgca ttatgaaaga gaagaagaag     780
ccaggtgaga cattcttcat gtgcagctgt tcttctgatg agtgcaacga taacatcatc     840
tttttctgagg agtacaacac atccaatcct gacgtggagc caaagagctc tgataagacc     900
cacacatgcc ctccatgtcc agctcctgag ctgctgggag accatccgt gttcctgttt      960
ccacctaagc ctaaggacac cctgatgatc tccaggaccc cagaggtgac atgcgtggtg    1020
gtggacgtga gccacgagga ccccgaggtg aagtttaact ggtacgtgga tggcgtggag    1080
gtgcataatg ccaagaccaa gccaagggag gagcagtaca acagcaccta tcgggtggtg    1140
tctgtgctga cagtgctgca tcaggactgg ctgaacggca aggagtataa gtgcaaggtg    1200
tctaataagg ctctgccagc ccccatcgag aagaccatct ccaaggctaa gggccagcca    1260
agagagcccc aggtgtacac actgccaccc agccgcgacg agctgaccaa gaaccaggtg    1320
tctctgacat gtctggtgaa gggcttctat ccctctgata tcgctgtgga gtgggagtcc    1380
aacggacagc ctgagaacaa ttacaagacc acacctccag tgctggacag cgatggctct    1440
ttcttctgt attccaagct gaccgtggat aagagcaggt ggcagcaggg caacgtgttt    1500
tcctgtagcg tgatgcatga ggccctgcac aatcattaca cacagaagtc tctgtccctg    1560
agccctggc                                                           1569
```

<210> SEQ ID NO 32
<211> LENGTH: 1578
<212> TYPE: DNA
<213> ORGANISM: Artificial Sequence
<220> FEATURE:
<223> OTHER INFORMATION: Nucleic acid sequence encoding T22d35-Fc-IgG1-v3(GSL-CC) in secretable form

<400> SEQUENCE: 32

```
atggattgga cctggagaat cctgttcctg gtggctgctg ctaccggaac acacgctatc      60
ccccctcatg tgcagaagtc tgtgaacaat gacatgatcg tgacagataa caatggcgcc     120
gtgaagtttc ctcagctgtg caagttctgt gacgtgaggt tttccacctg cgataaccag     180
aagtcctgca tgagcaattg ttctatcaca tccatctgcg agaagccaca ggaggtgtgc     240
gtggccgtgt ggcggaagaa cgacgagaat atcaccctgg agacagtgtg ccacgatcct     300
aagctgccat accatgactt catcctggag gatgctgcca gcccaaagtg tatcatgaag     360
```

```
gagaagaaga agcctggcga gacattcttc atgtgctctt gttccagcga cgagtgcaac    420
gataatatca tcttctccga ggagtataac accagcaatc cagacatccc accccacgtg    480
cagaagagcg tcaataacga tatgattgtc acagataaca atggcgctgt gaagtttccc    540
cagctgtgca aattttgtga cgtgagattt ctacctgtg ataaccagaa gagctgcatg    600
tctaattgtt ccatcacatc tatttgtgaa aaacctcagg aagtgtgcgt ggccgtgtgg    660
agaaaaaatg atgaaaacat caccctggag acagtgtgcc atgatcccaa gctgccttat    720
cacgacttca tcctggaaga cgctgcctcc ccaaaatgca ttatgaaaga gaagaagaag    780
cccggtgaga cattcttcat gtgcagctgt tcttctgatg agtgcaacga taacatcatc    840
ttttctgagg agtacaacac atccaatcct gacgaggag gcagcggagg aggctctgga    900
ggcggcaccc acacatgccc tccatgtcca gctcctgagc tgctgggagg accttccgtg    960
ttcctgtttc ccctaagcc aaaggacacc ctgatgatct ccaggacccc cgaggtgaca    1020
tgcgtggtgg tggacgtgag ccacgaggac cccgaggtga agtttaactg gtacgtggat    1080
ggcgtggagg tgcataatgc caagaccaag ccaagggagg agcagtacaa cagcacctat    1140
cgggtggtgt ctgtgctgac agtgctgcat caggattggc tgaacggcaa ggagtataag    1200
tgcaaggtgt ctaataaggc tctgccagcc cccattgaga gaccatctc caaggctaag    1260 ggccagccaa gagagcccca ggtgtacaca ctgccaccca gccgcgacga gctgaccaag    1320
aaccaggtgt ctctgacatg tctggtgaag ggcttctatc cttctgatat cgctgtggag    1380
tgggagtcca acggacagcc agagaacaat tacaagacca cacctccagt gctggactct    1440
gatggctcct tctttctgta ttccaagctg accgtggaca gagcaggtg gcagcagggc    1500 aacgtgttta gctgttctgt gatgcatgag gccctgcaca atcattacac acagaagtcc    1560
ctgagcctgt ctcctggc                                                 1578
```

<210> SEQ ID NO 33
<211> LENGTH: 1545
<212> TYPE: DNA
<213> ORGANISM: Artificial Sequence
<220> FEATURE:
<223> OTHER INFORMATION: Nucleic acid sequence encoding T22d35-Fc-IgG2-
      v2(CC) in secretable form

<400> SEQUENCE: 33

```
atggattgga cctggagaat cctcttcctt gtagcagcag caacaggtac acatgctatc     60
cctcctcatg ttcaaaagtc cgttaacaac gacatgatcg tcaccgataa caacggtgct    120
gtcaagttcc cacaactctg taagttctgc gatgtgcgtt tctccacatg tgataaccag    180
aagtcctgta tgagcaactg ctcaatcacc tccatctgcg aaaagccaca agaggtatgc    240
gtagctgtat ggcgaaagaa cgatgaaaac atcaccctgg aaaccgtctg tcacgatcca    300
aagctcccat accatgattt catcctggaa gacgcagctt ctccaaagtg tatcatgaag    360
gagaagaaga agcccggtga aaccttcttc atgtgctcct gttcctcaga tgaatgcaac    420
gataacatca tcttctccga ggagtacaac acctccaacc cagatatccc tccacacgtt    480
cagaagtccg taaacaatga catgattgtg accgacaaca acggggctgt taagttccca    540
cagctctgta agttttgcga cgttaggttc agcacctgtg ataatcagaa gagctgcatg    600
tccaactgca gcatcaccag tatttgcgag aagcctcaag aagtgtgtgt cgctgttttgg    660 agaaagaacg acgaaaacat aaccctggag accgtttgcc acgatccaaa actcccatat    720
cacgatttca ttctggagga cgccgccagt cctaaatgta taatgaaaga gaagaagaaa    780
```

```
ccaggggaga ccttctttat gtgcagctgc agcagcgacg agtgtaacga taatataatt    840
tttagcgagg agtataatac aagcaatccc gacgtcgagt gccctccatg ccctgcccct    900
cctgttgccg gacctagtgt gttttgttt cctcctaaac ctaaagatac actcatgatt    960
agcaggacac ctgaggtgac atgtgtcgtc gtggacgtga gtcatgaaga ccccgaagtg   1020
cagtttaatt ggtatgtcga cggagtcgaa gtccataatg ccaaaactaa accaagggaa   1080
gaacagttta attcaacttt tcgcgtggtc tctgtgctga ctgtggtgca ccaggactgg   1140
cttaatggaa aggaatacaa gtgtaaggtg agtaataagg gcctgcccgc ccccattgaa   1200
aaaactatta gtaagactaa agggcagccc cgagagcccc aggtgtatac tttgcccccc   1260
tctcgggagg agatgactaa aaatcaggtg agtcttacat gtcttgtgaa aggatttac    1320 ccctctgaca tttcagtgga gtgggagtct aatggccagc cgagaataa ttacaaaact    1380 actcccccca tgttggactc tgacggctca tttttcttgt actctaaact gacagtggac   1440
aaaagtcggt ggcagcaggg caatgtgttt tcttgttcag tgatgcacga ggccctgcat   1500
aatcactata cacagaaatc tctgtctctg tcacccggct gatga                   1545
```

<210> SEQ ID NO 34
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: May be repeated between 1 and 50 times

<400> SEQUENCE: 34

Gly Gly Gly Gly Ser
1               5

<210> SEQ ID NO 35
<211> LENGTH: 15
<212> TYPE: PRT
<213> ORGANISM: Artificial Sequence
<220> FEATURE:
<223> OTHER INFORMATION: Synthetic

<400> SEQUENCE: 35

Glu Arg Lys Cys Cys Val Glu Cys Pro Pro Cys Pro Ala Pro Pro
1               5                   10                  15

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

Val Glu Cys Pro Pro Cys Pro Ala Pro Pro
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic

```
<400> SEQUENCE: 37

Thr His Thr Cys Pro Pro Cys Pro Ala Pro Glu
1               5                   10

<210> SEQ ID NO 38
<211> LENGTH: 19
<212> TYPE: PRT
<213> ORGANISM: Artificial Sequence
<220> FEATURE:
<223> OTHER INFORMATION: Synthetic

<400> SEQUENCE: 38

Val Glu Pro Lys Ser Ser Asp Lys Thr His Thr Cys Pro Pro Cys Pro
1               5                   10                  15

Ala Pro Glu

<210> SEQ ID NO 39
<211> LENGTH: 22
<212> TYPE: PRT
<213> ORGANISM: Artificial Sequence
<220> FEATURE:
<223> OTHER INFORMATION: Synthetic

<400> SEQUENCE: 39

Gly Gly Gly Ser Gly Gly Gly Ser Gly Gly Thr His Thr Cys Pro
1               5                   10                  15

Pro Cys Pro Ala Pro Glu
                20

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Pro Pro Cys Pro Ala Pro Glu
1               5

<210> SEQ ID NO 41
<211> LENGTH: 13
<212> TYPE: PRT
<213> ORGANISM: Artificial Sequence
<220> FEATURE:
<223> OTHER INFORMATION: Synthetic

<400> SEQUENCE: 41

Asp Lys Thr His Thr Cys Pro Pro Cys Pro Ala Pro Glu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic

<400> SEQUENCE: 42

Val Glu Cys Pro Pro Cys Pro Ala Pro Pro
1               5                   10
```